US010023841B2

(12) United States Patent
Palucka et al.

(10) Patent No.: US 10,023,841 B2
(45) Date of Patent: Jul. 17, 2018

(54) METHODS AND COMPOSITIONS FOR TREATING BREAST CANCER WITH DENDRITIC CELL VACCINES

(71) Applicant: Baylor Research Institute, Dallas, TX (US)

(72) Inventors: Anna Karolina Palucka, Avon, CT (US); Jacques F Banchereau, Montclair, NJ (US); Lee Roberts, Cordova, TN (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 14/719,968

(22) Filed: May 22, 2015

(65) Prior Publication Data

US 2015/0368612 A1    Dec. 24, 2015

Related U.S. Application Data

(60) Provisional application No. 62/002,692, filed on May 23, 2014.

(51) Int. Cl.
| | |
|---|---|
| A61K 39/00 | (2006.01) |
| A61K 35/15 | (2015.01) |
| C12N 5/0784 | (2010.01) |
| A61K 45/06 | (2006.01) |
| A61K 38/20 | (2006.01) |
| A61K 31/337 | (2006.01) |
| A61K 31/675 | (2006.01) |
| A61K 31/704 | (2006.01) |

(52) U.S. Cl.
CPC .......... *C12N 5/0639* (2013.01); *A61K 31/337* (2013.01); *A61K 31/675* (2013.01); *A61K 31/704* (2013.01); *A61K 35/15* (2013.01); *A61K 38/2006* (2013.01); *A61K 39/0011* (2013.01); *A61K 45/06* (2013.01); *A61K 2039/5154* (2013.01); *A61K 2039/5158* (2013.01); *A61K 2039/545* (2013.01); *A61K 2039/6006* (2013.01); *C12N 2501/22* (2013.01); *C12N 2501/2304* (2013.01)

(58) Field of Classification Search
CPC .. C12N 5/0639; A61K 35/15; A61K 39/0011; A61K 2039/5158; A61K 2039/6006; A61K 2039/5154
See application file for complete search history.

(56) References Cited

U.S. PATENT DOCUMENTS

| | | | | |
|---|---|---|---|---|
| 7,144,581 B2 * | 12/2006 | Gaiger | ............... | C07K 14/4748 424/184.1 |
| 7,326,767 B1 * | 2/2008 | Stauss | ................. | C07K 14/4702 424/185.1 |
| 7,622,119 B2 * | 11/2009 | Sugiyama | ............ | C12N 5/0638 424/185.1 |
| 2004/0087532 A1 * | 5/2004 | Banchereau | ....... | A61K 39/0011 514/44 R |
| 2006/0147460 A1 * | 7/2006 | Finn | .................... | A61K 39/0011 424/185.1 |
| 2010/0111986 A1 * | 5/2010 | Scheinberg | ........ | A61K 39/0011 424/185.1 |
| 2010/0291082 A1 * | 11/2010 | Zurawski | ............. | C07K 14/005 424/134.1 |
| 2011/0274653 A1 * | 11/2011 | Banchereau | ......... | A61K 38/162 424/85.5 |
| 2011/0280897 A1 * | 11/2011 | Finn | ................... | C07K 14/4738 424/185.1 |

OTHER PUBLICATIONS

Vella et al., PNAS 106:14010-14015 (2009).*
Paquette et al., J. Leukoc. Biol.Sep. 1998;64(3):358-367.*
Pilon et al., Mol Immunol. Jan. 2009;46(3):437-447.*
Foedermayr et al., Cancer Chemother Pharmacol. Apr. 2014;73(4):771-778.*
Sorensen et al. Clin Cancer Res. Mar. 1, 2009;15(5):1543-1549.*
Oka et al., Proc Natl Acad Sci U S A. 2004; 101(38):13885-13890.*
Sabbatini et al., Clin Cancer Res. Dec. 1, 2012;18(23):6497-6508.*
Anderson, Cancer Invest. 27:361-368, 2009.
Aspord et al., J Exp Med. 204:1037-47, 2007.
Banchereau & Palucka, Nat Rev Immunol. 5:296-306, 2005.
Berry et al., Jama. 295:1658-1667, 2006.
Carey et al., Clin Cancer Res. 13:2329-34, 2007.
Citron et al., J Clin Oncol. 21:1431-1439, 2003.
Coussens et al., Science. 33:286-291, 2013.
Denardo et al., Cancer Discov. 1:54-67, 2011.
Dinarello, Arthritis Rheum. 52:1960-7, 2005.
Disis & Schiffman, Semin Oncol. 28:12-20, 2001.
Egloff et al., Cancer Res. 66:6-9, 2006.
Finn et al., Nat Rev Immunol. 3:630-641, 2003.
Galon et al., Science. 313:1960-1964, 2006.
Jurrmann et al., Ann NY Acad Sci. 1182:111-123, 2009.
Knutson et al., J Clin Invest. 107:477-484 2001.
Kroemer et al., Annu Rev Immunol. 31:51-72, 2013.
Loi et al., J Clin Oncol. 31:860-867, 2013.
Mamounas et al., J Clin Oncol. 23:3686-3696, 2005.
Michaud et al., Science. 334(6062): 1573-7, 2011.
Neidhardt-Berard et al., Breast Cancer Res. 6:R322-328, 2004.
Palucka & Banchereau, Nat Rev Cancer. 12:265-277, 2012.
Park et al., Cancer Res. 68:8400-8409, 2008.

(Continued)

Primary Examiner — Daniel C Gamett
(74) Attorney, Agent, or Firm — Norton Rose Fulbright US LLP

(57) ABSTRACT

Disclosed are compositions and methods for treatment of breast cancer. Disclosed methods and compositions include dendritic cells loaded with cyclin B1 and WT-1 peptide antigens for immunotherapy. These dendritic cell vaccines are administered alone or in combination with other cancer therapies to improve outcomes. Disclosed methods also involve the use of therapeutic agents, such as anakinra, that block the IL-1 inflammation pathway. These agents are used in combination with chemotherapy and/or immunotherapy in treating breast cancer.

19 Claims, 25 Drawing Sheets

(56) References Cited

OTHER PUBLICATIONS

Pedroza et al., J Exp Med. 208(3):479-90, 2011.
Qi et al., Oncol Rep. 28(4):1231-6, 2012.
Saito et al., Breast Cancer Res. 8:R65, 2006.
Ierabe et al., Curr Opin Immunol. 16:157-162, 2004.
Von Minckwitz et al., SABCS. S3-2 abstract, 2011.
Yu et al., Mol Immunol. 38:981-987, 2002.
Zhang et al., Cytokine. 42:39-47, 2008.

* cited by examiner

C
P235
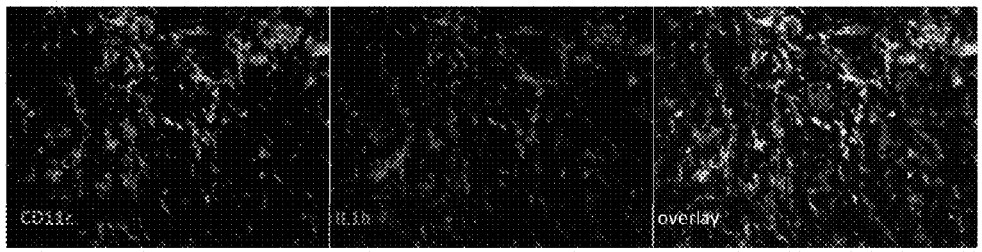
P255
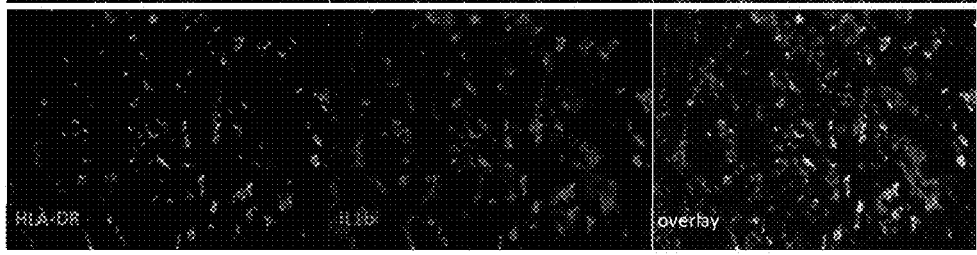
P256
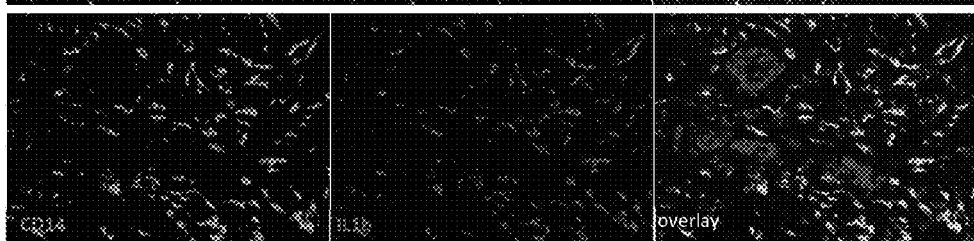
P345
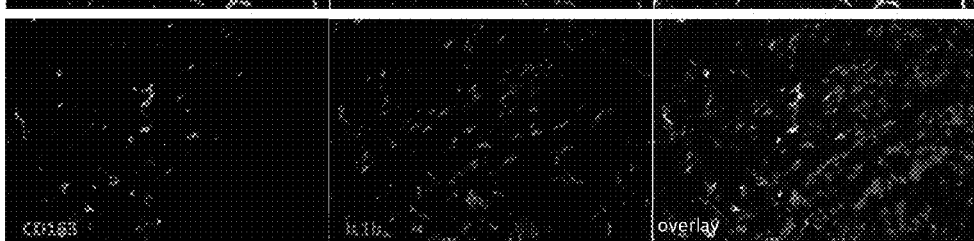
P357
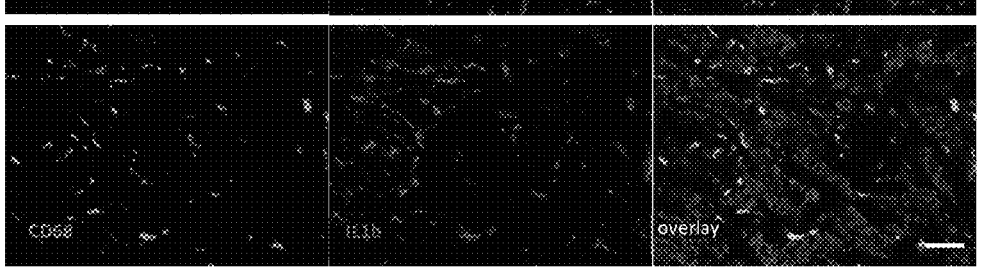
FIG. 5C

D

E

F

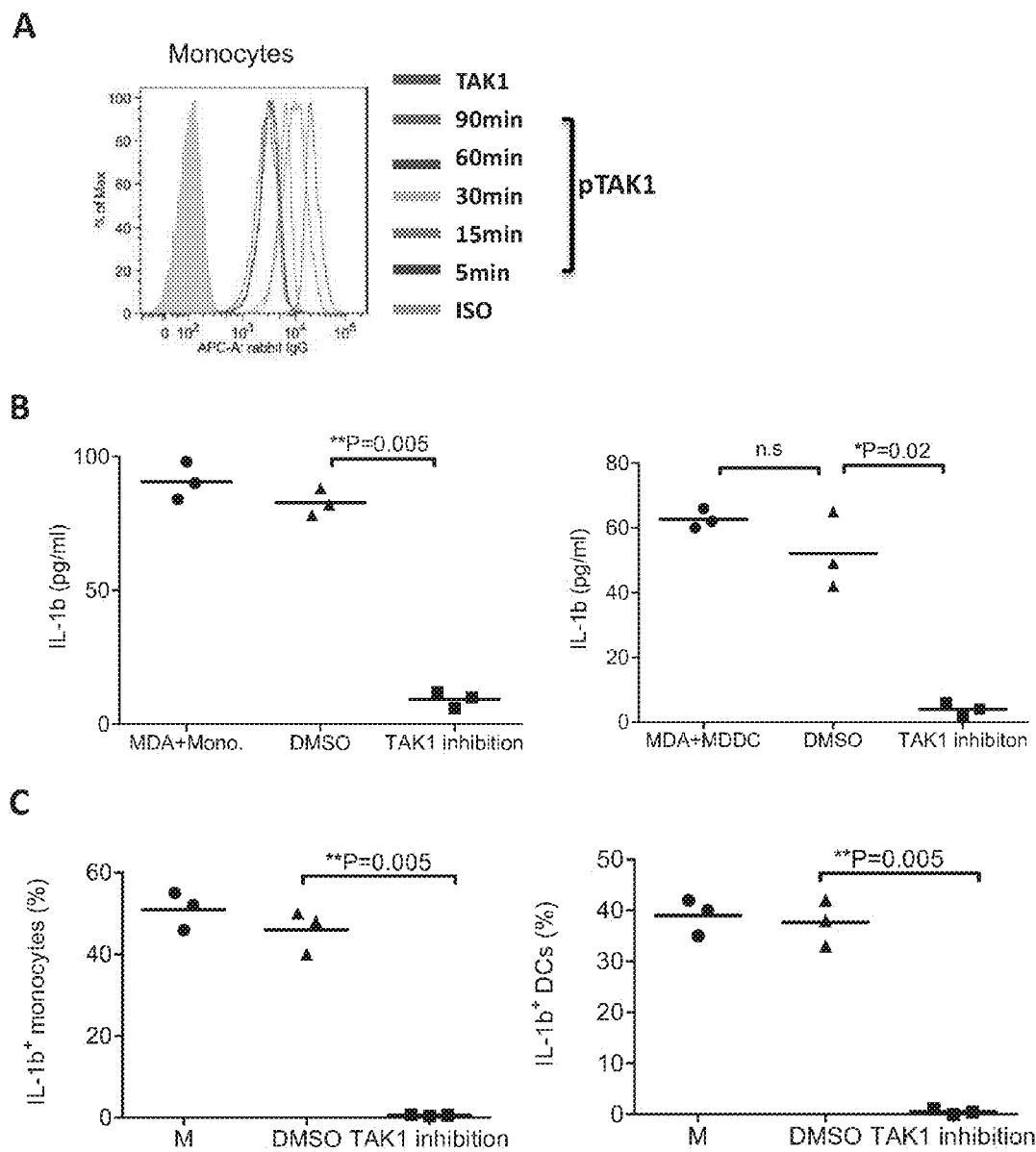
FIG. 14A-C

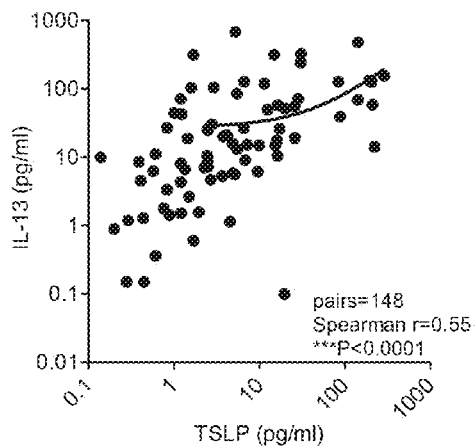
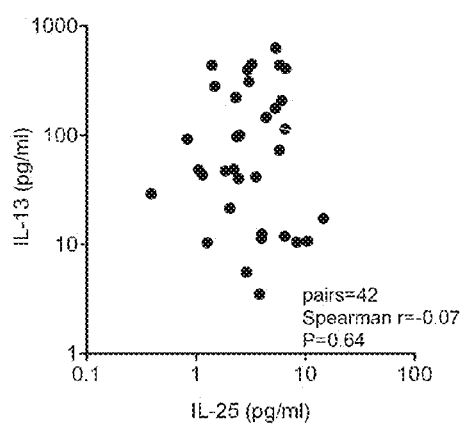
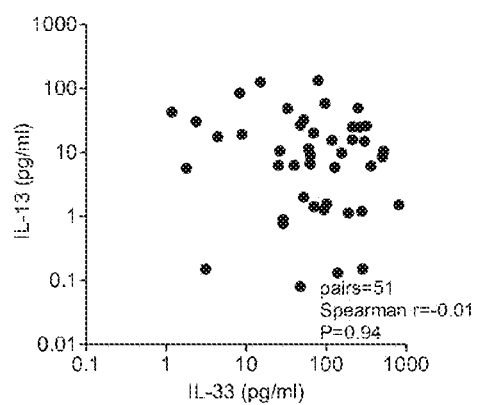
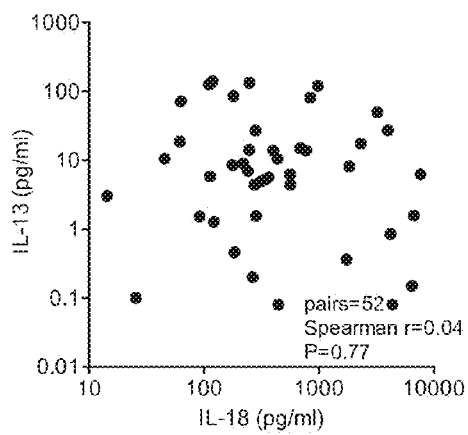
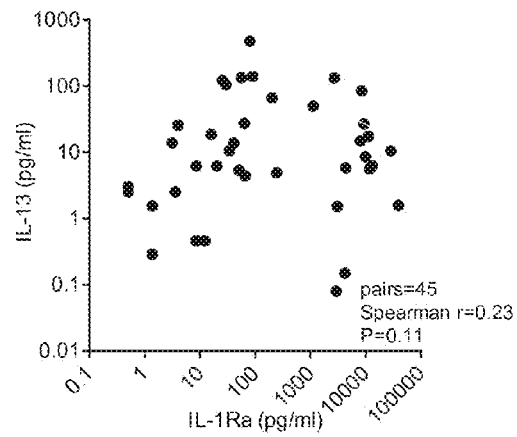
FIG. 16A-16B

SEQUENCE LISTING

<160> NUMBER OF SEQ ID NOS: 52

<210> SEQ ID NO 1
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 1

Asp Trp Leu Val Gln Val Gln Met Lys Phe Arg Leu Leu Gln Glu Thr
1               5                   10                  15

Met Tyr Met Thr Val Ser Ile Ile Asp Arg Phe Met Gln Asn Asn Cys
            20                  25                  30

Val Pro Lys Lys
        35

<210> SEQ ID NO 2
<211> LENGTH: 50
<212> TYPE: PRT
<213> ORGANISM: Artificial Sequence
<220> FEATURE:
<223> OTHER INFORMATION: Synthetic Peptide

<400> SEQUENCE: 2

Met Glu Met Lys Ile Leu Arg Ala Leu Asn Phe Gly Leu Gly Arg Pro
1               5                   10                  15

Leu Pro Leu His Phe Leu Arg Arg Ala Ser Lys Ile Gly Glu Val Asp
            20                  25                  30

Val Glu Gln His Thr Leu Ala Lys Tyr Leu Met Glu Leu Thr Met Leu
        35                  40                  45

Asp Tyr
    50

<210> SEQ ID NO 3
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 3

Ala Ser Gly Ser Glu Pro Gln Gln Met Gly Ser Asp Val Arg Asp Leu
1               5                   10                  15

Asn Ala Leu Leu Pro Ala Val Pro Ser Leu Gly Gly Gly Gly Gly Cys
            20                  25                  30

Ala Leu Pro Val Ser Gly Ala Ala Gln Trp Ala Pro Val Leu Asp Phe
        35                  40                  45

Ala Pro Pro Gly Ala Ser
    50

<210> SEQ ID NO 4

```
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 4

Ala Tyr Gly Ser Leu Gly Gly Pro Ala Pro Pro Ala Pro Pro Pro
1               5                   10                  15

Pro Pro Pro Pro Pro Pro His Ser Phe Ile Lys Gln Glu Pro Ser Trp
                20                  25                  30

Gly Gly Ala Glu Pro His Glu Glu Gln Cys Leu Ser Ala Phe Thr Val
            35                  40                  45

His Phe Ser Gly Gln Phe Thr Gly Thr Ala Gly Ala
        50                  55                  60

<210> SEQ ID NO 5
<211> LENGTH: 48
<212> TYPE: PRT
<213> ORGANISM: Artificial Sequence
<220> FEATURE:
<223> OTHER INFORMATION: Synthetic peptide

<400> SEQUENCE: 5

Cys Arg Tyr Gly Pro Phe Gly Pro Pro Pro Ser Gln Ala Ser Ser
1               5                   10                  15

Gly Gln Ala Arg Met Phe Pro Asn Ala Pro Tyr Leu Pro Ser Cys Leu
                20                  25                  30

Glu Ser Gln Pro Ala Ile Arg Asn Gln Gly Tyr Ser Thr Val Thr Phe
            35                  40                  45

<210> SEQ ID NO 6
<211> LENGTH: 58
<212> TYPE: PRT
<213> ORGANISM: Artificial Sequence
<220> FEATURE:
<223> OTHER INFORMATION: Synthetic Peptide

<400> SEQUENCE: 6

Asp Gly Thr Pro Ser Tyr Gly His Thr Pro Ser His His Ala Ala Gln
1               5                   10                  15

Phe Pro Asn His Ser Phe Lys His Glu Asp Pro Met Gly Gln Gln Gly
                20                  25                  30

Ser Leu Gly Glu Gln Gln Tyr Ser Val Pro Pro Val Tyr Gly Cys
            35                  40                  45

His Thr Pro Thr Asp Ser Cys Thr Gly Ser
        50                  55

<210> SEQ ID NO 7
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 7

Gln Ala Leu Leu Leu Arg Thr Pro Tyr Ser Ser Asp Asn Leu Tyr Gln
1               5                   10                  15

Met Thr Ser Gln Leu Glu Cys Met Thr Trp Asn Gln Met Asn Leu Gly
                20                  25                  30

Ala Thr Leu Lys Gly Val Ala Ala Gly Ser Ser Ser Val Lys Trp
            35                  40                  45
```

```
Thr Glu Gly Gln Ser Asn
        50

<210> SEQ ID NO 8
<211> LENGTH: 55
<212> TYPE: PRT
<213> ORGANISM: Artificial Sequence
<220> FEATURE:
<223> OTHER INFORMATION: Synthetic Peptide

<400> SEQUENCE: 8

Asp Val Arg Arg Val Pro Gly Val Ala Pro Thr Leu Val Arg Ser Ala
1               5                   10                  15

Ser Glu Thr Ser Glu Lys Arg Pro Phe Met Cys Ala Tyr Pro Gly Cys
            20                  25                  30

Asn Lys Arg Tyr Phe Lys Leu Ser His Leu Gln Met His Ser Arg Lys
        35                  40                  45

His Thr Gly Glu Lys Pro Tyr
    50                  55

<210> SEQ ID NO 9
<211> LENGTH: 9
<212> TYPE: PRT
<213> ORGANISM: Influenza A virus

<400> SEQUENCE: 9

Val Ser Asp Gly Gly Pro Asn Leu Tyr
1               5

<210> SEQ ID NO 10
<211> LENGTH: 9
<212> TYPE: PRT
<213> ORGANISM: Influenza A virus

<400> SEQUENCE: 10

Cys Thr Glu Leu Lys Leu Ser Asp Tyr
1               5

<210> SEQ ID NO 11
<211> LENGTH: 9
<212> TYPE: PRT
<213> ORGANISM: Influenza virus

<400> SEQUENCE: 11

Gly Ile Leu Gly Phe Val Phe Thr Leu
1               5

<210> SEQ ID NO 12
<211> LENGTH: 9
<212> TYPE: PRT
<213> ORGANISM: Influenza A virus

<400> SEQUENCE: 12

Phe Met Tyr Ser Asp Phe His Phe Ile
1               5

<210> SEQ ID NO 13
<211> LENGTH: 9
<212> TYPE: PRT
<213> ORGANISM: Artificial Sequence
<220> FEATURE:
<223> OTHER INFORMATION: EBV LMP2A

<400> SEQUENCE: 13
```

```
Cys Leu Gly Gly Leu Leu Thr Met Val
1               5

<210> SEQ ID NO 14
<211> LENGTH: 9
<212> TYPE: PRT
<213> ORGANISM: Artificial Sequence
<220> FEATURE:
<223> OTHER INFORMATION: EBV BMLF1

<400> SEQUENCE: 14

Gly Leu Cys Thr Leu Val Ala Met Leu
1               5

<210> SEQ ID NO 15
<211> LENGTH: 9
<212> TYPE: PRT
<213> ORGANISM: Artificial Sequence
<220> FEATURE:
<223> OTHER INFORMATION: HCMV pp65

<400> SEQUENCE: 15

Asn Leu Val Pro Met Val Ala Thr Val
1               5

<210> SEQ ID NO 16
<211> LENGTH: 9
<212> TYPE: PRT
<213> ORGANISM: Influenza virus

<400> SEQUENCE: 16

Lys Thr Gly Gly Pro Ile Tyr Lys Arg
1               5

<210> SEQ ID NO 17
<211> LENGTH: 10
<212> TYPE: PRT
<213> ORGANISM: Influenza virus

<400> SEQUENCE: 17

Arg Val Leu Ser Phe Ile Lys Gly Thr Lys
1               5                   10

<210> SEQ ID NO 18
<211> LENGTH: 9
<212> TYPE: PRT
<213> ORGANISM: Influenza A virus

<400> SEQUENCE: 18

Ile Leu Arg Gly Ser Val Ala His Lys
1               5

<210> SEQ ID NO 19
<211> LENGTH: 9
<212> TYPE: PRT
<213> ORGANISM: Unknown
<220> FEATURE:
<223> OTHER INFORMATION: EBV

<400> SEQUENCE: 19

Arg Val Arg Ala Tyr Thr Tyr Ser Lys
1               5

<210> SEQ ID NO 20
<211> LENGTH: 9
```

```
<212> TYPE: PRT
<213> ORGANISM: Unknown
<220> FEATURE:
<223> OTHER INFORMATION: EBV

<400> SEQUENCE: 20

Arg Leu Arg Ala Glu Ala Gln Val Lys
1               5

<210> SEQ ID NO 21
<211> LENGTH: 9
<212> TYPE: PRT
<213> ORGANISM: Influenza virus

<400> SEQUENCE: 21

Ser Ile Ile Pro Ser Gly Pro Leu Lys
1               5

<210> SEQ ID NO 22
<211> LENGTH: 10
<212> TYPE: PRT
<213> ORGANISM: Unknown
<220> FEATURE:
<223> OTHER INFORMATION: EBV EBNA 4NP

<400> SEQUENCE: 22

Ala Val Phe Asp Arg Lys Ser Asp Ala Lys
1               5                   10

<210> SEQ ID NO 23
<211> LENGTH: 9
<212> TYPE: PRT
<213> ORGANISM: Unknown
<220> FEATURE:
<223> OTHER INFORMATION: EBV

<400> SEQUENCE: 23

Ile Val Thr Asp Phe Ser Val Ile Lys
1               5

<210> SEQ ID NO 24
<211> LENGTH: 9
<212> TYPE: PRT
<213> ORGANISM: Unknown
<220> FEATURE:
<223> OTHER INFORMATION: EBV

<400> SEQUENCE: 24

Ala Thr Ile Gly Thr Ala Met Tyr Lys
1               5

<210> SEQ ID NO 25
<211> LENGTH: 10
<212> TYPE: PRT
<213> ORGANISM: Unknown
<220> FEATURE:
<223> OTHER INFORMATION: EBV RTA

<400> SEQUENCE: 25

Asp Tyr Cys Asn Val Leu Asn Lys Glu Phe
1               5                   10

<210> SEQ ID NO 26
<211> LENGTH: 9
<212> TYPE: PRT
<213> ORGANISM: Influenza virus
```

```
<400> SEQUENCE: 26

Leu Pro Phe Asp Lys Thr Thr Val Met
1               5

<210> SEQ ID NO 27
<211> LENGTH: 9
<212> TYPE: PRT
<213> ORGANISM: Unknown
<220> FEATURE:
<223> OTHER INFORMATION: EBV

<400> SEQUENCE: 27

Arg Pro Pro Ile Phe Ile Arg Arg Leu
1               5

<210> SEQ ID NO 28
<211> LENGTH: 9
<212> TYPE: PRT
<213> ORGANISM: Influenza virus

<400> SEQUENCE: 28

Glu Leu Arg Ser Arg Tyr Trp Ala Ile
1               5

<210> SEQ ID NO 29
<211> LENGTH: 8
<212> TYPE: PRT
<213> ORGANISM: Unknown
<220> FEATURE:
<223> OTHER INFORMATION: EBV BZLF-1

<400> SEQUENCE: 29

Arg Ala Lys Phe Lys Gln Leu Leu
1               5

<210> SEQ ID NO 30
<211> LENGTH: 9
<212> TYPE: PRT
<213> ORGANISM: Unknown
<220> FEATURE:
<223> OTHER INFORMATION: EBV EBNA 3A

<400> SEQUENCE: 30

Phe Leu Arg Gly Arg Ala Tyr Gly Leu
1               5

<210> SEQ ID NO 31
<211> LENGTH: 9
<212> TYPE: PRT
<213> ORGANISM: Unknown
<220> FEATURE:
<223> OTHER INFORMATION: EBV EBNA 3

<400> SEQUENCE: 31

Gln Ala Lys Trp Arg Leu Gln Thr Leu
1               5

<210> SEQ ID NO 32
<211> LENGTH: 12
<212> TYPE: PRT
<213> ORGANISM: Unknown
<220> FEATURE:
<223> OTHER INFORMATION: HCMV

<400> SEQUENCE: 32

Ser Asp Glu Glu Glu Ala Ile Val Ala Tyr Thr Leu
```

```
1               5                   10

<210> SEQ ID NO 33
<211> LENGTH: 9
<212> TYPE: PRT
<213> ORGANISM: Influenza virus

<400> SEQUENCE: 33

Ser Arg Tyr Trp Ala Ile Arg Thr Arg
1               5

<210> SEQ ID NO 34
<211> LENGTH: 8
<212> TYPE: PRT
<213> ORGANISM: Influenza virus

<400> SEQUENCE: 34

Ala Ser Cys Met Gly Leu Ile Tyr
1               5

<210> SEQ ID NO 35
<211> LENGTH: 9
<212> TYPE: PRT
<213> ORGANISM: Unknown
<220> FEATURE:
<223> OTHER INFORMATION: EBV EBNA 3C

<400> SEQUENCE: 35

Arg Arg Ile Tyr Asp Leu Ile Glu Leu
1               5

<210> SEQ ID NO 36
<211> LENGTH: 9
<212> TYPE: PRT
<213> ORGANISM: Unknown
<220> FEATURE:
<223> OTHER INFORMATION: EBV EBNA 3A

<400> SEQUENCE: 36

Tyr Pro Leu His Glu Gln His Gly Met
1               5

<210> SEQ ID NO 37
<211> LENGTH: 9
<212> TYPE: PRT
<213> ORGANISM: Unknown
<220> FEATURE:
<223> OTHER INFORMATION: CMV pp65

<400> SEQUENCE: 37

Ile Pro Ser Ile Asn Val His His Tyr
1               5

<210> SEQ ID NO 38
<211> LENGTH: 10
<212> TYPE: PRT
<213> ORGANISM: Unknown
<220> FEATURE:
<223> OTHER INFORMATION: EBV

<400> SEQUENCE: 38

Glu Glu Asn Leu Leu Asp Phe Val Arg Phe
1               5                   10

<210> SEQ ID NO 39
<211> LENGTH: 10
```

```
<212> TYPE: PRT
<213> ORGANISM: Unknown
<220> FEATURE:
<223> OTHER INFORMATION: HCMV

<400> SEQUENCE: 39

Glu Phe Phe Trp Asp Ala Asn Asp Ile Tyr
1               5                   10

<210> SEQ ID NO 40
<211> LENGTH: 10
<212> TYPE: PRT
<213> ORGANISM: Unknown
<220> FEATURE:
<223> OTHER INFORMATION: HCMV

<400> SEQUENCE: 40

Thr Pro Arg Val Thr Gly Gly Gly Ala Met
1               5                   10

<210> SEQ ID NO 41
<211> LENGTH: 20
<212> TYPE: DNA
<213> ORGANISM: Artificial Sequence
<220> FEATURE:
<223> OTHER INFORMATION: Synthetic Primer

<400> SEQUENCE: 41
tagcaatcgg ccacattgcc                                          20

<210> SEQ ID NO 42
<211> LENGTH: 20
<212> TYPE: DNA
<213> ORGANISM: Artificial Sequence
<220> FEATURE:
<223> OTHER INFORMATION: Synthetic Primer

<400> SEQUENCE: 42
ctgagtttcc gaatagcctg                                          20

<210> SEQ ID NO 43
<211> LENGTH: 20
<212> TYPE: DNA
<213> ORGANISM: Artificial Sequence
<220> FEATURE:
<223> OTHER INFORMATION: Synthetic Primer

<400> SEQUENCE: 43
tacctgtcct gcgtgttgaa                                          20

<210> SEQ ID NO 44
<211> LENGTH: 22
<212> TYPE: DNA
<213> ORGANISM: Artificial Sequence
<220> FEATURE:
<223> OTHER INFORMATION: Synthetic Primer

<400> SEQUENCE: 44
tctttgggta attttgggat ct                                       22

<210> SEQ ID NO 45
<211> LENGTH: 19
<212> TYPE: DNA
<213> ORGANISM: Artificial Sequence
<220> FEATURE:
<223> OTHER INFORMATION: Synthetic Primer
```

```
<400> SEQUENCE: 45
agccacatcg ctcagacac                                            19

<210> SEQ ID NO 46
<211> LENGTH: 19
<212> TYPE: DNA
<213> ORGANISM: Artificial Sequence
<220> FEATURE:
<223> OTHER INFORMATION: Synthetic Primer

<400> SEQUENCE: 46
gcccaatacg accaaatcc                                            19

<210> SEQ ID NO 47
<211> LENGTH: 20
<212> TYPE: DNA
<213> ORGANISM: Artificial Sequence
<220> FEATURE:
<223> OTHER INFORMATION: Synthetic Primer

<400> SEQUENCE: 47
tgacagggga cacctacaca                                           20

<210> SEQ ID NO 48
<211> LENGTH: 20
<212> TYPE: DNA
<213> ORGANISM: Artificial Sequence
<220> FEATURE:
<223> OTHER INFORMATION: Synthetic Primer

<400> SEQUENCE: 48
atactccaaa tgcccagacg                                           20

<210> SEQ ID NO 49
<211> LENGTH: 23
<212> TYPE: DNA
<213> ORGANISM: Artificial Sequence
<220> FEATURE:
<223> OTHER INFORMATION: Synthetic Primer

<400> SEQUENCE: 49
cttcctcctt aaaactcctc tcc                                       23

<210> SEQ ID NO 50
<211> LENGTH: 22
<212> TYPE: DNA
<213> ORGANISM: Artificial Sequence
<220> FEATURE:
<223> OTHER INFORMATION: Synthetic Primer

<400> SEQUENCE: 50
ctaaggtctc caacgctctt ct                                        22

<210> SEQ ID NO 51
<211> LENGTH: 20
<212> TYPE: DNA
<213> ORGANISM: Artificial Sequence
<220> FEATURE:
<223> OTHER INFORMATION: Synthetic Primer

<400> SEQUENCE: 51
catcacccat cagattgtcg                                           20

<210> SEQ ID NO 52
<211> LENGTH: 19
```

```
<212> TYPE: DNA
<213> ORGANISM: Artificial Sequence
<220> FEATURE:
<223> OTHER INFORMATION: Synthetic Primer

<400> SEQUENCE: 52
gctgcacccc agagaagta                                               19
```

METHODS AND COMPOSITIONS FOR TREATING BREAST CANCER WITH DENDRITIC CELL VACCINES

This application claims the benefit of priority to U.S. Provisional Patent Application Ser. No. 62/002,692, filed May 23, 2014, hereby incorporated by reference in its entirety.

BACKGROUND OF THE INVENTION

A. Field of the Invention

The invention generally relates to the field of medicine. More particularly, it concerns the use of dendritic cell vaccines in immunotherapy of breast cancer. In certain aspects, the dendritic cells display cyclin B1 and WT-1 peptide epitopes and are administered to breast cancer patients.

B. Background

Women with breast cancer who are treated with preoperative chemotherapy have the same survival as those who receive adjuvant therapy; however, pathologic complete response (pCR) after preoperative chemotherapy is a predictor of improved outcomes (Fisher, et al., 1997; Rastrogi, et al., 2008). Those treated with preoperative therapy who achieve a pCR or near pCR have significantly better distant relapse-free survival than those with extensive residual disease independent of pathologic subtype.

Women with triple-negative breast cancer (TNBC) have an increased pCR rate as compared to women with non-TNBC, and those with pCR have a 90% disease-free survival (Liedtke, et al., 2008; Von Minckwitz, et al., 2011). However, women with TNBC who do not achieve a pCR (i.e., those that have residual disease after neoadjuvant chemotherapy) have an increased risk of recurrence, decreased overall survival, and post-recurrence survival as compared to women with non-TNBC who do not achieve a pCR. The risk of recurrence and death is time-dependent and significantly higher for women with TNBC in the first 3 years of follow-up, versus women with non-TNBC (Liedtke, et al., 2008).

These patients have a great unmet medical need as there is no known effective therapy which can improve outcome. Therefore, a high priority for clinical research in patients with locally advanced TNBC is to increase the pathologic complete response (pCR) rate in breast and axilla following preoperative therapy. Patients with T3 and T4 cancers and with clinically N1/N2 axillary disease are at highest risk of not achieving a pCR with standard therapy, and of developing metastatic disease.

SUMMARY OF THE INVENTION

Methods and compositions are provided concerning a breast cancer immunotherapy that can improve outcomes for breast cancer patients. Vaccination of a subject with dendritic cells ("DCs") loaded with cyclin B1 and WT-1 peptide antigens can induce both therapeutic T cell immunity by activating effector T cells and protective T cell immunity by creating tumor-specific memory T cells that can control tumor relapse. Treatment with DC vaccines can be administered in combination with standard chemotherapy, radiation treatment, and surgery in order to improve outcomes for those treatments. DC vaccines can also be administered in combination with the IL-1R antagonist anakinra, which decreases the chronic inflammation that is associated with many solid tumors and that promotes cancer cell survival and metastasis.

In some embodiments, there is disclosed a pharmaceutical composition comprising: isolated, active dendritic cells displaying cyclin B1 peptide epitopes; isolated, active dendritic cells displaying WT-1 peptide epitopes; and/or isolated, active dendritic cells displaying both cyclin B1 peptide epitopes and WT-1 peptide epitopes; or any combination thereof. In some embodiments, the composition can comprise isolated, active dendritic cells wherein each dendritic cell may display both cyclin B1 peptide epitopes and WT-1 peptide epitopes. In some embodiments, the composition can comprise a mixture of isolated, active dendritic cells, some of which display cyclin B1 peptide epitopes and not WT-1 peptide epitopes and some of which display WT-1 peptide epitopes and not cyclin B1 peptide epitopes. In some embodiments, the isolated, active dendritic cells in the composition display only cyclin B1 peptide epitopes or only WT-1 peptide epitopes. In some embodiments, the cyclin B1 peptide epitopes comprise sequences corresponding to SEQ ID NO:1 and/or SEQ ID NO:2 or fragments thereof. In some embodiments, the isolated, active dendritic cells displaying cyclin B1 peptide epitopes have been incubated with cyclin B1 peptide antigens comprising SEQ ID NO:1 and/or SEQ ID NO:2. In some embodiments, the WT-1 peptide epitopes comprise sequences corresponding to one or more of SEQ ID NOs: 3-8 or fragments thereof. In some embodiments, the isolated, active dendritic cells displaying WT-1 peptide epitopes have been incubated with WT-1 peptide antigens comprising one or more of SEQ ID NOs:3-8. In some embodiments, the isolated, active dendritic cells displaying cyclin B1 and the isolated, active dendritic cells displaying WT-1 peptide epitopes have been activated by incubation with lipopolysaccharide, CD40 ligand, and CL075. In certain embodiments, the WT-1 peptide comprises or consists of the amino sequence of SEQ ID NO:2, SEQ ID NO:3, SEQ ID NO:4, SEQ ID NO:5, SEQ ID NO:6, SEQ ID NO:7 or SEQ ID NO:8. In some embodiments, dendritic cells are exposed to 1, 2, 3, 4, 5, 6, 7, or all 8 peptide sequences.

"Peptide epitopes" as used herein includes polypeptides displayed on the surface of dendritic cells in complex with MHC class II molecules. Peptide epitopes can be derived from peptide antigens with which dendritic cells have been incubated. Dendritic cells can take up the peptide antigens and process the peptide antigens for display on the cell surface, a process referred to herein as "antigen loading." Dendritic cells incubated with antigens and displaying peptide epitopes on their surface are in some instances referred to herein as "antigen-loaded dendritic cells." The "peptide epitopes" referred to herein are at least 9 amino acids in length.

"Isolated dendritic cells" as used herein refers to dendritic cells that are found outside the body, separate from the environment in which dendritic cells are usually found in the body.

In some embodiments, isolated dendritic cells in the compositions and methods described herein are derived from monocytes that have been isolated from a subject's blood. Monocytes can be isolated from a subject's blood by any process known to those of skill in the art. As an example, monocytes can be isolated by a process that begins with removing white blood cells from a subject's blood stream by apheresis, which can result in a blood composition enriched for white blood cells with minimal presence of red blood cells. Monocytes can be further isolated or enriched from the apheresis product by elutriation, which results in a composition enriched for monocytes. The elutriation product may contain at least or at most 70, 75, 80, 85, 90, 95% or more monocytes as a percentage of total cells present in the composition (or any range derivable therein). Thus, as used herein, "isolated monocytes" can include compositions that include some proportion of other types of cells and "isolating monocytes" can refer to a process that results in enrichment of monocytes and not necessarily complete purification of monocytes.

In some embodiments of the methods described herein, dendritic cells are derived from monocytes by incubating the monocytes with IFNα and GM-CSF. This process is also referred to as differentiation. The dendritic cells that are formed by incubating monocytes with IFNα and GM-CSF are in some instances referred to herein as "IFN-DCs."

Also disclosed is a pharmaceutical composition for treating breast cancer in a subject comprising isolated, active dendritic cells that (i) are derived from monocytes isolated from the subject's blood and differentiated into dendritic cells in vitro and (ii) display cyclin B1 peptide epitopes, WT-1 peptide epitopes, or both cyclin B1 peptide epitopes and WT-1 peptide epitopes. In some embodiments, the isolated, active dendritic cells display WT-1 peptide epitopes. In some embodiments, the isolated, active IFN-dendritic cells display both cyclin B1 peptide epitopes and WT-1 peptide epitopes. In some embodiments, the cyclin B1 peptide epitopes comprise sequences corresponding to SEQ ID NO:1 and/or SEQ ID NO:2 or fragments thereof. In some embodiments, the isolated, active dendritic cells have been incubated with cyclin B1 peptide antigens comprising SEQ ID NO:1 and/or SEQ ID NO:2. In some embodiments, the WT-1 peptide epitopes comprise sequences corresponding to one or more of SEQ ID NOs:3-8 or fragments thereof. In some embodiments, the isolated, active dendritic cells have been incubated with WT-1 peptide antigens comprising one or more of SEQ ID NOs:3-8. In some embodiments, the isolated, active dendritic cells have been derived from monocytes isolated from the subject by incubating the monocytes with IFNα and GM-CSF. In certain embodiments, one or more peptide antigens may be excluded in the embodiment.

Also disclosed is a pharmaceutical composition for treating breast cancer in a subject made by a method comprising: isolating monocytes from the subject's blood; differentiating the isolated monocytes into dendritic cells; incubating the dendritic cells with one or more isolated cyclin B1 peptide antigens and/or WT-1 peptide antigens; and activating the dendritic cells. In some embodiments, the dendritic cells are incubated with one or more isolated WT-1 peptide antigens. In some embodiments, the dendritic cells are incubated with isolated cyclin B1 and WT-1 peptide antigens. In some embodiments, the one or more isolated cyclin B1 peptide antigens comprise SEQ ID NO:1 and/or SEQ ID NO:2. In some embodiments, the one or more isolated cyclin B1 peptide antigens comprise SEQ ID NO:1 and SEQ ID NO:2. In some embodiments, the one or more isolated WT-1 peptide antigens comprise one or more of SEQ ID NOs:3-8. In some embodiments, the one or more isolated WT-1 peptide antigens comprise SEQ ID NOs:3-8. In some embodiments, the step of differentiating the isolated monocytes is performed by incubating the isolated monocytes with IFNα and GM-CSF. In some embodiments, the step of activating the dendritic cells is performed by incubating the dendritic cells with lipopolysaccharide, CD40 ligand, and CL075 before, during, or after the time that the dendritic cells are incubated with one or more isolated cyclin B1 peptide antigens and/or WT-1 peptide antigens. In certain embodiments, one or more peptide antigens may be excluded in the embodiment.

Also disclosed is a method of treating breast cancer in a subject comprising administering to the subject any of the pharmaceutical compositions described herein. In some embodiments, the subject has triple negative breast cancer. In some embodiments, the subject has been diagnosed with triple negative breast cancer. In some embodiments, the subject has previously been administered a chemotherapeutic agent. In some embodiments, the chemotherapy did not result in a pathologic complete response in the subject. In some embodiments, the breast cancer is resistant to chemotherapy. In some embodiments, the breast cancer has been determined to be resistant to chemotherapy. In some embodiments, the method further comprises administering to the subject an IL-1 receptor (IL-1R) antagonist in combination with the composition of any one of claims 1 to 26. In some embodiments, the IL-1R antagonist is anakinra. In some embodiments, the method further comprises administering to the subject one or more chemotherapeutic agents in combination with the composition of any one of claims 1 to 26. In some embodiments, the one or more chemotherapeutic agents comprise one or more of doxorubicin, cyclophosphamide, Adriamycin, Cytoxan, and paclitaxel. In some embodiments, the method further comprises treating the breast cancer by performing surgery and/or radiation. It is specifically contemplated that one or more chemotherapeutic agents or surgery or radiation may be excluded in certain embodiments.

Methods of treating breast cancer described herein can include methods that result in decreased growth of cancer cells, inhibition of growth of cancer cells, killing of cancer cells, and/or shrinking of cancer tumors. The methods described herein can also be used to reduce the metastagenicity of breast cancer, to enhance the effectiveness of other cancer treatments such as chemotherapy, surgery, or radiation, or to reduce the likelihood of recurrence of a breast cancer.

In the methods described herein, administration of pharmaceutical compositions comprising antigen-loaded dendritic cells can be performed in conjuction or in combination with surgery, radiation, chemotherapy, or other breast cancer treatments. Administration of antigen-loaded DCs can be performed before, during, or after the time that the other treatments are administered. The other cancer treatments administered in conjuction with pharmaceutical compositions comprising antigen-loaded dendritic cells can be any treatment known by those of skill in the art.

Also disclosed herein is a method of making active, antigen-loaded dendritic cells for treating breast cancer in a subject comprising: isolating monocytes from the subject's blood; differentiating the isolated monocytes into dendritic cells; incubating the dendritic cells with one or more isolated cyclin B1 peptide antigens and/or WT-1 peptide antigens; and activating the dendritic cells. In some embodiments, the dendritic cells are incubated with isolated WT-1 peptide antigens. In some embodiments, the dendritic cells are incubated with one or more isolated cyclin B1 peptide antigens and one or more WT-1 peptide antigens. In some embodiments, the one or more isolated cyclin B1 peptide antigens comprise SEQ ID NO:1 and/or SEQ ID NO:2. In some embodiments, the one or more isolated cyclin B1 peptide antigens comprise SEQ ID NO:1 and SEQ ID NO:2. In some embodiments, the one or more isolated WT-1 peptide antigens comprise one or more of SEQ ID NOs:3-8. In some embodiments, the one or more isolated WT-1 peptide antigens comprise SEQ ID NOs:3-8. In some embodiments, the step of differentiating the isolated monocytes is performed by incubating the isolated monocytes with IFNα and GM-CSF. In some embodiments, the step of activating the dendritic cells is performed by incubating the dendritic cells with lipopolysaccharide, CD40 ligand, and CL075 before, during, or after the time that the dendritic cells are incubated with one or more isolated cyclin B1 peptide antigens and/or WT-1 peptide antigens. The step of activating the dendritic cells can also be performed by incubating the dendritic cells with a composition comprising lipopolysaccharide, CD40 ligand, and/or CL075. In certain embodiments, one or more peptide antigens may be excluded in the embodiment.

Also disclosed is a method of treating breast cancer in a subject comprising: isolating monocytes from the subject's blood; differentiating the monocytes to form dendritic cells; incubating the dendritic cells with an antigenic composition comprising (i) one or more isolated cyclin B1 peptide antigens and/or WT-1 peptide antigens and (ii) one or more dendritic cell activating agents to form activated, antigen-loaded dendritic cells; and administering to the subject a first pharmaceutical composition comprising the activated, antigen-loaded dendritic cells. In some instances, the one or more cyclin B1 peptide antigens and/or one or more WT-1 peptide antigens are added to a composition comprising the dendritic cells before the dendritic cell activating agents are added. In other instances, one or more peptide antigens can be added to the dendritic cells at the same time as or after the dendritic cell activating agents. "Dendritic cell activating agents" include agents that enhance the ability of dendritic cells to stimulate an immune response when administered to a subject. In some embodiments, the method further comprises obtaining blood from the subject. In some embodiments, the antigenic composition comprises one or more isolated WT-1 peptide antigens. In some embodiments, the antigenic composition comprises one or more isolated cyclin B1 and WT-1 peptide antigens. In some embodiments, the one or more isolated cyclin B1 peptide antigens comprise SEQ ID NO:1 and/or SEQ ID NO:2. In some embodiments, the one or more isolated cyclin B1 peptide antigens comprise SEQ ID NO:1 and SEQ ID NO:2. In some embodiments, the one or more isolated WT-1 peptide antigens comprise one or more of SEQ ID NOs:3-8. In some embodiments, the one or more isolated WT-1 peptide antigens comprise SEQ ID NOs:3-8. In some embodiments, the step of differentiating the isolated monocytes is performed by incubating the isolated monocytes with IFNα and GM-CSF. In some embodiments, the one or more dendritic cell activating agents comprise lipopolysaccharide, CD40 ligand, and/or CL075. In some embodiments, the one or more dendritic cell activating agents comprise lipopolysaccharide, CD40 ligand, and CL075. In some embodiments, the subject has triple negative breast cancer. In some embodiments, the subject has been diagnosed with triple negative breast cancer. In some embodiments, the subject has previously been administered chemotherapy. In some embodiments, the chemotherapy did not result in a pathologic complete response in the subject. In some embodiments, the breast cancer is resistant to chemotherapy. In some embodiments, the breast cancer has been determined to be resistant to chemotherapy. In some embodiments, the method further comprises administering to the subject an IL-1R antagonist. In some embodiments, the IL-1R antagonist is anakinra. In some embodiments, the first pharmaceutical composition is administered intratumorally, subcutaneously, or intraveinously. In some embodiments, the first pharmaceutical composition is administered to the subject in multiple doses. In some embodiments, each dose of the first pharmaceutical composition comprises between about $0.5 \times 10^6$ and $15 \times 10^6$ viable cells of the active, antigen-loaded dendritic cells. In some embodiments, each dose of the first pharmaceutical composition comprises at least about $15 \times 10^6$ viable cells of the active, antigen-loaded dendritic cells. In some embodiments, the concentration of the active, antigen-loaded dendritic cells in the first pharmaceutical composition is between about $1 \times 10^6$ and $15 \times 10^6$ viable cells/ml. In some embodiments, is approximately or is at least or at most about $15 \times 10^6$ viable cells/ml. In some embodiments, the first pharmaceutical composition is administered to the subject in combination with one or more chemotherapeutic agents. In some embodiments, the one or more chemotherapeutic agents comprise one or more of doxorubicin, cyclophosphamide, and paclitaxel. In some embodiments, the first pharmaceutical composition is administered to the subject intratumorally. In some embodiments, the first pharmaceutical composition is administered to the subject in multiple doses. In some embodiments, each dose of the first pharmaceutical composition comprises approximately $0.6 \times 10^6$ viable cells of the active, antigen-loaded dendritic cells. In some embodiments, the concentration of the active, antigen-loaded dendritic cells in the first pharmaceutical composition is about $3 \times 10^6$ viable cells/ml. In some embodiments, the method further comprises administering to the subject a second pharmaceutical composition comprising the active, antigen-loaded dendritic cells. In some embodiments, the second pharmaceutical composition is administered subcutaneously. In some embodiments, the second pharmaceutical composition is administered to the subject in multiple doses. In some embodiments, each dose of the second pharmaceutical composition comprises approximately $15 \times 10^6$ viable cells of the active, antigen-loaded dendritic cells. In some embodiments, the concentration of the active, antigen-loaded dendritic cells in the second pharmaceutical composition is approximately or at least about $15 \times 10^6$ viable cells/ml. In some embodiments, the second pharmaceutical composition is administered to the subject in combination with one or more chemotherapeutic agents. In some embodiments, the one or more chemotherapeutic agents comprise one or more of doxorubicin, cyclophosphamide, and paclitaxel. In some embodiments, the method further comprises surgically removing breast cancer tissue and/or administering radiation treatment.

Also disclosed is a method of treating cancer in a subject comprising: isolating monocytes from the subject's blood; differentiating the monocytes into dendritic cells by incubating the monocytes with IFNα and GM-CSF; incubating the dendritic cells with an antigenic composition comprising one or more isolated cyclin B1 peptide antigens and/or WT-1 peptide antigens, lipopolysaccharide, CD40 ligand, and CL075 to form activated, antigen-loaded dendritic cells; and administering to the subject a pharmaceutical composition comprising the activated, antigen-loaded dendritic cells in combination with one or more chemotherapeutic agents and an antagonist of IL-1R.

Also disclosed is a method of thawing a frozen dendritic cell vaccine for administration to a subject comprising: thawing frozen dendritic cells by suspending the dendritic cells in Lactated Ringer's solution; washing the dendritic cells with Lactated Ringer's solution; and suspending the dendritic cells in Lactated Ringer's solution at a concentration of approximately or at least about $15 \times 10^6$ viable cells/ml. In some embodiments, the frozen dendritic cells are active, antigen-loaded dendritic cells. In some embodiments, the active-antigen-loaded dendritic cells display cyclin B1 and/or WT-1 peptide epitopes, which may be derived from SEQ ID NOs:1-8. In certain embodiments, one or more peptide epitopes may be excluded in an embodiment.

Also disclosed is a method of treating cancer in a subject comprising administering to the subject a chemotherapeutic agent and administering to the subject a therapeutic agent that blocks IL-1β and/or blocks the IL-1 inflammation pathway. In some embodiments, the agent is an antibody that specifically binds IL-1 receptor or IL-1β. It may be a monoclonal or humanized or chimeric antibody. Alternatively, it may be a single-chain antibody. In further embodiments, the agent is a peptide or polypeptide. In some embodiments, the therapeutic agent that blocks IL-1β and/or blocks the IL-1 inflammation pathway is anakinra. In some embodiments, the therapeutic agent that blocks IL-1β and/or blocks the IL-1 inflammation pathway is rilonacept or canakinumab. In some embodiments, the chemotherapeutic agent is Nab paclitaxel, eribulin, capecitabine, or vinorelbine. In some embodiments, anakinra is administered to the subject before the first time the chemotherapeutic agent is administered to the subject. In some embodiments, the anakinra may be administered to a subject who has previously been administered chemotherapy but is not currently undergoing chemotherapy at the time the administration of anakinra begins. In such embodiments, anakinra administration may begin before the beginning of another chemotherapy treatment regimen. In some embodiments, anakinra is administered to the subject daily for 14 days before the first time the chemotherapeutic agent is administered to the subject. In some embodiments, anakinra is administered to the subject daily during the time in which the chemotherapeutic agent is administered to the subject. In some embodiments, each dose of anakinra is 100 mg or about 100 mg. In some embodiments, each dose of anakinra is between about 50 and 150 mg, between about 75 and 125 mg, or between about 90 and 110 mg.

In some embodiments, it is contemplated that whole cells may be excluded as the source of antigen and that, accordingly, the antigenic composition with which dendritic cells are incubated may exclude whole cells. Thus, in some embodiments, the only source of cyclin B1 and/or WT-1 peptide for loading dendritic cells is isolated polypeptides.

It is contemplated that other blockers of IL-1β and/or the IL-1 inflammation pathway, including but not limited to rilonacept and canakinumab, may be administered instead of or in addition to anakinra in any of the embodiments described herein in which anakinra is administered.

The compositions and methods described herein may include dendritic cells that display positive control peptide epitopes derived from one or more of the peptide antigens in the CEF protein library (SEQ ID NOs:9-40) or that have been incubated with the peptides of SEQ ID NOs:9-40. In certain embodiments, one or more peptides may be excluded in an embodiment.

The terms "a" and "an" are defined as one or more unless this disclosure explicitly requires otherwise.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

The feature or features of one embodiment may be applied to other embodiments, even though not described or illustrated, unless expressly prohibited by this disclosure or the nature of the embodiments.

Any method or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate by way of example and not limitation. In all figures, IL-1a indicates IL-1α, and IL-1b indicates IL-1β.

FIG. 5A-5C. A) level of IL-1β is determined by luminex in supernatants of breast tumor fragments (T) or macroscopic uninvolved surrounding tissue (ST) post PMA/ionomycin stimulation; B-D) Frozen tissue sections from patients were analyzed by immunofluorescence staining. B) Primary tumor from patient was stained with anti-TSLP (top right panel), anti-IL-1β (top lef panel), anti-cytokeratin-19 (bottom left panel) antibodies. Bar: 20 um. C) Primary tumor sections from different patients (P235, P255, P256, P345, P357, from above to bottom) were stained for immune infiltrates markers, including CD11c, HLA-DR, CD14, CD163, and CD68 (left panels), together with anti-IL-1β (center panels) antibody. Bar: 90 um.

FIG. 14A-14C. A) monocytes were treated with rhuTGF-β1 (10 ng/ml) for different time periods as indicated. pTAK1 and total TAK1 was detected by specific staining and analyzed on FACS. The far left, filled-in curve is the ISO signal. B) MDA-MB231 cells were co-cultured with monocytes or MDDCs for 16-48 hours in presence of TAK1 inhibitor or DMSO. B) IL-1β levels were detected by Luminex in the sups after 48 hours of co-culture. C) IL-1β expressing CD11c cells after 16 hours co-culture were quantified by intracellular staining with anti-IL-1β antibody, and analyzed on FACS.

FIG. 16A-16B. A-B) levels of cytokines were determined by luminex or ELISA in supernatants of breast tumor fragments post PMA/ionomycin stimulation; A) levels of IL-13 were plotted against TSLP from the same patient. B) Levels of IL-18, IL-25, IL-33, GM-CSF, respectively were plotted against the level of IL-13 from the same patient. Analysis was performed using nonparametric spearman correlation to determine the level of correlation between two cytokines. Nonparametric t test was used.

DETAILED DESCRIPTION OF THE INVENTION

Figure 1:
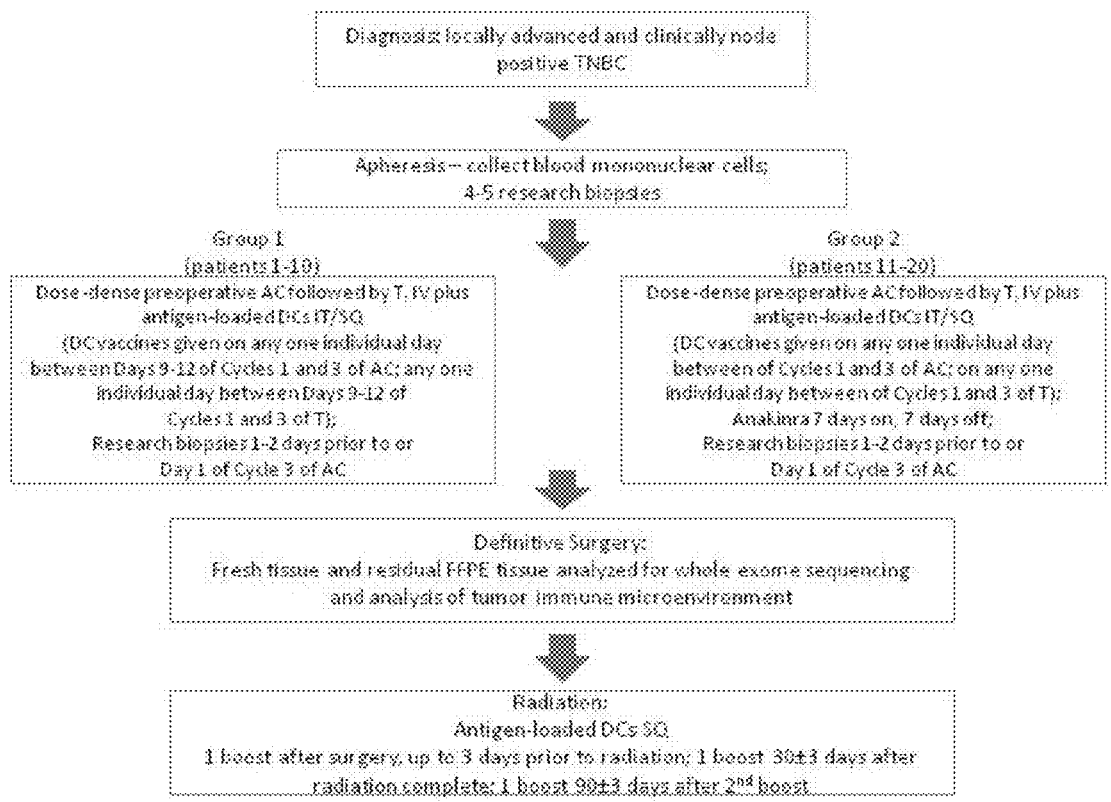
FIG. 1—Study design. This exploratory pilot safety, open label trial will evaluate the combination of preoperative chemotherapy and Dendritic Cell (DC) vaccinations in 2 groups of patients with LA TNBC.

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are given to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

A. Breast Cancer and Immunotherapy

Immunotherapy is an attractive strategy for overcoming chemotherapy resistance in TNBC patients and some preliminary studies have been carried out (Park, et al., 2008; Knutson, et al., 2001; Anderson, 2009; Disis & Schiffman, 2001). Briefly, recent studies have shown that human breast cancers can be immunogenic, and that enhancing the immune effector function already present may augment the cytotoxic effects of standard therapies (Anderson, 2009; Disis & Schiffman, 2001). In one preclinical study, IGFBP-2 was found at elevated levels in breast cancer patients' sera, and an IGFBP-2—specific T-cell response inhibited tumor growth in a breast cancer mouse model (Park, et al., 2008). In a phase I clinical trial, 19 patients with HER2-overexpressing breast cancer were vaccinated with HER2 peptide-specific T-cells, resulting in the generation of both CD4 and CD8 T-cell immunity. The resulting peptide-specific T-cells recognized endogenous HER2 protein and the immunity was maintained for a median of 12 months after the last vaccination (Knutson, et al, 2001). More recently, breast cancer tissues from a phase III clinical trial were analyzed for lymphocytic infiltrate, and the results demonstrated that increased infiltration of lymphocytes in tumor and stroma was associated with an overall good prognosis in ER-negative/HER2-negative breast cancer patients. These findings were consistent regardless of the chemotherapy type administered, demonstrating that greater lymphocytic infiltration was a prognostic factor for ER-negative/HER2-negative breast cancer (Loi, et al., 2013).

The presence of naturally occurring immunity against a broad range of tumor-associated antigens including HER-2/neu, MUC1, cyclin B1 and survivin has now been documented in patients with breast cancer (Finn, 2003). However, the natural immune response to the cancer co-exists with the cancer, and is therefore not protective, either because of tumor escape, for example, through clonal evolution, or because it might have been generated in and/or elicited an inappropriate immunosuppressive microenvironment.

There are numerous strategies under investigation aimed at enhancing a patient's immunologic resistance to cancer. Among these are 1) non-specific activation of the immune system with microbial components or cytokines; 2) antigen-specific adoptive immunotherapy with antibodies and/or T cells; and 3) antigen-specific active immunotherapy (vaccination). The major limitation of antibodies is that target proteins must be expressed on the cell surface whereas targets for T cells can be intracellular proteins whose peptides are presented on the cell surface in complexes with MHC molecules (Townsend, et al., 1985). The identification of defined tumor antigens in humans (Doon, et al., 1994; Rosenberg, 1997) prompted the development of adoptive T cell therapy. Yet, vaccination remains the most attractive strategy because of its expected inducement of both therapeutic T cell immunity (effector T cells) and protective T cell immunity (tumor-specific memory T cells that can control tumor relapse) (Finn, 2003; Pardoll, 1998; Gilboa, 1999).

Several clinical studies have now demonstrated that immunity against tumor antigens can be enhanced in cancer patients by vaccination with ex vivo-generated tumor antigen-loaded dendritic cells (DCs). This strategy capitalizes on the unique capacity of DCs to prime lymphocytes and to regulate and maintain immune responses. Whereas a number of antigen-presenting cells can activate memory T cells, only DCs can prime naive T cells. This feature is essential to successful vaccination as it might allow generation of a "new" immune response, possibly not compromised by the cancer (Palucka & Banchereau, 2012).

B. Therapeutic Dendritic Cell Vaccines

Treatment methods described herein involve administering antigen-loaded dendritic cells to a subject. Multiple phase I/II clinical trials testing ex vivo-generated DC vaccines in patients with stage IV melanoma, HIV, and more recently pancreatic cancer, have been performed. It has been found that some patients can experience durable tumor regressions as well as prolonged survival (reviewed in Banchereau & Palucka, 2005). A DC vaccine optimized for $CD8^+$ T cell responses, i.e., GM-CSF/IFN-α-generated DCs activated with TLR ligands and CD40L, has also been developed. A closed system for vaccine generation has been developed, as has a frozen vaccine that has been successfully administered in multicenter clinical trials in patients with melanoma and in patients with HIV.

The dendritic cells used in the vaccines are generated from autologous monocytes by culturing in the presence of GM-CSF and IFN-α (IFN-DC), which demonstrate powerful priming functions in vitro. The in vivo activity IFN-DC has been tested in phase I/II clinical trials in patients with stage IV melanoma and in patients with HIV. Early results show the induction of immune and clinical responses as well as a good safety/tolerability profile.

In some embodiments, the dendritic cell vaccines comprise dendritic cells displaying a variety of antigens, including a mixture of tumor antigens and control antigens. The tumor antigens consist of eight immunogenic long-peptides: Cyclin $B1_{207-242}$ (36 mer Peptide), Cyclin $B1_{285-334}$ (50 mer Peptide), $WT1_{61-114}$ (54 mer Peptide), $WT1_{115-174}$ (60 mer Peptide), $WT1_{175-222}$ (48 mer Peptide), $WT1_{223-280}$ (58 mer Peptide), $WT1_{281-334}$ (54 mer Peptide) and $WT1_{367-421}$ (55 mer Peptide). The control antigens are the cytotoxic T-lymphocyte (CTL)-CEF-Class I Peptide Library Pool comprised of 32 peptides, each corresponding to a defined HLA class I restricted T-cell epitope from Cytomegalovirus, Epstein-Ban virus and Influenza virus.

The dendritic cells can be activated at the same time that they are incubated with peptide antigens. Antigen loading and dendritic cell activation can also be performed in subsequent steps. Activation can be accomplished by incubation of the dendritic cells with lipopolysaccharide (LPS), CD40 ligand (CD40-L), and the TLR7/8 agonist CL075. Research results demonstrate that the combination of LPS (TLR4 ligand), CD40L and CL075 (TLR 7/8 agonist) is superior to poly I:C (TLR3) and/or a mixture of inflammatory cytokines in priming IFN-DC to secrete IL-12p40, IL-12p70 and IL-23, which are potent T-cell signals. LPS/CD40L/CL075-activated IFN-DC induce potent antigen-specific $CD8^+$T-cell responses in vitro.

2. Synopsis—Parameters for Manufacture of BIIR-BrcaVax-001 DC Vaccine

The following parameters have been selected for the manufacture of the BIIR-BrcaVax-001 DC vaccine product intended for treating breast cancer patients enrolled in the proposed Phase I/II clinical trial.

Source of Monocytes: Elutriation enriched from the patient's PBMC collected by apheresis.

Cell Culture: DC generated by culturing the monocytes in serum-free media supplemented with GM-CSF/IFN-α for 3 days.

Antigen Loading: Three different sets of peptide antigens listed below will be loaded onto the DC in the BIIR-BrcaVax-001 vaccine product. These include: Cyclin B1 36 mer and 50 mer antigen peptides, six long-peptides derived from the WT-1 tumor antigen, and CEF which is a mixture of viral antigens as a vaccine positive control.

Cyclin B1 Peptide Antigens

```
Cyclin B1₂₀₇₋₂₄₂ (36 mer Peptide)
                                         (SEQ ID NO: 1)
NH₂-DWLVQV QMKFRL LQETMY MTVSII DRFMQN NCVPKK-COOH Cyclin B1₂₈₅₋₃₃₄ (50 mer Peptide)
                                         (SEQ ID NO: 2)
NH₂-MEMKIL RALNFG LGRPLP LHFLRR ASKIGE VDVEQH

TLAKYL MELTML DY-COOH
```

WT-1 Peptide Antigens

```
                                         (SEQ ID NO: 3)
WT1₆₁₋₁₁₄ (54 mer Peptide)
NH₂-ASGSEP QQMGSD VRDLNA LLPAVP SLGGGG GCALPV

SGAAQW APVLDF APPGAS-COOH (SEQ ID NO: 4)
WT1₁₁₅₋₁₇₄ (60 mer Peptide)
NH₂-AYGSLG GPAPPP APPPPP PPPPHS FIKQEP SWGGAE

PHEEQC LSAFTV HFSGQF TGTAGA-COOH (SEQ ID NO: 5)
WT1₁₇₅₋₂₂₂ (48 mer Peptide)
NH₂-CRYGPF GPPPPS QASSGQ ARMFPN APYLPS CLESQP

AIRNQG YSTVTF-COOH (SEQ ID NO: 6)
WT1₂₂₃₋₂₈₀ (58 mer Peptide)
NH₂-DGTPSY GHTPSH HAAQFP NHSFKH EDPMGQ QGSLGE

QQYSVP PPVYGC HTPTDS CTGS-COOH (SEQ ID NO: 7)
WT1₂₈₁₋₃₃₄ (54 mer Peptide)
NH₂-QALLLR TPYSSD NLYQMT SQLECM TWNQMN LGATLK

GVAAGS SSSVKW TEGQSN-COOH (SEQ ID NO: 8)
WT1₃₆₇₋₄₂₁ (55 mer Peptide)
NH₂-DVRRVP GVAPTL VRSASE TSEKRP FMCAYP GCNKRY

FKLSHL QMHSRK HTGEKPY-COOH
```

CEF Control Peptide Antigens

The CTL-CEF-Class I Peptide Library Pool contains 32 peptides, each corresponding to a defined HLA class I restricted T-cell epitope from Cytomegalovirus, Epstein-Ban virus and Influenza virus. The CEF antigen peptides are manufactured by Bio-Synthesis, Inc., Lewisville, Tex., to standards consistent with Phase 0

Guidelines, Catalog Number: 13686. The CTL-CEF-Class I Peptide Library Pool contains 32 peptides, each corresponding to a defined HLA class I restricted T-cell epitope from Cytomegalovirus, Epstein-Ban virus and Influenza virus. The lyophilized peptide pool is reconstituted with DMSO to 10 mM. The reconstituted peptide pool is aliquoted in cryovials, frozen and stored at −80° C. To manufacture DC vaccine batches an aliquot of the peptide is diluted to 2 mM with sterile water prior to use, i.e., 50 μL to 250 μL. The amino acid sequences of the CEF peptide antigens are listed in Table 1.

TABLE 1

CEF Peptide Antigens

| HLA Allele | Virus | Peptide Sequence | SEQ ID |
|---|---|---|---|
| A1 | Influenza A | NH$_2$-VSDGGPNLY-COOH | SEQ ID NO: 9 |
|  | Influenza A | NH$_2$-CTELKLSDY-COOH | SEQ ID NO: 10 |
| A2 | Influenza M | NH$_2$-GILGFVFTL-COOH | SEQ ID NO: 11 |
|  | Influenza A | NH$_2$-FMYSDFHFI-COOH | SEQ ID NO: 12 |
|  | EBV LMP2A | NH$_2$-CLGGLLTMV-COOH | SEQ ID NO: 13 |
|  | EBV BMLF1 | NH$_2$-GLCTLVAML-COOH | SEQ ID NO: 14 |
| A0201 | HCMV pp65 | NH$_2$-NLVPMVATV-COOH | SEQ ID NO: 15 |
| AA68 | Influenza NP | NH$_2$-KTGGPIYKR-COOH | SEQ ID NO: 16 |
|  | Influenza NP | NH$_2$-RVLSFIKGTK-COOH | SEQ ID NO: 17 |
|  | Influenza A | NH$_2$-ILRGSVAHK-COOH | SEQ ID NO: 18 |
|  | EBV | NH$_2$-RVRAYTYSK-COOH | SEQ ID NO: 19 |
|  | EBV | NH$_2$-RLRAEAQVK-COOH | SEQ ID NO: 20 |
| A3, A11, A60B1 | Influenza M | NH$_2$-SIIPSGPLK-COOH | SEQ ID NO: 21 |
| A11 | EBV EBNA 4NP | NH$_2$-AVFDRKSDAK-COOH | SEQ ID NO: 22 |
|  | EBV | NH$_2$-IVTDFSVIK-COOH | SEQ ID NO: 23 |
|  | EBV | NH$_2$-ATIGTAMYK-COOH | SEQ ID NO: 24 |
| A24 | EBV RTA | NH$_2$-DYCNVLNKEF-COOH | SEQ ID NO: 25 |
| B7 | Influenza NP | NH$_2$-LPFDKTTVM-COOH | SEQ ID NO: 26 |
|  | EBV | NH$_2$-RPPIFIRRL-COOH | SEQ ID NO: 27 |
| B8 | Influenza NP | NH$_2$-ELRSRYWAI-COOH | SEQ ID NO: 28 |
|  | EBV BZLF-1 | NH$_2$-RAKFKQLL-COOH | SEQ ID NO: 29 |
|  | EBV EBNA 3A | NH$_2$-FLRGRAYGL-COOH | SEQ ID NO: 30 |
|  | EBV EBNA 3 | NH$_2$-QAKWRLQTL-COOH | SEQ ID NO: 31 |
| B18 | HCMV | NH$_2$-SDEEEAIVAYTL-COOH | SEQ ID NO: 32 |
| B27 | Influenza NP | NH$_2$-SRYWAIRTR-COOH | SEQ ID NO: 33 |
|  | Influenza M | NH$_2$-ASCMGLIY-COOH | SEQ ID NO: 34 |
|  | EBV EBNA 3C | NH$_2$-RRIYDLIEL-COOH | SEQ ID NO: 35 |
| B35 | EBV EBNA3A | NH$_2$-YPLHEQHGM-COOH | SEQ ID NO: 36 |
|  | CMV pp65 | NH$_2$-IPSINVHHY-COOH | SEQ ID NO: 37 |
| B44 | EBV | NH$_2$-EENLLDFVRF-COOH | SEQ ID NO: 38 |
|  | HCMV | NH$_2$-EFFWDANDIY-COOH | SEQ ID NO: 39 |
| B0702 | HCMV | NH$_2$-TPRVTGGGAM-COON | SEQ ID NO: 40 |

Activation: The antigen-loaded DC will be activated for approximately 24 hours with a combination of LPS, CD40 and CL075.

Clinical Rationale: The safety and potential efficacy of LPS and LPS/CD40L activated DC vaccines has been established. Based on the activity of CL075 it is anticipated that DC vaccines activated with the agent will elicit stronger antigen-specific CD8+ T-cell responses in humans.

C. Intratumoral Injection

Treatment methods described herein involve administering antigen-loaded dendritic cells to a subject. The dendritic cells can be administered by various routes, including but not limited to subcutaneous, intratumoral, and intravenous administration routes.

Delivering active, antigen-loaded dendritic cells directly into tumor tissue can be particularly effective. Although it is generally believed that cytotoxic antineoplastic agents mediate their therapeutic effects in a cancer cell-autonomous fashion, recent results indicate that at least some chemotherapeutics inhibit tumor growth also indirectly, via the immune system. Indeed, it has been shown that a variety of transplantable or chemically induced primary mouse cancers respond more efficiently to anthracyclines when they develop in hosts carrying an intact immune system (reviewed in Kroemer, et al., 2013). Tumors evolving in immunodeficient mice fail to show a reduction in growth after anthracycline treatment in conditions in which the same tumors growing in immunocompetent mice do exhibit a significant inflection in their progression. Accordingly, clinical studies indicate that anthracycline-killed tumor cells are particularly efficient in stimulating a therapeutic immune response in cancer patients. Anthracycline-based neoadjuvant therapy of breast cancer patients is more effective when the tumor is infiltrated by T cells before chemotherapy is initiated as well as if chemotherapy causes a significant influx of CD8+ T cells into the tumor bed and/or reduces the presence of immunosuppressive T regulatory (Treg) cells (reviewed in Kroemer, et al., 2013). The reason why anthracyclines provoke this complex anticancer immune response has only been partially elucidated. In contrast to many other cytotoxic chemotherapeutics, anthracyclines stimulate immunogenic cell death that is characterized by a compendium of subtle biochemical changes in the plasma membrane surface and in the microenvironment of dying cancer cells. These changes include the pre-apoptotic exposure of calreticulin on the plasma membrane surface (to facilitate the engulfment of portions of the dying cells by antigen-presenting cells, APC) and the post-apoptotic exodus of high mobility group B1 (HMGB1) from the nucleus (to engage with TLR4 receptors and to stimulate antigen presentation) (reviewed in Kroemer, et al., 2013). Moreover, ATP release by autophagy-competent dying tumor cells (positive for LC3-II) is essential for the induction of an anticancer immune response, both by stimulating the recruitment of inflammatory cells ($CD11b^+LyC6^{high}$ $CD11c^{low}$ CD86+) into the tumor bed and by ligating P2RX7 receptors on dendritic cells, hence facilitating the activation of the NLRP3 inflammasome and the consequent secretion of IL-1β by APC (reviewed in Kroemer, et al., 2013).

How chemotherapy-induced cell death leads to efficient antigen presentation to T cells has remained an open conundrum. It has been shown in mice that intratumoral $CD11c^+$ $CD11b^+Ly6C^{high}$ cells, which shared some characteristics of inflammatory dendritic cells (DC) and contained granulomonocytic precursors, were crucial for the induction of anticancer immunity post-chemotherapy (Ma, et al., 2013). First, ATP released by dying tumor cells is essential for the recruitment of myeloid cells into tumor beds and for the local differentiation of inflammatory DC. Second, manipulations aimed at avoiding the intratumoral accumulation of these $CD11c^+CD11b^+Ly6C^{high}$ cells, such as local overexpression of the ATP-degrading enzyme CD39, pharmacological blockade of purinergic receptors, or neutralization of CD11b, abolished the immune-dependent inhibition of tumor growth by anthracyclines. Third, $CD11c^+CD11b^+$ $Ly6C^{high}$ were efficient in capturing and presenting tumor cell antigen to T cells and protected mice upon their adoptive transfer against challenge with cancer cells. Altogether, the results identify a population of tumor-infiltrating leukocytes as therapy-relevant antigen-presenting cells.

The two immunogenic cell death markers HMGB1 and LC3-II were evaluated on paraffin-embedded BC specimens in a test (50 early BC treated with adjuvant anthracyclines that relapse at 3 years paired with 50 cases that were disease-free at 10 years) and a validation cohort on 150 Her2 negative early BC treated with adjuvant anthracyclines. Preliminary data suggest that LC-3-II staining was negative in the vast majority of cases of early breast cancers (>70%). These "autophagy deficient" cancers are also less infiltrated with CD8+ T cells but contained more CD68+ cells and had a greater chance of recurrence following adjuvant chemotherapy. A larger across Europe validation study is ongoing.

Blocking ectoATPases (CD39) restored the recruitment of DC in tumors and the efficacy of chemotherapy in autophagy deficient murine cancers (Michaud, et al., 2011). However, anti-CD39 Ab are not available for use in the human at this time. We propose to substitute the functional DCs via adoptive transfer of ex vivo generated autologous mature DCs injected locally into LA TNBCs at 48 hours post-systemic anthracyclines. Whereas we will not stratify in this early phase of DC vaccine assessment, all samples will be tested for LC3-II staining (and others such as CD68, CD8, Foxp3, phosphoSTAT6).

Another objective for intra-tumoral vaccination is the possibility to enhance the access of DCs to draining lymph nodes. Indeed, recent studies suggest that the route of DC injection might determine the homing of elicited T cells. Indeed, for mucosal cancer vaccines, the homing to and retention of CD8+ T cells in the mucosa are critical for efficacy (Sandoval, et al., 2013). In this context, the growth of orthotopic head and neck or lung cancers can be inhibited by a cancer vaccine provided that it is administered by the intranasal mucosal route, but not the intramuscular route. This is explained by the induction through intranasal vaccination of mucosal CD8+ T cells expressing the mucosal integrin CD49a, the expression of which is essential for the efficacy of cancer vaccines.

D. Cyclin B1 Antigen

In some embodiments, the dendritic cell vaccines disclosed herein are loaded with cyclin B1 peptide antigens. Cyclin B1 is also known as CCNB1, CCNB, CCNB1, G2 mitotic specific cyclin B1, and G2/mitotic-specific cyclin-B1. The cyclin B1 peptide antigens can comprise the full length cyclin B1 sequence. The cyclin B1 peptide antigens can also comprise shorter immunogenic peptide fragments. Upon loading with cyclin B1 peptide antigens, the dendritic cells process the peptides into smaller fragments and present them on the cell surface in complex with MHC class II molecules. Antigen-loaded dendritic cells can then be activated and administered to a patient to induce an immune response.

Transcriptional profiling of triple negative breast cancers demonstrates a very strong proliferation signature (Schneider, et al., 2008; Sorlie, et al., 2001) including enhanced transcription of cyclin B1. Cytoplasmic accumulation of cyclin B1 has been identified as an early event in breast cancer development (Kao, et al., 2001) Furthermore, cyclin B1 genes are among the transcripts analyzed in the 21-gene assay Oncotype Dx, the first clinically validated multigene assay that quantifies the likelihood of breast cancer recurrence (Strayer, et al., 2010).

Cyclin B1 is a regulatory protein that is an essential component of the mitotic cell cycle. The natural peak of cyclin B1 occurs between the G2-M phases of the cell cycle, and is reduced to near zero afterwards. However, in cancer cells, this protein is over-expressed during all phases of the cell cycle. Additionally, cyclin B1 is found in normal cells in the nucleus, whereas in cancer cells it is found in the cytoplasm (Egloff, et al., 2006). Several studies have shown that inactivation of the tumor suppressor gene p53, which occurs in all triple negative breast cancers, directly contributes to the aberrant regulation of cyclin B1 in tumor cells (Yu, et al., 2002). Cyclin B1 has been found to be over-expressed in multiple forms of cancer, including breast cancer, and in most cancer cell lines (Egloff, et al., 2006). While studies involving the immunogenicity of cyclin B1 are limited, there are some indications that it is an important antigen to pursue (Yu, et al., 2002). Cyclin B1-specific antibodies are found in the blood of patients with many cancer types, at both the premalignant and established phases (Suzuki, et al., 2005). Cyclin B1-specific T cells can be also found in healthy volunteers (Neidhardt-Berard, et al., 2004). Both antibodies and T cells against cyclin B1 protect from cancer in mouse models (Neidhardt-Berard, et al., 2004). Because cyclin B1 is necessary for cancer cell division, loss of the antigen is an unlikely means of tumor escape.

It has been shown that DCs loaded with killed breast cancer cells expressing cyclin B1 induce differentiation of cyclin B1-specific T cells, and that these T cells are able to kill breast cancer tumors in vitro (Neidhard-Berard, et al., 2004; Saito, et al., 2006). In preliminary studies preparatory to the clinical trial proposed herein, it was also found that patients with various breast cancer subtypes can display a cyclin B1-specific memory T cell repertoire in their blood. These observations further support the targeting of this antigen for breast cancer immunotherapy. In the study described herein, LA TNBC patients will be immunized with cyclin B1 peptide-loaded DC vaccines, along with standard preoperative chemotherapy.

In some embodiments of the methods described herein, the following cyclin B1 peptides will be incubated with DCs under conditions that cause cyclin B1 peptide epitopes to be displayed on the surface of DCs:

```
Cyclin B1₂₀₇₋₂₄₂ (36 mer Peptide)
                                          (SEQ ID NO: 1)
NH₂-DWLVQV QMKFRL LQETMY MTVSII DRFMQN NCVPKK-COOH Cyclin B1₂₈₅₋₃₃₄ (50 mer Peptide)
                                          (SEQ ID NO: 2)
NH₂-MEMKIL RALNFG LGRPLP LHFLRR ASKIGE VDVEQH

TLAKYL MELTML DY-COOH
```

E. Wilms Tumor Antigen (WT-1)

In some embodiments, the dendritic cell vaccines disclosed herein are loaded with WT-1 peptide antigens. The WT-1 peptide antigens can comprise the full-length WT-1 sequence. The WT-1 peptide antigens can also comprise shorter immunogenic peptide fragments. Upon loading with WT-1 peptide antigens, the dendritic cells process the peptides into smaller fragments and present them on the cell surface in complex with MHC class II molecules. Antigen-loaded dendritic cells can then be activated and administered to a patient to induce an immune response.

The zinc finger transcription factor WT-1 is expressed at 10-1000× fold higher levels in leukemic cells compared to normal CD34+ cells, and the magnitude of expression correlates with clinical aggressiveness of acute myeloid leukemia (AML), myelodysplastic syndromes (MDS), and acute lymphoid leukemia (ALL) (Chapuis, et al., 2013). Although essential during embryogenesis, WT-1 expression after birth is limited to low levels predominantly in kidney podocytes and CD34+ hematopoietic stem cells (HSC). WT-1-specific CD8+ T lymphocytes can distinguish over-expressing targets from normal cells and have been demonstrated to inhibit the growth of and to lyse leukemic but not normal CD34+ cells. Recent whole genome and transcriptome sequencing analysis of metastatic tumor tissue obtained from 14 TNBC patients, has delineated the wide array of somatic genomic alterations in these advanced tumors. Genes mutated in multiple tumors included TP53, LRP1B, HERC1, CDH5, RB1, and NF1. WT-1 was among the genes that contained focal structural mutations as were CTNNA1, PTEN, FBXW7, BRCA2, FGFR1, KRAS, HRAS, ARAF, BRAF, and PGCP. Furthermore, WT-1 was found to be overexpressed on RNA sequencing in all 14 samples (Craig, et al., 2013). Furthermore, the analysis of public microarray datasets of 266 early breast cancer patients showed that WT-1 mRNA expression was correlated with higher histological grades, ER-negative and basal-like and ERBB2 molecular breast cancer subtypes (Qi, et al., 2012). Disease-free survival analysis showed worse prognosis the WT-1 high expression group, and WT-1 was found to be an independent prognostic indicator in multivariate analysis. Finally, WT-1 promotes proliferation and oncogenicity, and loss of expression is disadvantageous for the tumor, making outgrowth of antigen-loss variants less likely.

In some embodiments of the methods described herein, the following WT-1 peptides will be incubated with DCs under conditions that cause WT-1 peptide epitopes to be displayed on the surface of DCs:

```
                                          (SEQ ID NO: 3)
WT1₆₁₋₁₁₄ (54 mer Peptide)
NH2-ASGSEP QQMGSD VRDLNA LLPAVP SLGGGG GCALPV

SGAAQW APVLDF APPGAS-COOH (SEQ ID NO: 4)
WT1₁₁₅₋₁₇₄ (60 mer Peptide)
NH2-AYGSLG GPAPPP APPPPP PPPPHS FIKQEP SWGGAE

PHEEQC LSAFTV HFSGQF TGTAGA-COOH (SEQ ID NO: 5)
WT1₁₇₅₋₂₂₂ (48 mer Peptide)
NH2-CRYGPF GPPPPS QASSGQ ARMFPN APYLPS CLESQP

AIRNQG YSTVTF-COOH (SEQ ID NO: 6)
WT1₂₂₃₋₂₈₀ (58 mer Peptide)
NH2-DGTPSY GHTPSH HAAQFP NHSFKH EDPMGQ QGSLGE

QQYSVP PPVYGC HTPTDS CTGS-COOH (SEQ ID NO: 7)
WT1₂₈₁₋₃₃₄ (54 mer Peptide)
NH2-QALLLR TPYSSD NLYQMT SQLECM TWNQMN LGATLK

GVAAGS SSSVKW TEGQSN-COOH (SEQ ID NO: 8)
WT1₃₆₇₋₄₂₁ (55 mer Peptide)
NH2-DVRRVP GVAPTL VRSASE TSEKRP FMCAYP GCNKRY

FKLSHL QMHSRK HTGEKPY-COOH
```

F. Cancer Chemotherapy

In some embodiments, treatment methods described herein involve administration of antigen-loaded dendritic cells in combination with chemotherapy. Administration of antigen-loaded dendritic cells can be performed before, during, or after chemotherapy to help improve outcomes for subjects with cancer. Embodiments described herein also involve administering chemotherapy in combination with anakinra without administration of dendritic cell vaccines.

Adjuvant chemotherapy can substantially reduce the risk of breast cancer recurrence and death in high-risk patients (Early Breast Cancer Trialists' Collaborative Group, 1998), and there are many chemotherapy regimens with established efficacy and safety data. The value of chemotherapy is established from the data from individual randomized trials and from the Early Breast Cancer Trialists' Collaborative Group's (EBCTCG) 15-year meta-analyses of randomized chemotherapy trials (Early Break Cancer Trialists' Collaborative Group's, 2005). The meta-analyses established that anthracycline-containing therapies, such as doxorubicin and cyclophosphamide (AC) and docetaxel, doxorubicin, and cyclophosphamide (TAC), offer superior efficacy, reducing the risk of recurrence by 11% and the risk of death by 16% compared with cyclophosphamide, methotrexate, and fluorouracil (CMF) combinations (Early Break Cancer Trialists' Collaborative Group's, 2005).

Significant improvements in disease-free survival (DFS) were reported with adjuvant dose-dense chemotherapy in women with node-positive breast cancer in the Phase III CALGB9741 study of 2005 women. Citron et al., 2003 showed that when the taxane, paclitaxel (Taxol) (T), was given sequentially following standard chemotherapy, doxorubicin (A) and cyclophosphamide (C), in an every two-weekly dose-dense regimen, the rate of recurrence was significantly reduced by 26% (P=0.010) and the rate of death was reduced by 31% (P=0.014), compared to standard every 3-week administration, with an acceptable toxicity profile.

In a 2005 report of the findings of NSABP B-28, the addition of a taxane, adjuvant paclitaxel, to AC resulted in significant improvement in DFS. NSABP B-28 was conducted to determine whether 4 cycles of adjuvant T after 4 cycles of adjuvant AC (AC→T) would increase the DFS and OS compared with 4 cycles of AC alone in patients with resected operable, node-positive breast cancer (Mamounas, et al., 2005). Patients (N=3060) were randomly assigned to the 2 groups. The addition of AC→T significantly reduced the hazard for developing a DFS event by 17% (relative risk [RR], 0.83; 95% CI, 0.72 to 0.95; P=0.006). Five-year DFS was 76%±2% for patients randomly assigned to AC→T compared with 72%±2% for those randomly assigned to AC. Improvement in OS was small and not statistically significant (RR, 0.93; 95% CI, 0.78 to 1.12; P=0.46). Five-year OS was 85%±2% for both groups. Toxicity with the AC→T regimen was found to be acceptable in the adjuvant setting.

Thus, the combination of AC, followed by a taxane such as paclitaxel (Taxol) is now widely accepted as an effective adjuvant treatment for early-stage breast cancer.

Advances in adjuvant chemotherapy have resulted in improved outcomes in patients with ER-breast cancers to a greater extent than for those with ER+ breast cancers (Berry, et al., 2006). Many of these have been implemented as neoadjuvant therapy. Standard AC→T given preoperatively to TNBC patients results in pathologic complete response rates of 30%-40% (Von Minckwitz, et al., 2011; Carey, et al., 2007).

Other conventional cancer therapies and treatments may also be administered in combination with the DC vaccines described herein. Cancer treatments that may be administered may include surgery and/or radiation. Conventional cancer therapies may also include one or more chemotherapeutics, including but not limited to cisplatin (CDDP), carboplatin, procarbazine, mechlorethamine, camptothecin, ifosfamide, melphalan, chlorambucil, busulfan, nitrosurea, dactinomycin, daunorubicin, bleomycin, plicomycin, mitomycin, etoposide (VP 16), tamoxifen, raloxifene, estrogen receptor binding agents, gemcitabine, navelbine, farnesyl-protein transferase inhibitors, transplatinum, 5-fluorouracil, vincristin, vinblastin and methotrexate, or any analog or derivative variant of the foregoing.

Other suitable therapeutic agents may also include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Therapeutic agents administered in the methods described herein may also include those that are well known for use against breast cancer. These breast cancer chemotherapeutics may include capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, and vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thio-colchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a premixed single composition. The composition may or may not contain an Hsp90 inhibitor. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol).

In some embodiments, chemotherapeutic agents can be administered in combination with anakinra and without administration of dendritic cell vaccines. In some embodiments, the chemotherapeutic agent that is administered is combination with anakinra is one of Nab paclitaxel, eribulin, capecitabine, or vinorelbine. In some embodiments, the doses to be used for chemotherapeutic drug products may be as set forth below:

Nab paclitaxel: 100 mg/m$^2$ administered IV weekly (Day 1, 8, and 15 every 28 days)

Eribulin: 1.4 mg/m$^2$ administered IV weekly (Day 1 and 8 every 21 days)

Capecitabine: physician's choice of utilizing 1000 mg/m$^2$ BID 14 days on, 7 days off OR 1000 mg/m$^2$ BID 7 days on, 7 days off (capecitabine is rounded to the nearest 500 mg increment).

Vinorelbine: 25 mg/m$^2$ administered IV weekly (Day 1, 8, and 15 every 28 days).

G. Decreasing iT$_H$2 Cell-Mediated Cancer Inflammation

In some embodiments, the treatment methods described herein include administration of therapeutic agents that block pro-inflammatory pathways that are responsible for chronic inflammation in many solid tumors. Such therapeutic agents may include antagonists of IL-1R, including but not limited to anakinra. In some embodiments, anakinra may be used in combination with chemotherapy and DC vaccines. In some embodiments, anakinra is used in combination with chemotherapy alone.

Solid tumors are often associated with chronic inflammation that promotes cancer cell survival and metastasis. Linked closely with this is the significant presence of macrophages, educated by type 2 cytokines IL-4 and IL-13. Recent studies have demonstrated a significant presence of inflammatory CD4+ T cells (iTH2) cells in breast cancer, which produce high levels of IL-13, IL-4, and tumor necrosis factor. These iTH2 cells accelerate breast cancer development in xenograft models through production of IL-13, whereas in murine models, they accelerate metastases by production of IL-4. iTH2 cells are driven by OX40L+ tumor infiltrating myeloid DCs (mDCs) which are conditioned by thymic stromal lymphopoietin (TSLP) secreted by malignant cells and infiltrating stromal cells. TSLP-neutralizing antibodies block upregulation of OX40L by tumor-infiltrating mDCs, and consequently block mDCs' capacity to generate iTH2 cells and to accelerate tumor development in vivo (Coussens, et al., 2013). Thus, interference with the TSLP-OX40L-IL-13 axis will allow modification of cancer-associated inflammation and thereby offer a novel therapeutic approach for patients with TNBC.

Recent studies show that TSLP secretion from breast cancer cells is regulated by IL-1β. Results showed high levels of IL-1β in the breast cancer microenvironment. IL-1β induces TSLP production from breast cancer cell lines in a dose and contact dependent manner. Cancer cells induce IL-1β secretion from DCs and monocytes in a contact-dependent fashion. This is mediated by cancer cell-derived TGF-β. Administration of the IL-1R antagonist, anakinra, prevents tumor growth in vivo, blocks OX40L+ expression on DCs, and blocks iTH2 generation in vivo. Clinically, the Th2 signature in breast cancer (Teschendorff, et al., 2010; Kristensen, et al., 2012) is associated with poor outcomes. IL-4 and IL-13 exert pro-tumor activity through several pathways including: 1) the triggering of TGF-β secretion (Terabe, et al., 2004); 2) the upregulation of anti-apoptotic pathways in cancer cells (Zhang, et al., 2008); and 3) the generation of type-2 polarized macrophages that foster tumor growth directly, via secretion of growth factors, and indirectly via inhibitory effects on CD8+ T cell function (DeNardo, et al., 2011). Indeed, CD8+ T cells are essential for tumor rejection through the generation of cytotoxic effectors. The presence of CD8+ T cells in primary tumors is associated with the long-term survival of patients with colorectal and breast cancer (DeNardo, et al., 2011; Galon, et al., 2006). Thus, iTH2 cells have a broad and profound impact on tumor microenvironment and tumor development.

Thus blockade of IL-1β represents a novel approach to breast cancer immunotherapy. In some embodiments of the methods described herein, a therapeutic agent that blocks the IL-1 inflammatory pathway is administered to a breast cancer patient in combination with chemotherapy and/or dendritic cell vaccines. In some embodiments, such therapeutic agents include but are not limited to anakinra, rilonacept, and canakinumab. (Jurrmann et al., 2009). Rilonacept is a recombinant IL-1 receptor-IG fusion protein and is generally administered in a loading dose of 320 mg followed by 160 mg weekly doses. Canakinumab is a humanized anti IL-1β antibody and is generally administered in a dose of 150 mg subcutaneaously every 8 weeks. Agents that block the IL-1 inflammation pathway are also described in Symons et al, 1995, Petrasek et al., 2012, Economides et al., 2003, and Jurrmann et al., 2005. Agents that block the IL-1 inflammation pathway may include modifiers of IL-1β gene transcription, modifiers of IL-1β gene translation, siRNAs that reduce expression of IL-1β, and antagonists of IL-1 receptor.

Anakinra is a recombinant soluble non-glycosylated homolog of the human interleukin-1 receptor antagonist (IL-1Ra) that competitively inhibits binding of IL-1α and IL-1β to the receptor type I. Anakinra was approved in 2001 as a treatment for patients with adult rheumatoid arthritis whose disease has progressed through one or more disease-modifying anti-rheumatic drugs. Anakinra is an effective treatment for systemic onset juvenile arthritis, an IL-1-driven disease (Pascual et al., 2005). Resolution of clinical symptoms including fever, marked leukocytosis, thrombocytosis, anemia, elevated ESR and arthritis were rapid and sustained (Pascual et al., 2005). These results have now been confirmed in randomized clinical trials. A pilot safety trial administering anakinra in combination with the physician's choice of nab paclitaxel, capecitabine, eribulin, and vinorelbine was recently opened in patients with metastatic breast cancer at Baylor Sammons Cancer Center. This study will evaluate the effects of anakinra on the IL-1-driven immunologic effects on patients' T cell subsets and on a peripheral blood IL-1 signature signifying adverse IL-1-mediated immunologic effects that has been developed at BIIR. Anakinra has a favorable safety profile; the most common adverse reaction is an injection site reaction.

H. Combination Therapies

In some embodiments, the treatment methods described herein include two or more therapeutic agents administered in combination. For example, antigen-loaded dendritic cells may be administered in combination with chemotherapy, anakinra, or both. Administration of DC vaccines may also be combined with radiation and/or surgery. Combination therapy may involve administering different therapeutic agents or treatments at the same time or within a period of time wherein separate administration of the therapeutic agents or treatments produces a desired therapeutic benefit. This may be achieved by administering a single pharmacological formulation that includes two or more therapeutic agents, or by administering two or more distinct compositions or formulations, wherein one composition includes one therapeutic agent and the other includes another.

The therapeutic agents and treatments disclosed herein may precede, be co-current with and/or follow another treatment or agent by intervals ranging from minutes to weeks. In embodiments where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

Various combination regimens of the therapeutic agents and treatments may be employed. Non-limiting examples of such combinations are shown below, wherein a therapeutic agent such as a DC vaccine disclosed herein is "A" and a second agent, such as an anti-cancer chemotherapeutic, is "B":

| A/B/A | B/A/B | B/B/A | A/A/B | A/B/B | B/A/A | A/B/B/B | B/A/B/B |
| B/B/B/A | | B/B/A/B | A/A/B/B | A/B/A/B | A/B/B/A | B/B/A/A | |
| B/A/B/A | | B/A/A/B | A/A/A/B | B/A/A/A | A/B/A/A | A/A/B/A | |

In some embodiments, more than one course of therapy may be employed. It is contemplated that multiple courses may be implemented.

F. EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1: Prophetic Example

Blocking IL-1B to Reduce Pro-Cancer Inflammation

TSLP secretion from breast cancer cells is regulated by IL-1β. Results showed high levels of IL-1β in the breast cancer microenvironment. IL-1β induces TSLP production from breast cancer cells lines in a dose and contact dependent manner. Cancer cells induce IL-1β secretion from DCs and monocytes in a contact-dependent fashion. This is mediated by cancer cell-derived TGF-β. Administration of the IL-1R antagonist, anakinra, prevents tumor growth in vivo, blocks OX40L+ expression on DCs, and blocks $iT_H2$ generation in vivo. Clinically, the Th2 signature in breast cancer (Teschendorff, et al., 2010; Kristensen, et al., 2012) is associated with poor outcomes. IL-4 and IL-13 exert pro-tumor activity through several pathways including: 1) the triggering of TGF-β secretion (Terabe & Berzofsky, et al., 2004); 2) the upregulation of anti-apoptotic pathways in cancer cells (Zhang, et al., 2008); and 3) the generation of type-2 polarized macrophages that foster tumor growth directly, via secretion of growth factors, and indirectly via inhibitory effects on CD8+ T cell function (DeNardo, et al., 2011). Indeed, CD8+ T cells are essential for tumor rejection through the generation of cytotoxic effectors. The presence of CD8+ T cells in primary tumors is associated with the long-term survival of patients with colorectal and breast cancer (DeNardo, et al., 2011; Galon, et al., 2006). Thus, $iT_H2$ cells have a broad and profound impact on tumor microenvironment and tumor development.

Thus blockade of IL-1β represents a novel approach to breast cancer immunotherapy. Anakinra is a recombinant soluble non-glycosylated homolog of the human interleukin-1 receptor antagonist (IL-1Ra) that competitively inhibits binding of IL-1α and IL-1β to the receptor type I. The study described herein will evaluate the effects of anakinra on the IL-1-driven immunologic effects on patients' T cell subsets and on a peripheral blood IL-1 signature signifying adverse IL-1-mediated immunologic effects that has been developed at BIIR. Anakinra has a favorable safety profile; the most common adverse reaction is an injection site reaction.

Example 2: Prophetic Example

Clinical Trial of Dendritic Cell Vaccine Loaded with Cyclin B1 and WT-1 Antigens Administered in Combination with Chemotherapy and Anakinra 1. Study Overview and Objectives The goals of the study are to boost T cell immunity targeted against breast cancer utilizing a tumor antigen-loaded DC vaccine, to reverse the immune suppressive tumor microenvironment by IL-1 blockade, to enhance chemotherapy effectiveness and decrease tumor metastagenicity, and to decrease the recurrence rates of LA TNBC. Patients with LA TNBC will be treated with a combination of antigen-loaded DC vaccinations along with standard preoperative chemotherapy, to improve TNBC immunogenicity and to increase the pCR rate achieved with standard therapy. The trial will consist of 2 patient cohorts. In the first group, patients will receive DC vaccinations in combination with preoperative chemotherapy. In the second group, IL-1 blockade with anakinra will be added to the preoperative chemotherapy and DC vaccine.

The primary objective of this study is to determine the safety and feasibility of combining cyclin B1/WT-1/CEF (antigen)-loaded DC vaccination with preoperative chemotherapy, and to combine DC vaccination with preoperative chemotherapy in addition to IL-1 blockade with anakinra in patients with LA TNBC.

The secondary objectives of this trial are to determine pathologic complete response rates, with and without anakinra; disease-free survival; to assess immune biomarkers of immunity (antigen-specific CD8+ T cell immunity and $T_H2$ T cells) in breast cancer biopsy specimens and blood samples in patients receiving DC vaccinations, with and without IL-1 blockade with anakinra; and to assess the feasibility of immunizing LA TNBC patients with patient-specific tumor antigens.

This exploratory pilot safety, open label trial will evaluate the combination of preoperative chemotherapy and Dendritic Cell (DC) vaccinations in 2 groups of patients with LA TNBC. A summary of the study design is shown in FIG. 1. The first 10 patients will be enrolled to receive DC vaccinations during the 16 weeks of standard preoperative dose-dense doxorubicin/cyclophosphamide followed by paclitaxel chemotherapy; the following 10 patients will be a staggered enrollment, and will receive DC vaccinations and anakinra 100 mg SC for 7 days, followed by 7 days off, then repeating, during the 16 weeks of preoperative chemotherapy. Enrollment in Group 1 will complete before enrollment can begin in Group 2. For Group 2, there will be a staggered enrollment, in order to observe the safety of AC/T chemotherapy, DC vaccinations, and anakinra. After the first 3 patients have been enrolled in Group 2, enrollment will be held for observation of these patients for the 4 months of AC/T chemotherapy plus anakinra plus DC vaccine for adverse events, prior to enrolling a second set of 3 patients. Observation of these next 3 patients will occur over the 4 months of AC/T, anakinra, and DC vaccine for toxicity prior to completing enrollment of the last 4 patients in Group 2. Study procedures will be similar in both groups. Patients may only participate in one group of the study.

The screening period is from signature of the informed consent form to final eligibility assessments. Eligible patients will undergo apheresis after registration and entry into the study. After collection of peripheral blood mononuclear cells, dendritic cell will be manufactured from the monocyte fraction, aliquoted and frozen. Patients will be given a total of 7 DC vaccinations.

Patients will undergo research biopsies of their breast cancer prior to the start of treatment and 1-2 days prior to or on Day 1 of Cycle 3 of AC to analyze the composition of the immune microenvironment. Four to 5 core biopsies will be obtained prior to treatment initiation for whole exome sequencing and expression analysis and for characterization of the tumor immune microenvironment.

Patients will receive standard preoperative dose-dense doxorubicin/cyclophosphamide (4 cycles) followed by paclitaxel (4 cycles; AC/T) chemotherapy, administered every 2 weeks for 16 weeks combined with antigen-loaded DC vaccinations administered intratumoral (one injection of 0.2 mL at $3 \times 10^6$ cells/mL) and subcutaneous (one injection of 1 mL at $15 \times 10^6$ DCs) on any one individual day between Days 9-12 of Cycles 1 and 3 of dose-dense AC and on any one individual day between Days 9-12 of Cycles 1 and 3 of T (4 timepoints). Timing of the vaccinations is based on data that tumor cell death associated with doxorubicin treatment increases the generation and functional activation of $CD8^+$ T cells required for the antitumor activity of doxorubicin (Mattarollo, 2011). Standard pegfilgrastim support will be given on Day 2 of each AC treatment.

After preoperative treatment, patients will undergo definitive surgery, generally with mastectomy, and if available, the residual FFPE breast cancer tissue will be collected for assessment of the immune microenvironment and for whole exome sequencing to identify cancer-associated mutations in the residual, chemotherapy-refractory cancer. Patients will be known to have axillary node positive disease at study entry based on biopsy or clinical criteria and will generally undergo level 1/2 axillary dissection at definitive surgery. However, patients may undergo SLN biopsy before or after AC/T therapy at the physician's discretion.

After definitive surgery and during locoregional radiation therapy to the breast or chest wall and regional lymphatics per standard of care, patients will receive 3 boost DC vaccinations subcutaneously of 1 mL (at $15 \times 10^6$ cells/mL) in the ventral surface of the upper arm, with antigen-loaded DCs. The first vaccination booster will occur once after the surgery and up to 3 days prior to radiation; the second booster will occur 30 days±3 days after radiation is completed; and the third booster will occur 90 days±3 days after the 2nd boost.

Blood samples for immunomonitoring studies will be obtained at baseline, prior to each DC vaccination, prior to surgery, prior to radiation, and 2 weeks after the last DC vaccination.

2. DC Vaccine Preparation

A. Manufacturing Process

Figure 3:
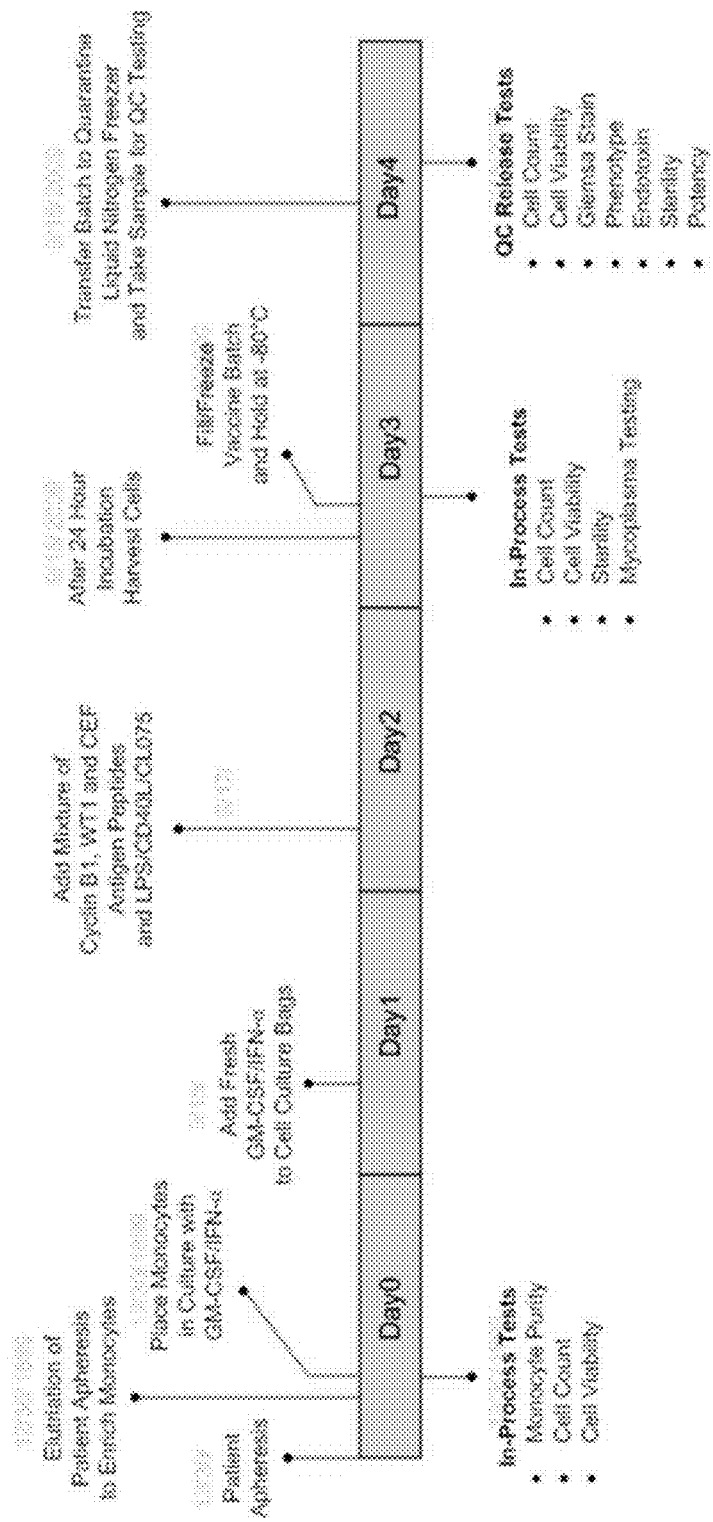
FIG. 3—Overview of the BIIR-BrcaVax-001 DC vaccine manufacturing process.

Following is the detailed description of the manufacturing process and equipment used to prepare the patient's frozen batch of BIIR-BrcaVax-001 autologous DC vaccine product. FIG. 3 shows an overview of the manufacturing process.

Preparation of Monocytes for Initiating the DC Culture.

The following steps are taken to enrich the peripheral blood monocytes to prepare the patient's frozen DC vaccine batch. The first step is the collection of peripheral blood mononuclear cells (PBMC) from the patient by apheresis (see below). The second step is to enrich the monocytes from the patient's apheresis by elutriation employing the Terumo BCT Elutra®. The Elutra® is a semi-automatic, closed system centrifuge that uses continuous counter-flow elutriation technology to separate cells into multiple fractions based on size and density. The elutriation procedure is outlined in the Elutra® operator's manual. The elutriation process begins by installing a sterile, disposable tubing set on the Elutra®, and then priming the system with HBSS supplemented with Human Serum Albumin. Once the Elutra® is primed, the apheresis bag containing the patient's PBMC is sterile connected to the disposable tubing set and the elutriation program is started. A sterile, heat-activated tubing welder (Terumo) is used to make the cuts and seals to connect the tubing used throughout the entire monocyte preparation and DC vaccine manufacture process to maintain sterility. The Elutra® system automatically collects 5 fractions of cells based on size and density. Elutriation Fraction 5 normally contains the enriched monocyte population. The Coulter AcT5 automated hematology analyzer is employed to determine the purity of the Fraction 5 monocytes before they are used for preparation of the patient's frozen DC vaccine batch. Based on the aphereses collected from 41 patients with malignant melanoma (BB-IND 12919) the expectation is that the median monocyte purity in elutriation Fraction 5 is 92.4% (range 41.0% to 96.6%; average±std dev of 86.7±13.2%). Other cell types found in Fraction 5 from this particular group of 41 patients with malignant melanoma included: neutrophils (average±std dev of 5.3±8.5%), lymphocytes (average±std dev of 5.5±6.1%), eosinophils (average±std dev of 0.2±0.3%) and basophils (average±std dev of 1.3±0.5%). On occasion, depending on the yield and purity of the patient's cells, the enriched monocytes are found in elutriation Fraction 4. In these instances either Fraction 4, Fraction 5 or the combined Fractions 4 and 5 are used to prepare the patient's frozen DC vaccine batch. Once determined, the elutriation bag containing the enriched monocyte population is centrifuged to pellet the cells. After centrifugation the supernatant is removed from the bag and the cells are resuspended in CellGro® DC culture medium. A sample is removed from the cell suspension for in-process QC testing to determine the cell count and viability in order to fill the cell culture bags at the specified cell density for initiation of the DC culture.

Method of Monocyte Collection.

For the proposed clinical trial the patient apheresis is performed at the Baylor University Medical Center (BUMC) Apheresis Collection Center, Dallas, Tex., using the COBE SPECTRA™ system. The settings used for operation of the COBE SPECTRA™ system used by the BUMC Apheresis Collection Center have been worked out in collaboration with GAMBRO the manufacturer of the apheresis system. Furthermore, the apheresis procedure conducted at the BUMC Apheresis Collection Center has provided consistent product for preparation of DC vaccines manufactured by the BIIR for conducting various cancer and infectious disease clinical trials.

Culture Conditions for DC Vaccine Manufacture.

The steps in the DC vaccine manufacturing process are outlined below. The first step is to establish the monocytes in cell culture to induce differentiation of the DC. To establish the cell culture (Day 0) elutriation enriched monocytes are suspended at $1\times10^6$ viable cells/mL in CellGro® DC culture media supplemented with GM-CSF at 100 ng/mL and IFN-α at 500 IU/mL. The transfer pack (Baxter Fenwal, 4R 2041) containing the cell suspension is then sequentially attached to individual cell culture bags (AFC, 118AC) and 100 mL of the cell suspension is transferred to each bag. The cell culture bags are then placed in a 37° C., 5% $CO_2$ incubator. After 24 hours of cell culture (Day 1) the media is replenished with fresh GM-CSF at 100 ng/mL and IFN-α at 500 IU/mL in 5 mL of CellGro DC media per culture bag by using sterile syringes with 19G×1½ inch needles to inject the cytokines and media into the cell culture bags. The second step is to load the differentiated DC with tumor and control antigens, that is, CEF control antigens is a mixture of infectious virus antigen peptides, WT1 is a mixture of 6 Wilm's Tumor antigen peptides and Cyclin B1 are two long antigen peptides. The antigen loading is performed after the cells have been cultured for approximately 48 hours (Day 2). To load the DC with the antigen peptides a 1 mL syringe with 19G×1½ needle is used to add 1.0 µL of the peptide mixture per mL of cell culture media to achieve 2-3 µM of each of the antigen peptides. CEF antigen peptides is added to one of the cell culture bags and WT1 and Cyclin B1 antigen peptides are added to half of the remaining cell culture bags, respectively. The third step is to activate the antigen loaded DC with LPS, CD40L and CL075. On Day 2, immediately after adding the antigen peptides to the DC, 1 mL syringes with 19G×1½ inch needles are used to add 5 EU/mL of LPS, 100 ng/mL of CD40L and 1.0 µg/mL of CL075 to each of the cell culture bags. The DC are cultured for 24±1 hours with the peptide antigens and LPS/CD40L/CL075 before they are harvested for fill/freezing of the DC vaccine. Prior to DC harvest a 6 mL sample of the cell culture media is collected from 6 randomly selected cell culture bags. The samples are pooled and then submitted for in-process testing for the possibility of bacterial, fungal and *mycoplasma* contamination. After removing the sample for in-process sterility and *mycoplasma* testing, the contents of the cell culture bags are then transferred into 600 mL transfer packs (Baxter Fenwal, 4R 2023). The contents of approximately 4 culture bags is transferred to each transfer pack. By centrifugation (770×g for 10 minutes) the cells are pelleted, combined and transferred to a single 250 mL centrifuge tube to be washed in Lactated Ringer's. After the last wash the cells are transferred to a 50 mL centrifuge tube and resuspended in 50 mL of Lactated Ringer's. A 1 mL sample of the cell suspension is taken for a cell count and cell viability determination. The cells are then pelleted and resuspended at $30\times10^6$ viable cells/mL of freezing solution (80% heat-inactivated autologous serum, 10% Plasma-Lyte A (Baxter, NDC Number: 0338-0221-04) supplemented with 5% dextrose, and 10% Dimethyl Sulfoxide (DMSO)). The final step of the process is to fill/freeze and then store the frozen DC vaccine for clinical use. The DC vaccine is filled into 2 mL glass vaccine vials according to SOP VP121 "Manual Cryopreservation of Dendritic Cell Vaccines in Glass Vaccine Vials". A 5 mL disposable plastic pipette is used to transfer 1 mL of the DC vaccine suspension to each glass vaccine vial. The vials are sealed with a rubber stopper and metal flip-off cap. The sealed vaccine vials are then placed in a pre-cooled controlled rate freezer with the freezing program initiated as described in SOP EQ143 "Kryo 1020-380 Controlled Rate Freezer". After the cells are frozen the vials of DC vaccine are placed in a –80° C. freezer and held for at least 4 hours but not more than 24 hours. The frozen vials are then transferred to the quarantine section of the liquid nitrogen tank in the GMP freezer room. On the day that QC release testing is initiated, a vial is randomly selected from the DC vaccine batch for QC release testing. Upon completion of the QC testing and QA release the DC vaccine batch is moved to the released product storage section of the liquid nitrogen tank.

Process Timing and Intermediate Storage.

The entire manufacture of a BIIR-BrcaVax-001 DC vaccine batch is conducted in a single continuous process; thus, there is not an intermediate storage step in the manufacturing process. The timing of key steps of the full manufacturing campaign to prepare a single DC vaccine batch, which runs approximately 90 hours, is summarized in FIG. 3. Briefly, on Day 0 the patient's peripheral blood mononuclear cells are collected by apheresis, which is transferred to the GMP vaccine manufacturing facility for enrichment of the monocyte fraction to initiate the DC culture. On Day 1 after 24 hours in culture fresh GM-CSF and IFN-α are added to the cell culture bags to replenish these cytokines in the cell culture media. On Day 2 after approximately 48 hours of cell culture the tumor and control antigen peptides are added to the cell culture to load the DC with the specified antigen epitopes. On Day 2, immediately after addition of the antigen peptides, the LPS, CD40L and CL075 are added to the culture to activate the antigen loaded DC. After 24±1 hours of incubation with the antigens, LPS, CD40L and CL075 the DC vaccine is harvested from the cell culture bags, washed, resuspended in freezing solution, filled into glass vaccine vials, frozen in a controlled rate freezer and stored overnight in a –80° C. freezer. Following 4-24 hours storage at –80° C., the frozen batch of DC vaccine product is transferred to a liquid nitrogen tank for long-term storage.

Final Harvest.

Step 4 of the BIIR-BrcaVax-001 manufacturing process is harvest of the DC vaccine from the cell culture bags for fill/freezing. On Day 3, after approximately 72 hours in cell culture, the antigen-loaded, LPS/CD40L/CL075 activated DC are harvested from the cell culture bags by the following process. Prior to harvesting the cells 6 mL samples are collected from six of the cell culture bags selected at random for sterility and *mycoplasma* testing. The cells are then collected from the cell culture bags and pooled by transferring the contents of the cell culture bags into 600 mL transfer packs, that is, the contents of ≤4 cell culture bags is transferred to each transfer pack. After the cell culture suspensions are transferred to the transfer packs, each of the cell culture bags are then thoroughly washed with 25 mL of Lactated Ringer's. The cell culture bags are reconnected to the transfer packs and the Lactated Ringer's rinsed cells are transferred to the transfer packs. The transfer packs are centrifuged to pellet the cells. The cells are resuspended in Lactated Ringer's and pelleted by centrifugation. After the second wash the cell pellet is dispersed and the cell suspension in each of the transfer packs is transferred to a single 250 mL centrifuge tube. Lactated Ringer's is then added to Q.S. the cell suspension to 250 mL in the centrifuge tube. After centrifugation the pelleted cells are then resuspended in 20 mL of Lactated Ringer's and transferred to a 50 mL centrifuge tube. The 250 mL tube is rinsed with 20 mL of Lactated Ringer's that is added to the 50 mL tube and the cell suspension is Q.S. to 50 mL with Lactated Ringer's. A 1 mL in-process QC sample is taken to determine the cell count and viability. The cells are pelleted by centrifugation and then resuspended in heat-inactivated autologous serum at $60\times10^6$ viable cells/mL. At this point the cell suspension is ready for the addition of an equal volume of 2× freezing solution to initiate the fill/freeze step of the process.

Timing/Methods/Wash Procedures.

Cells are washed at several points in the BIIR-BrcaVax-001 DC vaccine manufacturing process. The basic method is to pellet the cells by centrifugation, that is, the cells in either bags or tubes are centrifuged to pellet the cells and remove the suspension solution. Following is a brief summary of the points in the process where the cells are washed.

1. Washing the elutriation enriched monocytes. The elutriation fraction bag(s) containing the enriched monocyte population is connected to a 150 mL transfer pack and the monocytes are transferred. An additional transfer pack is used if the volume of the elutriation fraction bag exceeds 150 mL. The transfer pack(s) is centrifuged at 770×g for 10 minutes at ambient room temperature to pellet the cells. After centrifugation the supernatant is removed from the bag and the cell pellet is dispersed and transferred to a 2 L transfer pack. The 150 mL transfer pack(s) is rinsed with 25 mL of normal saline which is then transferred to the 2 L transfer pack. CellGro® media is then added to the transfer pack to bring the cell concentration to $1\times10^6$ viable cells/mL.

2. Washing of the antigen-loaded, LPS/CD40L/CL075 activated DC at the time of cell harvest. The DC cell culture suspension and volume of Lactated Ringer's used to rinse the cell culture bags are transferred to 600 mL transfer packs. The transfer packs are centrifuged at 770×g for 10 minutes at ambient room temperature. The supernatant is removed from the cell pellet by transferring it from the transfer pack to a sterile connected empty transfer "waste" pack. The cell pellet is gently dispersed and approximately 25 mL of Lactated Ringer's is added to each of the transfer packs. The cells are pooled into one transfer pack and Lactated Ringer's is added to a volume of approximately 500 mL. The transfer packs are centrifuged at 770×g for 10 minutes at ambient room temperature. The solution is removed from the cell pellet by transferring the supernatant from the transfer pack to a sterile connected empty transfer "waste" pack. The Lactated Ringer's wash step is then repeated. The cell pellet in each transfer pack is gently dispersed and the cell suspensions transferred to and pooled in a single 250 mL centrifuge tube. The cell suspension in the centrifuge tube is Q.S. to 250 mL with Lactated Ringer's. The cells are pelleted by centrifugation at 770×g for 10 minutes at ambient room temperature. The supernatant is removed, the cell pellet dispersed and the cells suspended in 20 mL of Lactated Ringer's. The cell suspension is transferred to a 50 mL centrifuge tube. The 250 mL tube is rinsed with 20 mL of Lactated Ringer's that is transferred to the 50 mL tube. The cell suspension in the 50 mL tube is Q.S. to 50 mL with Lactated Ringer's and, after removing a 1 mL sample for in-process QC testing, the cells are pelleted by centrifugation at 270×g for 10 minutes at ambient room temperature. During the final wash the in-process QC sample is analyzed to determine the cell count and viability. The washed cells are then resuspended in a volume of heat-inactivated autologous serum to give a cell concentration of $60\times10^6$ viable cells/mL. The cell suspension is now ready for addition of the freezing solution and initiation of the fill/freeze process.

Final Formulation.

The BIIR-BrcaVax-001 DC vaccine is prepared for injection into the patient by thawing the requisite number of frozen vials of DC vaccine and diluting the contents with USP injection grade sterile Lactated Ringer's (Hospira, NDC Number: 0409-7953-02, 250 mL bag for preparing the Vaccine Product for injection; and 0409-7953-09, 1 L bag for use in the DC vaccine manufacturing process) to wash the cells by centrifugation. The cells are washed 3 times with Lactated Ringer's. Prior to the third wash a sample is taken to determine the cell count and viability. After the third wash the cells are resuspended in Lactated Ringer's at a concentration of $15\times10^6$ viable cells/mL. The cell suspensions are filled into a 2 mL sterile glass vaccine vial sealed with a serum stopper and metal cap, for delivery to the clinic. Therefore, the final formulation is comprised of the DCs suspended in 100% Lactated Ringer's.

Extensive QC release testing of the frozen vaccine will include:
a) Cell Count (Recovery) and Viability
b) Evaluation of DC morphology by Giemsa staining of cytospun cells
c) Evaluation of DC phenotype by multiparameter flow cytometry analysis
d) Sterility testing (*mycoplasma*, gram stain, bacteria/fungus growth, and endotoxin)
e) Potency testing by phenotype and cytokine secretion.

QC release testing of the washed DC vaccine for injection will include:
a) Cell count and viability
b) Sterility testing: gram stain and endotoxin (results available prior to injection)
c) Sterility testing: bacterial and fungal growth (results available after injection)

Excipients.

Following is a list of the excipients employed in the BIIR-BrcaVax-001 DC vaccine manufacturing process. These excipients, except for the Lactated Ringer's used to suspend the DC in the final formulation for injection into the patent, are not retained in the final, frozen DC vaccine product or Vaccine Product prepared for injection because they are removed by washing the cells.

Elutriation Buffer. The elutriation buffer is prepared by adding 500 mL of 5% human serum albumin to a 4 L bag of 1× Hank's Balanced Salt Solution. The components used to prepare the elutriation buffer are described below.

Hank's Balanced Salt Solution, (HBSS, BioWhittaker® brand, Lonza, Catalog Number: 08-003A) is a sterile, isotonic solution at pH 7.0 to 7.4 that is packaged in 4 L plastic bags and is stored at ambient room temperature.

5% Human Serum Albumin, USP grade (Baxter, NDC Number: 0944-0491-02 or CSL Behring, NDC Number: 0053-7670-32) is a sterile, nonpyrogenic solution supplied at 500 mL in glass bottles and is stored at ambient room temperature.

Cell Freezing Solution. The final formulation of the DC vaccine freezing solution is comprised of 80% heat-inactivated autologous serum, 10% Plasma-Lyte A supplemented with 5% dextrose, and 10% Dimethyl Sulfoxide (DMSO). The components used to prepare the freezing solution are described below.

Heat-Inactivated Autologous Serum. Autologous serum is obtained from peripheral blood drawn from the patient in red top Vacutainer® tubes prior to apheresis. The serum is separated from the clotted blood by centrifugation. The serum is transferred to a sterile 50 mL tube labeled "Serum" with the patient's identification, study number and date. The serum is filter sterilized by passing it through Acrodisc 0.2 micron, 37 mm syringe filters for aliquotting into labeled, sterile 15 mL tubes. The tubes are placed in a 56° C. heat block for 30 minutes to heat-inactivate the serum. "Heat-Inactivated" is then added to the tube label and the serum is stored refrigerated at 2-8° C. until use.

Plasma-Lyte A, (Multiple Electrolytes Injection, Type 1, USP; Baxter, NDC Number: 0338-0221-04) is a sterile, non-pyrogenic isotonic solution supplied in a 500 mL VIAFLEX plastic container for intravenous administration and is stored at ambient room temperature.

70% Dextrose, USP injection grade, (Hospira, NDC Number: 0409-7918-19) is supplied at 500 mL in partially filled 1 L plastic bags and is stored at ambient room temperature.

Dimethyl Sulfoxide, (DMSO, Cryoserv® brand; NDC Number: 67457-178-10 or Number: 67457-178-50) is supplied as a sterile, 99% pure solution at 10 or 50 mL, respectively, in flip-top glass vials and is stored at ambient room temperature.

Lactated Ringer's Injection, USP, (Hospira) is a sterile, nonpryogenic solution containing isotonic concentrations of sodium chloride 600 mg, sodium lactate anhydrous 310 mg, potassium chloride 30 mg and calcium chloride dehydrate 20 mg. May contain hydrochloric acid and/or sodium hydroxide for pH adjustment. Lactated Ringer's is supplied in either a 250 mL bag (NDC Number: 0409-7953-02) used for preparation of the Vaccine Product for injection, or a 1 L bag (NDC Number: 0409-7953-09) used in the DC vaccine manufacturing process. The bags are stored at 20 to 25° C. (68 to 77° F.) and are protected from freezing.

PBS, phosphate buffered saline without Ca' and Mg' at pH 7.2 (GIBCO®, Catalog Number: 20012-027) is supplied as a sterile solution in 500 mL plastic bottles and is stored at ambient room temperature.

Normal Saline, USP injection grade, 0.9% sodium chloride (Hospira, NDC Number: 0409-7983-03) is supplied as a sterile solution in 500 mL plastic bags and is stored at ambient room temperature.

Sterile Water for Injection, USP grade (referred to herein as Sterile Water; Hospira, NDC Number: 0409-4887-10) is supplied as a sterile solution in 10 mL flip-top plastic vials and is stored at ambient room temperature.

Cell Density/Concentration in the Final Product.

The DC vaccine is thawed, washed with Lactated Ringer's and suspended in USP injection grade sterile Lactated Ringer's at $15 \times 10^6$ viable cells/mL with 1.5 mL of the cell suspension filled into a glass vaccine vial for use by the clinic.

Storage Method Prior to Use.

The frozen BIIR-BrcaVax-001 DC vaccine is stored at −180° C. (liquid nitrogen vapor phase). The thawing and DMSO washout process is conducted at ambient room temperature. The cell preparation for injection is transported to the bedside at ambient room temperature. The elapsed time from preparation of the DC vaccine for injection and vaccination of the patient is approximately 3 hours.

B. In-Process Testing and Criteria.

In-process testing is conducted at several points in the BIIR-BrcaVax-001 DC vaccine manufacturing process. Specifically, to quantify the patient's monocytes in-process samples are taken from the apheresis to determine sterility and from the elutriation fraction to determine monocyte purity, cell count and cell viability. In-process samples are taken at the time of harvest of the DC vaccine for sterility testing, *mycoplasma* testing, and determination of cell count and viability. The various in-process tests are summarized in Table 2 and Table 3 below.

TABLE 2

In-Process Tests and Specifications
Preparation of the Monocytes

| Process Step | Test Method | Result | Specification |
|---|---|---|---|
| Apheresis | Sterility (Gram-Stain and Microbial Growth) | Performed by BUMC for Information Only - Used if Out-of-Specification investigation is required. | Apheresis should be sterile, that is, gram-stain negative and free of bacteria and fungus contamination. |
| Elutriation | Hematology Analyzer (Users Manual) | Identity and percentage (purity) of the monocytes in the elutriation fractions. Result used to select the elutriation fraction(s) for culture | Monocyte purity ≥50% for Fraction 5; and ≥70% for Fraction 4 if being combined with Fraction 5. |
| Elutriation | Cell Count and Viability by Trypan Blue Staining (SOP VR109). | Total number and viability of cells to determine the cell concentration for cell culture. | Report result |

TABLE 3

Further In-Process Tests and Specifications
Manufacture of the DC Vaccine

| Process Step | Test Method | Result | Specification |
|---|---|---|---|
| DC Harvest | Sterility Bacterial and Fungal Growth (SOP VR119) | Presence/Absence of microbes, i.e., bacteria in 14 day growth cultures and fungus in 28 day growth cultures. | Negative for bacteria and fungus |

TABLE 3-continued

Further In-Process Tests and Specifications
Manufacture of the DC Vaccine

| Process Step | Test Method | Result | Specification |
|---|---|---|---|
| DC Harvest | Sterility Gram Stain (SOP VR119) | Presence/Absence of gram stain positive organisms. | Negative for gram-positive organisms |
| DC Harvest | Mycoplasma detection by Hoechst Staining and Growth Culture (SOP VR120) and PCR (SOP VR111). | Presence/Absence of Hoechst 33342 stained mycoplasma, mycoplasma DNA by PCR, and mycoplasma in 28 day growth culture. | Negative for Mycoplasma |
| DC Harvest | Cell Count and Viability by Trypan Blue Staining (SOP VR109). | Total number and viability of cells to determine cell concentration for fill/freezing. | Count: $30 \times 10^6$ viable cells per mL per glass vaccine vial |

Monocyte Identity and Purity.

The Coulter AcT5 Hematological Analyzer is an automated system used to identify the various peripheral blood cell populations in the different elutriation fraction bags. The instrument uses flow impedance, cytochemistry and light absorbance to differentiate the blood cell populations. The instrument readout provides both cell number and percentage of the various peripheral blood cell populations in the sample. The samples are analyzed to identify which elutriation faction contains the enriched monocyte population (usually Fraction 5) and determine the purity (percentage) of monocytes in the elutriation fraction. The printout of the AcT5 results is filed with the Vaccine Production Record used for documenting the preparation and QC release of the DC vaccine batch.

Cell Count and Viability.

The total number of cells and determination of cell viability is determined by light microscopic examination of the trypan blue stained cell suspension loaded onto a hemocytometer. The cell count and viability assay is performed according to the method described in SOP VR109 "Cell Count and Viability Using Trypan Blue Stain". Briefly, cells are counted on three fields of the hemocytometer. The number of non-stained (viable) and trypan blue stained (non-viable) cells are recorded for each field. The average number of viable and non-viable cells is calculated from the combined results of the three fields. Based on the calculated average, the number of cells per mL of cell suspension is established and the percentage of viable cells is determined. The information is used to make cell dilutions for setting up cell cultures and filling glass vaccine vials. In-process samples to determine cell count and viability are collected from the elutriation fraction containing the monocytes to initiation of the DC culture, and the DC harvest.

Sterility Testing at the Laboratories at Bonfils.

A sample is taken at DC vaccine harvest and sent to the Laboratories at Bonfils for a gram stain, 14 day bacterial growth culture, and 28 day fungal growth culture. Results should be negative; however, the DC vaccine products may be released for the first vaccination before the final reports are received. See the specific actions to be taken to monitor and if necessary treat the patient should the frozen, autologous DC vaccine be shown to be non-sterile after the first vaccination has been performed in the sections below for QC release of the final product. Following is a description of the sterility testing conducted at the Laboratories at Bonfils.

Bonfils Laboratories (LABS) is registered with the FDA, FEI #1000477683, and conducts sterility testing by USP methodologies. Microbiological testing, including sterility testing is performed at LABS following the latest United States Pharmacopeia (USP) compendia of methods. LABS also complies with 21 CFR Part 610 General Biological Products Standards section 610.12 on Sterility and with the AATB Standards for Tissue Banking, Section K3.000 regarding Microbiological Testing. LABS is an ISO certified, FDA registered testing facility that assures that microbiological testing is performed using validated test methods, validated equipment and a staff of fully trained microbiologists.

Microbiological media used for the detection of aerobic, anaerobic and fungi organisms are chosen based on requirements in the CFR. Trypticase Soy Broth, which is the same as Soybean-Casein Digest Medium, and Fluid Thioglycollate Medium are used for the sterility cultures as prescribed. Trypticase Soy Broth is used for aerobic organisms and for yeast and mold detection. Fluid Thioglycollate Medium is used for culture of anaerobes, facultative anaerobes and for aerobic bacteria.

LABS purchases TSB and FTM from approved vendors and while the standard developed by the Clinical Laboratory Standards Institute does not require QA testing on these media if purchased commercially, LABS tests all media for its ability to promote microbial growth before it is used in sterility tests. The sterility culture incubation period is 14 days per the requirements in the CFR and in the USP. Cultures are read at 3, 4 or 5 days, at 7 days and a final reading at 14 days (Bacteria) or 28 days (Fungus). If the media is turbid at any reading, the microbiologist performs a gram stain and subculture as appropriate.

*Mycoplasma* Testing.

A sample of the BIIR-BrcaVax-001 DC vaccine culture is taken from the cell culture prior to DC vaccine harvest for *mycoplasma* testing. A portion of the sample is tested in the BIIR QC Laboratory for the presence of *mycoplasma* DNA using the PCR method described in SOP VR111 "*Mycoplasma* Detection by PCR". The results of the PCR test are expected to be negative for the presence of *mycoplasma* DNA in the DC culture sample. Another portion of the sample is sent to Bionique Laboratories for their M700 assay that includes a 28 day direct culture and an indirect Hoechst stain using indicator cell lines. Preliminary results of the direct culture are received on day 7. Any positive result at any time during the 28 day culture period is reported immediately to the GMP manager, Quality Assurance (QA) Unit and Principle Investigator (PI). Final results for the Hoechst stain are available 5 days after initiation of the assay. The results should be negative for *mycoplasma*. The remainder of the sample is saved as a "Retain Sample" for future testing if necessary.

Bionique Testing Laboratoires' FDA registration number is 1318709. Bionique Laboratories conducts testing in compliance with cGMP standards outlined in 21CFR parts 210 and 211; that is, "Recommended Procedures for Detection of *Mycoplasma* Contamination in Biological Products Produced in Cell Substrates". The purpose of this test is to determine whether or not mycoplasmal contaminants are present in cell culture samples or bioproducts derived from cell culture substrates. The procedure requires a non-selective indirect DNA fluorochrome staining assay to detect non-cultivable mycoplasmas and a direct culture assay. The indicator cell/DNA fluorochrome staining procedure requires the inoculation of the sample into 2 indicator cell cultures (slide cultures of VERO cells). Two sample (1.0 mL) aliquots are inoculated into each of two quality controlled slide cultures of mycoplasmal free VERO cells and incubated (5% $CO_2$, 95% Air) for 3 to 5 days. Usually on Day 4, each slide culture is fixed with Carnoy's fixative and stained with Hoechst DNA fluorochrome stain. This assay is designed to enhance the level of sensitivity by reducing background and amplifying the titer of mycoplasmal contaminants. Appropriate positive control cultures, *M. hyorhinis* and *M. orale* at <100 CFU, and a negative control culture are processed with each batch of tests as specified by the FDA. The theoretical sensitivity of this assay is approximately 50 CFU. The direct culture procedure utilizes Fortified Commercial (FC) broth and agar formulations. A 10 mL sample aliquot is inoculated into 50 mL of FC broth supplemented with 20% horse serum. A 0.1 mL sample is inoculated onto 4 FC agar plates. The broth culture is subcultured onto like agar plates on Day 3, Day 7 and Day 14 post setup as specified per FDA guidelines. The agar plates are incubated aerobically and anaerobically (5% $CO_2$, 95% nitrogen). The FC agar plates are examined microscopically at 7 day intervals. Two positive controls, *M. pneumoniae* and *M. orale* (<100 CFU) and a negative control are processed with each batch of tests as specified by the FDA. The theoretical sensitivity of the direct culture assay is approximately 10 CFU. All media and supplemental components used for screening purposes are tested for sterility and for the ability to support *mycoplasma* growth. Total testing time is 28 days.

C. Final Product Release Criteria/Specifications and Test Methods

Each patient's frozen batch of autologous DC vaccine is tested and released according to the procedures and specifications outlined in SOP VR151 "Release Testing for DC Vaccine Product BIIR-BrcaVax-001". The test results and Certificate of Analysis for each frozen batch of autologous DC vaccine product are reviewed and signed-off by both GMP Management and the Quality Assurance Unit. The final product release testing is performed on a vial of frozen DC vaccine randomly selected from the DC vaccine batch obtained at the time the batch is transferred from the −80° C. freezer to the quarantine section of the liquid nitrogen storage tank. The QC test methods and specifications used to assess and release these final products are summarized below in Table 4 and Table 5.

TABLE 4

Test Methods and Specifications for Final Product Release
Frozen Autologous DC Vaccine Products

| Sample | Test Method | Result | Specification |
|---|---|---|---|
| Portions of the cell suspension taken from the Lactated Ringer's diluted thawed DC vaccine vial. | Dose: Cell Count and Viability by Trypan Blue Staining (SOP VR109) | Total number and viability of cells in the vial after thawing. | Count ≥50% of the fill target (Recovery) Cell Viability ≥50% |
| | Identity: Giemsa Staining (SOP VR107) | Identification of cell with characteristics of DC morphology. | Report Result |
| | Identity/Purity: Flow Cytometry (SOP VR137) | Percentage of cells with the specified DC phenotype. | ≥80% HLA-DR+ CD11c+ cells |
| | Phenotypic Potency: Flow Cytometry (SOP VR137) | Percentage of cells with the phenotype indicative of DC potency. | ≥70% CD80+ Cells |
| | Sterility: Gram-Stain (SOP VR119) | Presence/Absence of gram-positive organisms. | Gram-Negative |
| | Sterility: Endotoxin by Endosafe ® LAL Test (SOP VR134) | Determine the amount of endotoxin in the product. | <0.5 EU/mL <5 EU/dose |
| | Sterility: Bacterial/Fungal Cultures (SOP VR119) | Presence/Absence of bacteria and fungus | Interim and Final Results negative for microbial contamination |
| | Functional Potency: Luminex measurement of DC Cytokine Secretion (SOP VR148) | Characterization test of the amount of IL-23, IL-12p40, and IL-12p70 secreted by the DC. Additional cytokines may also be analyzed. | Report Result |

NOTE:

The 14 day bacteria and 28 day fungal and mycoplasma growth culture results may not be available at the time of release of the Vaccine Batch Product for preparation of the inoculates for injection into the patient. Interim results are monitored during the course to the testing process. Final results of the bacterial, fungal and mycoplasma culture are reviewed for final product release by QA (See signature line on CoA). An action plan (see below) is in place to respond to a positive result of a sterility test reported post-release of either the frozen Vaccine Product or Vaccine Inoculate.

TABLE 5

Test Methods and Specifications for Final Clinical Product Release
(i.e., Inoculate Filled in the Glass Vaccine Vial).
Washed Autologous DC Vaccine Inoculate

| Sample | Test Method | Result | Specification |
|---|---|---|---|
| Portions of the cell suspension after the cells were thawed and washed to prepare the inoculate(s). | Dose: Cell Count and Viability by Trypan Blue Staining (SOP VR109) | Total number of viability cells in suspension filled in the syringe. | $15 \times 10^6$ viable cells/mL with 1.5 mL filled into a glass vaccine vial for injection. |
| | Sterility: Gram-Stain (SOP VR119) | Presence/Absence of gram-positive organisms. | Gram-Negative |
| | Sterility: Bacterial/Fungal Cultures (SOP VR119) | Presence/Absence of bacteria and fungus | Negative for microbial contamination |

NOTE:
The gram-stain, 14 day bacteria and 28 day fungal growth culture results may not be available at the time of release of the vaccine inoculates for injection into the patient. Interim results are monitored during the course to the testing process. Final results of the gram-stain, bacterial and fungal growth cultures are reviewed and released by QA. The following action plan is in place to respond to a positive result of a sterility test reported post-release of the vaccine inoculate.

Cell Count and Viability.

The cell count and viability assay is performed according to the method described in the In-Process Test Method section above.

Endotoxin.

Endotoxin testing is performed to release each batch of frozen DC vaccine product. The amount of endotoxin in the product is determined by an automated LAL assay using the Endosafe® portable test system. The Endosafe® is a rapid, point-of-use test system for quantitative LAL test results in approximately 15 minutes. It is comprised of a test cartridge along with a hand-held spectrophotometer. The Endosafe® endotoxin test utilizes existing FDA-licensed LAL formulations. Test cartridges are available to achieve a level of sensitivity as low as 0.01 EU/mL. Results of the endotoxin testing will be available to release the frozen DC vaccine batches. To release the DC vaccine products endotoxin levels should be less than 0.5 EU/mL or 5 EU/dose.

Sterility Testing at the Laboratories at Bonfils.

A sample is taken from the final product, i.e., thawed cell suspension from the frozen DC vaccine batches at the time of QC release testing and from the DC vaccine inoculate, and sent to the Laboratories at Bonfils for a gram stain, 14 day bacterial growth culture, and 28 day fungal growth culture. Results should be negative; however, DC vaccine products are released for the first vaccination before the final reports are received. The frozen DC vaccine batches may be and the DC vaccine inoculates are released for the first vaccination of the patient prior to or on preliminary growth culture results but the final results are known before subsequent vaccinations. Specified actions are taken to monitor and if necessary treat the patient should the frozen, autologous DC vaccine or inoculate be shown to be non-sterile after the vaccination has been performed (see the Notes after Tables 4 and 5 above). Following is a description of the sterility testing conducted at the Laboratories at Bonfils.

Bonfils Laboratories (LABS) is registered with the FDA, FEI #1000477683, and conducts sterility testing by USP methodologies. Microbiological testing, including sterility testing is performed at LABS following the latest United States Pharmacopeia (USP) compendia of methods. LABS also complies with 21 CFR Part 610 General Biological Products Standards section 610.12 on Sterility and with the AATB Standards for Tissue Banking, Section K3.000 regarding Microbiological Testing. LABS is an ISO certified, FDA registered testing facility that assures that microbiological testing is performed using validated test methods, validated equipment and a staff of fully trained microbiologists.

Microbiological media used for the detection of aerobic, anaerobic and fungi organisms are chosen based on requirements in the CFR. Trypticase Soy Broth, which is the same as Soybean-Casein Digest Medium, and Fluid Thioglycollate Medium are used for the sterility cultures as prescribed. Trypticase Soy Broth is used for aerobic organisms and for yeast and mold detection. Fluid Thioglycollate Medium is used for culture of anaerobes, facultative anaerobes and for aerobic bacteria.

LABS purchases TSB and FTM from approved vendors and while the standard developed by the Clinical Laboratory Standards Institute does not require QA testing on these media if purchased commercially, LABS tests all media for its ability to promote microbial growth before it is used in sterility tests. The sterility culture incubation period is 14 days per the requirements in the CFR and in the USP. Cultures are read at 3, 4 or 5 days, at 7 days and a final reading at 14 days (Bacteria) or 28 days (Fungus). If the media is turbid at any reading, the microbiologist performs a gram stain and subculture as appropriate.

Giemsa Stain.

Evaluation of DC morphology in the DC vaccine is performed by Giemsa staining of cyto spun cells. Cells should exhibit dendritic cell morphology. This is considered a characterization assay, thus, the DC vaccine batches are released on a report of the assay results.

Cell Phenotype.

The determination of the DC phenotype is performed by multiparameter flow cytometric analysis using the BD FACSCanto™ II Flow Cytometry System. An antibody panel has been established to determine the phenotype of the DC vaccine products. The DC vaccine phenotyping panel consists of the following fluorescent-labeled monoclonal antibodies: CD1b/c FITC, CD80 PE, HLA-DR PerCP, CD83 APC, CD14 APC-H7 and CD11c Horizon (Pacific Blue). The cells are also stained with anti-CD45 pacific orange monoclonal antibody, which is used to gate the cells for FACS analysis. A single tube of cells is stained with the mixture of phenotyping antibodies and analyzed on the FACSCanto. The data are reported as the percentage of cells expressing a particular cell marker or combination of cell markers as detected by the fluorescent-labeled monoclonal antibodies in the phenotyping panel. For release of each frozen batch of BIIR-BrcaVax-001 DC vaccine product the following cell phenotype specifications must be achieved, i.e., for DC identity ≥80% of the cells should be HLA-DR+ CD11c+ and for DC phenotypic potency ≥70% of the cells should be CD80+. The results are reported for the other cell phenotype markers analyzed to help further characterize the DC vaccine products.

D. Potency—Characterization Assay

The potency assay for characterization of the BIIR-BrcaVax-001 breast cancer therapeutic DC vaccine product is currently under development. In addition to determining the phenotypic potency of the DC vaccine by flow cytometry (see above) there is a characterization assay that will be performed to assess the functional potency of the DC vaccine product. This assay will measure by Luminex analysis the secretion of critical cytokines, i.e., IL-12p40, IL-12p70 and IL-23, by the DC. The antigen-loaded and activated DC are expected to secrete significant levels of these cytokines. In addition to IL-12p40/p70 and IL-23 other cytokines may also be analyzed.

3. Vaccine Administration and Vaccine Schedule

Patients will receive preoperative dose-dense dense AC/T chemotherapy for 16 weeks combined with antigen-pulsed DC vaccinations administered on Day 2 of Cycle 1 and 3 of dose-dense AC and on Day 3 of Cycle 1 and 3 of T (4 timepoints).

At each scheduled vaccination during the preoperative phase, the patient will receive a total of 2 injections. Each vaccination will consist of:

One intratumoral injection of 0.2 mL ($3\times10^6$ cells/mL)

One subcutaneous injection of 1 mL ($15\times10^6$ cells/mL) in the ventral surface of the upper arm (ipsilateral).

DC vaccinations will be administered to the patient prior to administering AC/T on the given day.

After definitive surgery and during locoregional radiation therapy to breast or chest wall and regional lymphatics per standard of care, patients will receive 3 boost DC vaccinations subcutaneously of 1 mL each ($15\times10^6$ cells/mL) in the ventral surface of the upper arm (contralateral).

The first vaccination booster will occur once after the surgery and prior to radiation.

The second booster will occur 30 days±3 days after radiation is completed.

The third booster will occur 90 days±3 days after the $2_{nd}$ boost.

Patients will be monitored post DC infusion for any signs of infusion related reaction every 15 minutes for 1 hour.

Figure 2:
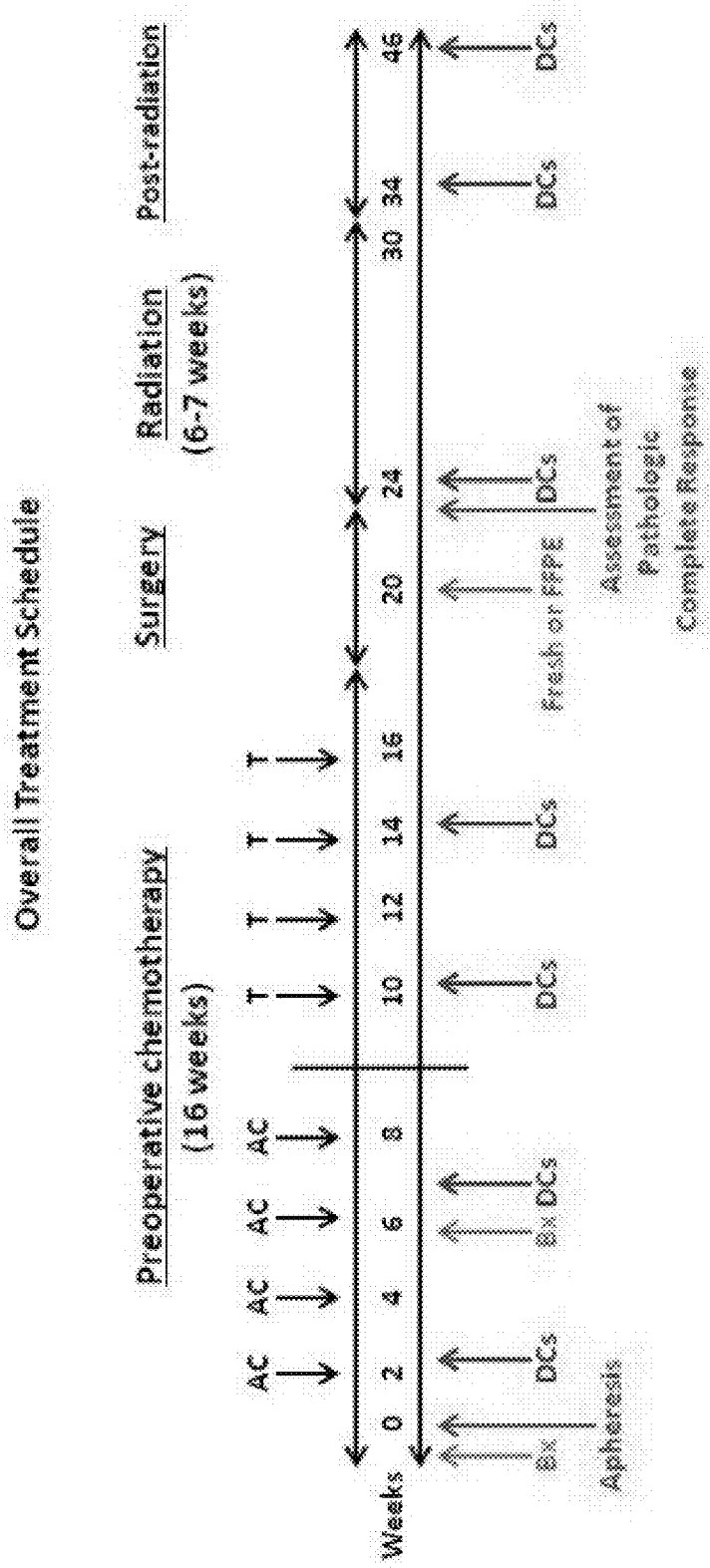
FIG. 2—DC vaccination schedule. Schedule of administration of DC vaccines in combination with preoperative chemotherapy, surgery, and radiation.

The DC vaccination schedule is shown in FIG. 2.

4. Anakinra Administration

Anakinra is a recombinant soluble non-glycosylated homolog of the human interleukin-1 receptor antagonist (IL-1Ra) that competitively inhibits binding of IL-1α and IL-1β to the receptor type I. Anakinra differs from native human IL-1Ra in that it has the addition of a single methionine residue at its amino terminus. It is produced by recombinant DNA technology using an *E coli* bacterial expression system. Anakinra consists of 153 amino acids and has a molecular weight of 17.3 kilodaltons. Anakinra is supplied in single use prefilled glass syringes with 27 gauge needles as a sterile, clear, colorless-to-white, preservative-free solution for daily subcutaneous (SC) administration. The solution may contain trace amounts of small, translucent-to-white amorphous proteinaceous particles. Each prefilled glass syringe contains: 0.67 mL (100 mg) of anakinra in a solution (pH 6.5) containing sodium citrate (1.29 mg), sodium chloride (5.48 mg), disodium EDTA (0.12 mg), and polysorbate 80 (0.70 mg) in Water for Injection, USP. Dosing and administration of anakinra will be as follows:

Group 1:
DC vaccine plus preoperative chemotherapy, no treatment with anakinra for 16 weeks: 10 patients Group 2:
DC vaccine plus preoperative chemotherapy; anakinra 100 mg 7 days, followed by 7 days off, then repeating, subcutaneously for 16 weeks: 10 patients Anakinra is self-administered, with the exception of first dose of anakinra which will be administered in the clinic. Before any anakinra is administered, each patient will be instructed by the Investigator or his/her representative on the proper self-administration of study drug and advised to take any missed dose as soon as possible.

Each patient registered in Group 2 only will be instructed to self-inject subcutaneously one pre-filled syringe of anakinra (100 mg) for 7 days, followed by 7 days of rest, then repeating, at about the same time every day during the 16 weeks of preoperative chemotherapy. Anakinra must be stored in a refrigerator and warmed to room temperature for 60-90 minutes prior to injection. This dose was the recommended dose for the treatment of patients with rheumatoid arthritis. Higher doses did not result in a higher response.

5. Apheresis

The use of apheresis for the collection of human blood mononuclear cells is commonly done in the practice of hematology and oncology. For venous access, patients will either undergo venipuncture of the antecubital veins in both arms or a central venous catheter will be inserted in those patients whose venous access is insufficient to undergo apheresis by venipuncture.

After the mononuclear cells are collected from the patients, and received by the cGMP Facility at BIIR they will undergo further processing for generation of the DC vaccine. Specifically the monocytes will be separated from other mononuclear cells using a closed elutriation system ELUTRA (Gambro).

6. Efficacy Assessments: Evaluation of Pathologic Response

Pathologic response to therapy is the primary endpoint of the study protocol. Patients will undergo surgical resection of residual breast and axillary malignant tissue after protocol-directed treatment. The pathologic specimen will be graded according to the tumor regression grading schema called the Residual Cancer Burden (RCB) (Symmans, et al., 2007). The following parameters are required from pathologic examination in order to calculate RCB after neoadjuvant treatment:

1. The largest two dimensions (mms) of the residual tumor bed in the breast (largest tumor bed if multicentric disease)
2. Submission of the entire largest cross-sectional area of the residual tumor bed for histologic mapping, with specific identification of those slides in the pathology report (e.g., "the largest cross-sectional area of primary tumor bed was submitted in cassettes A5-A9")

If the residual tumor is large (i.e. largest diameter>5 cm), then at least 5 representative cassettes from the largest cross-sectional area are sufficient, but should be identified in the original pathology report (e.g. "representative sections from the largest cross-sectional area of primary tumor bed were submitted in cassettes A5-A9")
3. Histologic assessment of the percentage of the tumor bed area that contains carcinoma (all carcinoma, i.e. invasive and in situ), select one of the following:
    0%, 1%, 5%, 10%, 20%, 30%, 40%, 50%, 60%, 70%, 80%, 90%

To assess cellularity it is helpful to scan across the sections of tumor bed and then estimate the average cellularity from the different microscopic fields.

When estimating percentage cancer cellularity in any microscopic field, compare the involved area with obvious standards, e.g. more or less than half, one quarter, one fifth, one tenth, one twentieth, etc.

Expect there to be variable cellularity within the cross section of any tumor bed, but estimate the overall cellularity from the average of the estimates in different microscopic fields of the tumor bed.

e.g. if cellularity in different fields of the tumor bed were estimated as 20%, 10%, 20%, 0%, 20%, 30%, then an average estimate of overall cellularity would be 20%.

4. Histologic estimate of the percentage of the carcinoma in the tumor bed that is in situ, select one of the following:

0%, 1%, 5%, 10%, 20%, 30%, 40%, 50%, 60%, 70%, 80%, 90%, 100%

5. The number of positive (metastatic) lymph nodes
6. The largest diameter (mm) of the largest nodal metastasis A pathologic complete response (pCR) is defined as NO pathologic evidence of invasive disease in the breast or axillary lymph nodes.

The presence or absence of a pCR will be assessed separately for the tumor and the lymph nodes. For patients who do not achieve a pCR, the size of the residual cancer in the tumor, on pathologic exam, will be documented in the as well as the number of positive lymph nodes. Patients will have their pathologic response scored using the RCB scale.

7. Efficacy Assessments: Statistical Methods

Immunologic studies will explore immune responses in the peripheral blood and the primary breast cancer tissues. Peripheral blood lymphocytes at each pre- and post-vaccination time-points will be analyzed by flow cytometry for immune phenotyping and T cell subtype quantification according to standardized protocols. Breast cancer tissue analyses from the baseline biopsy and from the residual tissue obtained at definitive surgery will include: qualitative assessment of immune cell subsets such as T effectors, Tregs, NK cells, dendritic cells, macrophage subsets, B cells and expression of immune checkpoint targets such as PD-1 and PD-L1, and $iT_H2$ cells. Blood and breast cancer tissue samples will be analyzed by transcriptional profiling for changes over time including in the BIIR-described transcriptional IL-1 signature. Quantitative and avidity evaluation of tumor-infiltrating and peripheral blood cyclin B1 and patient-specific mutation, antigen-specific T cells will be carried out for patients who received anakinra versus patients who did not receive anakinra. Findings will be correlated with clinical endpoints.

Statistical Analysis of Immunologic Studies:

Continuous variables will be summarized with means or medians and standard deviations. Dichotomous and categorical variables will be summarized using counts and proportions with exact 95% confidence intervals. These summaries will be computed for each patient both pre- and post-administration of each DC vaccination. Plots will be used to show the changes in immune response over time both for each individual and for patients who received anakinra versus patients who did not receive anakinra. For each vaccination, comparisons in the pre- and 14-day post-vaccine responses will be compared using paired t-tests (or Wilcoxon signed rank tests, if appropriate) for continuous variables. McNemar's test will be used to identify significant changes in the percentage of individuals with a dichotomous characteristic pre- and post-vaccine. Associations between immune parameters will be explored graphically (e.g. scatter plots, box plots) and numerically (e.g., correlations, $\chi2$ tests). The relationships between the immune parameters and clinical outcomes (pCR rates and DFS) will be assessed using a variety of statistical techniques. Univariate and multivariate modeling will be used to quantify the associations between immune correlates, administration of anakinra versus no administration of anakinra, and clinical outcomes. In the case of a time-to-event clinical outcome (ie, DFS), the Cox proportional hazards model will be used. For binary and continuous outcomes, logistic and linear regression will be used. Kaplan-Meier techniques will be used to quantify time-t-event outcomes (DFS) and Cox proportional hazards models will be used to assess risk factors and compare subgroups of interest.

Example 3

Optimization of the Frozen Dc Vaccine Washout Protocol

Purpose:

This study was conducted to optimize the procedure to washout the frozen Dendritic Cells (DC) from the freezing solution for resuspension of the DC vaccine product for injection.

1. Background

During the testing of the control batches for breast cancer therapeutic DC vaccine product, BIIR-BrcaVax-001, it was discovered that the washout procedure was not optimal. The viability of the washed out DC was lower than anticipated (See the first two tables below). This report summarizes the work done to improve cell viability and recovery during the washout procedure as outlined in SOP VP143 "Preparing Frozen DC Vaccines for Injection".

Briefly, the original washout procedure is outlined below;

1. Thaw two vials of the frozen DC vaccine batch in normal saline and transfer the contents to sterile vacutainer tubes.
2. Centrifuge the cells in the vacutainer tubes at 270×g for 8 minutes.
3. Wash the cells a total of 3 times in normal saline.
4. Prior to spinning down the cells in the third wash step take a sample for a cell count and viability determination, as well as assessment of sterility by the endotoxin LAL assay and In-house gram stain assay.
5. After the third wash is completed, resuspend the cells in normal saline at 14×10$^6$ viable cells/mL and transfer 1 mL into a 3 mL syringe for subcutaneous injection of the patient.
6. Dilute the remaining cells in the vacutainer tube to 2×10$^6$ viable cells/mL and transfer 0.5 mL into a 1 mL syringe for intratumoral injection of the patient.
7. Send 2 mL of the remaining cell suspension to Bonfils for full sterility testing, i.e., gram stain, 14 day bacterial growth and 28 day fungal growth.

Following are the results of the testing of the first two BrcaVax-001 control batches. Presented in Table 6 and Table 7 below are the cell viability, number, and sterility of the DC vaccines at the time of the final washout step, and the stability of the DC vaccine when filled into the syringes at the cell concentrations planned for subcutaneous and intratumoral injection into the patient.

TABLE 6

Results of BrcaVax-001 control batch washout per following the procedure outlined in SOP VP143

| BrcaVax-001 Control Batch* | Pre-Wash 3† | | QC Testing In-House | | |
|---|---|---|---|---|---|
| | Viab | Conc/mL | LAL | Gram | Bonfils |
| CB1 V#7 & V#10 | 60% | $2.5 \times 10^6$/mL | Negative | Negative | Negative |
| CB2 V#7 & V#22 | 73% | $3.5 \times 10^6$/mL | Negative | Negative | Negative |

*Two control batches, CB1 and CB2, were processed and analyzed. The vial number (V#) processed from each batch is listed.
†The percentage of viable cells (Viab) and cell concentration (Conc/mL) in the sample taken prior to the third cell wash step are presented for both control batches.

TABLE 7

Stability of the BrcaVax-001 control batch DC vaccines in syringes:

| Control Batch* | 30 min/syringe† | | 1 HR/Syringe | | 2 HR/Syringe | | 3 HR/Syringe | |
|---|---|---|---|---|---|---|---|---|
| | Viab | Conc/mL | Viab | Conc/mL | Viab | Conc/mL | Viab | Conc/mL |
| CB1 $14 \times 10^6$/mL | 27% | $6.0 \times 10^6$/mL | 46% | $9.2 \times 10^6$/mL | 21% | $3.8 \times 10^6$/mL | NT | NT |
| CB1 $2 \times 10^6$/mL | 21% | $0.7 \times 10^6$/mL | 45% | $1.1 \times 10^6$/mL | 16% | $0.6 \times 10^6$/mL | NT | NT |
| CB2 $14 \times 10^6$/mL | 56% | $9.4 \times 10^6$/mL | 65% | $10.6 \times 10^6$/mL | 62% | $9.4 \times 10^6$/mL | 55% | $6.9 \times 10^6$/mL |
| CB2 $2 \times 10^6$/mL | 49% | $1.2 \times 10^6$/mL | 57% | $1.4 \times 10^6$/mL | 43% | $0.9 \times 10^6$/mL | 46% | $0.9 \times 10^6$/mL |

Note:
Large clumps of dead cells were observed in all the syringes analyzed.
*BrcaVax-001 control batches CB1 and CB2 were filled into either a 3 mL syringe at $14 \times 10^6$ viable cells/mL or a 1 mL syringe at $2 \times 10^6$ viable cells/mL according to SOP VP143.
†The DC vaccine filled syringes were held at ambient room temperature and sampled for analysis of cell viability (Viab) and concentration (Conc/mL) at the specific time points (min = minutes, and HR = hours).
NT indicates that the sample was not tested.

Conclusion: When following the original washout and resuspension procedure, the viability of the washed and resuspended DC is below the acceptable level for clinical use. Additionally, the DC vaccine is unstable in the syringes based on the low cell viability and concentrations observed at the different stability time-points.

2. Experiments

The following experiments were performed to determine what conditions were needed to optimize the viability of the washed out cells and secondly how to incorporate those conditions into a procedure appropriate for sterile washout and resuspension of patient's DC vaccine cells for injection.

Experiment 1.

The first parameter changed from the VP143 procedure was to substitute conical tubes for vacutainer tubes for washing the cells and filter the cell suspension through a 40 micron cell filter to remove clumps prior to the cell count and filling into the syringes. The results of this procedure are presented in Table 8 and Table 9 below for first the cell viability and concentration in the sample taken prior to the third wash step and second for the stability of the DC vaccine suspension in the syringes. In this experiment, only a single control batch (CB1) was tested.

TABLE 8

| BrcaVax-001 Control Batch | Pre-Wash 3 | |
|---|---|---|
| | Viab | Conc/mL |
| CB1 V#5 & V#12 | 68% | $2.5 \times 10^6$/mL |

TABLE 9

| Control Batch | 30 min/syringe | | 1 HR/syringe | |
|---|---|---|---|---|
| | Viab | Conc/mL | Viab | Conc/mL |
| CB1 $14 \times 10^6$/mL | 53% | $12.4 \times 10^6$/mL | 41% | $9.6 \times 10^6$/mL |
| CB1 $2 \times 10^6$/mL | 38% | $1.0 \times 10^6$/mL | 41% | $1.0 \times 10^6$/mL |

Note:
Large clumps of dead cells were observed in all the syringes analyzed.

Experiment 2.

The second parameter changed from the VP143 procedure was to substitute conical tubes for vacutainer tubes for washing the cells and to wash the cells in normal saline containing 50% Heat Inactivated Human AB serum (HIABS) (volume/volume of the formula mix). The results of this procedure are presented in Table 10 and Table 11 below for first the cell viability and concentration in the sample taken prior to the third wash step and second for the stability of the DC vaccine suspension in the syringes. In this experiment, only a single control batch (CB3) was tested.

TABLE 10

| BrcaVax-001 Control Batch | Pre-Wash 3 | | QC Testing In-House | | |
|---|---|---|---|---|---|
| | Viab | Conc/mL | LAL | Gram | Bonfils |
| CB3 V#3 & V#10 | 79% | $6.1 \times 10^6$/mL | Negative | Negative | Negative |

TABLE 11

| Control Batch | 30 min/syringe | | 1 HR/syringe | | 2 HR/Syringe | | 3 HR/Syringe | |
|---|---|---|---|---|---|---|---|---|
| | Viab | Conc/mL | Conc/mL | Viab | Conc/mL | Viab | Viab | Conc/mL |
| CB3 $14 \times 10^6$/mL | 80% | $8.1 \times 10^6$/mL | 72% | $6.8 \times 10^6$/mL | 78% | $3.8 \times 10^6$/mL | 85% | $1.6 \times 10^6$/mL |
| CB3 $2 \times 10^6$/mL | 78% | $0.8 \times 10^6$/mL | 73% | $0.5 \times 10^6$/mL | 62% | $0.4 \times 10^6$/mL | 44% | $0.8 \times 10^6$/mL |

Note:
Large clumps of cells were observed in all the syringes analyzed.

Conclusion: Adding HIABS to the saline greatly improved the cell viability after wash, resuspension and stability of the DC vaccine in syringes over 3 hours. The viability of the cells was more stable but there was a significant loss in cell numbers in the syringes over time. The cells were less stable in the syringe at the lower concentration of $2 \times 10^6$/mL and there was no reduction in cell clumping in the syringes.

Experiment 3.

The next modification of the procedure was to wash the cells in vacutainer tubes comparing normal saline versus normal saline+10% HIABS as the wash solution. The centrifugal force to wash the cells was reduced from 270×g to 110×g. The results of this procedure are presented in Table 12 and Table 13 below for first the cell viability and concentration in the sample taken prior to the third wash step and second for the stability of the DC vaccine suspension in the syringes. In this experiment, only a single control batch (CB3) was tested.

TABLE 12

| BrcaVax-001 | Pre-Wash 3 Normal Saline V#16 & V#18 | | Pre-Wash 3 Normal Saline + 10% HIABS V#11 & V#20 | |
|---|---|---|---|---|
| Control Batch | Viab | Conc/mL | Viab | Conc/mL |
| CB3 | 74% | $2.7 \times 10^6$/mL | 89% | $4.3 \times 10^6$/mL |

TABLE 13

| Control Batch | 1 HR/syringe | | 2 HR/Syringe | | 3 HR/Syringe | |
|---|---|---|---|---|---|---|
| | Viab | Conc/mL | Viab | Conc/mL | Viab | Conc/mL |
| CB3 NaCl $14 \times 10^6$/mL | 62% | $11.3 \times 10^6$/mL | 36% | $7.8 \times 10^6$/mL | NT | NT |
| CB3 NaCl $2 \times 10^6$/mL | 49% | $1.5 \times 10^6$/mL | 22% | $0.4 \times 10^6$/mL | NT | NT |
| CB3 NaCl + 10% HIABS $14 \times 10^6$/mL | 87% | $6.4 \times 10^6$/mL | 82% | $5.1 \times 10^6$/mL | 88% | $7.0 \times 10^6$/mL |
| CB3 NaCl + 10% HIABS $2 \times 10^6$/mL | 86% | $0.7 \times 10^6$/mL | 75% | $0.6 \times 10^6$/mL | 79% | $0.4 \times 10^6$/mL |

Note:
Small clumps of dead cells observed at 1 HR and larger clumps at 2 HR in all the syringes analyzed.

Conclusion: The cell viability was higher and more stable in preparations made with normal saline+10% HIABS and there were fewer cell clumps, but there was still a loss of cells over time. As seen in previous experiments, the viability of the cells washed in normal saline alone was unacceptable.

Experiment 4.

When the vacutainer washout procedure was originally developed, it was determined that lower centrifugation speed of 110×g was the best compromise between recovery and increased viability. The speed was increased to 270×g to maximize cell recovery, as viability was not expected to be an issue. Since cell numbers were comparable between the two speeds and cell viability was higher at lower speed, it was decided to continue all further experiments with centrifugation speeds set lower at 110×g.

The next modification to the procedure that was tested was to wash the cells in conical tubes with normal saline+ 10% HIABS, but after the second wash, the cells were incubated at ambient room temperature for 1 HR. The cells were then filtered through a 40 micron cell filter to remove cell clumps before counting the cells prior to the third wash step. The results of this procedure are presented in the Table 14, Table 15, and Table 16 below for first the cell viability and concentration in the sample taken prior to the third wash step and second for the stability of the DC vaccine suspension in the syringes. In this experiment, only a single control batch (CB2) was tested.

TABLE 14

| BrcaVax-001 | Filtered/Pre-Wash 3 Normal Saline + 10% HIABS | |
|---|---|---|
| Control Batch | Viab | Conc/mL |
| CB2 V#11 & V#18 | 89% | $3.8 \times 10^6$/mL |

TABLE 15

| Control Batch | 0 HR/Syringe | | 1 HR/Syringe | | 2 HR/Syringe | | 3 HR/Syringe | |
|---|---|---|---|---|---|---|---|---|
| | Viab | Conc/mL | Viab | Conc/mL | Viab | Conc/mL | Viab | Conc/mL |
| CB2 NaCl + 10% HIABS $14 \times 10^6$/mL | 90% | $12.6 \times 10^6$/mL | 88% | $10.9 \times 10^6$/mL | 90% | *$21.1 \times 10^6$/mL | 91% | *$1.1 \times 10^6$/mL |
| CB2 NaCl + 10% HIABS $2 \times 10^6$/mL | 89% | $1.9 \times 10^6$/mL | 81% | $1.5 \times 10^6$/mL | 86% | $1.3 \times 10^6$/mL | 87% | $1.8 \times 10^6$/mL |

*Note;
at 2 HR half of the $14 \times 10^6$/mL syringe was sampled and a large clump came out with the sample. After the 3 HR time point sample was taken and analyzed the 2 HR and 3 HR samples were combined, mixed and recounted as presented in the table below.

TABLE 16

| 2 HR and 3 HR samples combined/14 × $10^6$/mL Syringe | |
|---|---|
| Viab | Conc/mL |
| 92% | 10.9 × $10^6$/mL |

Conclusion: By this procedure the cell viability was higher and more stable over time compared to the previous methods; however, there a significant cell loss, based on lower cell concentration levels, over time for cell suspensions held in the syringes.

Experiment 5.

Since it was unlikely that HIABS was an acceptable formulation component for preparing the vaccine product for injection into patients, the next experiment was conducted where the HIABS was replaced with Heat Inactivated Autologous Serum (HIAS). In this experiment the cells were washed in conical tubes with normal saline+2% HIAS. After the cells were washed and resuspended, they were filled into glass vaccine vials, instead of a syringes, at concentrations of $14 \times 10^6$ and $2 \times 10^6$ viable cells/mL. The results of this procedure are presented in Table 17 and Table 18 below for first the cell viability and concentration in the sample taken prior to the third wash step and second the stability of the DC vaccine suspensions in the glass vaccine vials. In this experiment, only a single control batch (CB2) was tested.

TABLE 17

| BrcaVax-001 | Pre-Wash 3 Normal Saline + 2% Autologous Serum | |
|---|---|---|
| Control Batch | Viab | Conc/mL |
| CB2 V#9 & V#20 | 79% | 5.1 × $10^6$/mL |

TABLE 18

| | 0 HR/vial | | 1 HR/Vial | | 2 HR/Vial | | 3 HR/Vial | |
|---|---|---|---|---|---|---|---|---|
| Control Batch | Viab | Conc/mL | Viab | Conc/mL | Viab | Conc/mL | Viab | Conc/mL |
| CB2 NaCl + 2% HIAS 14 × $10^6$/mL | 75% | 10.8 × $10^6$/mL | 75% | 8.8 × $10^6$/mL | 62% | 5.9 × $10^6$/mL | 45% | 3.7 × $10^6$/mL |
| CB2 NaCl + 2% HIAS 2 × $10^6$/mL | 75% | 1.4 × $10^6$/mL | 51% | 1.0 × $10^6$/mL | 62% | 1.0 × $10^6$/mL | 43% | 0.3 × $10^6$/mL |

Conclusion: The cell viability after washing and resuspension in normal saline+2% HIAS was acceptable, but the cells were not stable beyond 1 hour in the glass vaccine vial. When suspended in normal saline+2% HIAS and filled in glass vaccine vials the viability and cell concentration decreased over time. The cells at the lower concentration of $2 \times 10^6$/mL were less stable than the more concentrated sample of $14 \times 10^6$/mL.

Experiment 6.

The previous experiment was repeated using a higher concentration of HIAS in the normal saline. In this experiment the cells were washed in conical tubes in normal saline+5% HIAS. The cell suspensions, at the two different cell concentrations, were filled into glass vaccine vials for stability assessment. The results of this procedure are presented in Table 19 and Table 20 below for first the cell viability and concentration in the sample taken prior to the third wash step and second for the stability of the DC vaccine suspension in the glass vaccine vials. In this experiment only a single control batch (CB2) was tested.

TABLE 19

| BrcaVax-001 | Pre-Wash 3 Normal Saline + 5% Autologous Serum | |
|---|---|---|
| Control Batch | Viab | Conc/mL |
| CB2 V#10 & v#23 | 73% | 3.5 × $10^6$/mL |

TABLE 20

| | 0 HR/vial | | 1 HR/Vial | | 2 HR/Vial | | 3 HR/Vial | |
|---|---|---|---|---|---|---|---|---|
| Control Batch | Viab | Conc/mL | Viab | Conc/mL | Viab | Conc/mL | Viab | Conc/mL |
| CB2 NaCl + 5% HIAS 14 × $10^6$/mL | 77% | 14.4 × $10^6$/mL | 73% | 11.4 × $10^6$/mL | 70% | 8.6 × $10^6$/mL | 56% | 4.6 × $10^6$/mL |
| CB2 NaCl + 5% HIAS 2 × $10^6$/mL | 72% | 1.9 × $10^6$/mL | 64% | 2.0 × $10^6$/mL | 73% | 1.4 × $10^6$/mL | 65% | 0.6 × $10^6$/mL |

Note:
No cell clumps were observed in the cell suspensions in glass vaccine vials.

Conclusion: Under these conditions the cells were slightly more stable in normal saline containing the higher concentration of HIAS compared to that in the previous experiment. However, based on the loss of cell number over time this process does not appear to give adequate stability to the DC vaccine product.

Experiment 7.

The experiment was repeated, again increasing the concentration of HIAS in the normal saline used to wash and resuspend the cells in the DC vaccine. In this experiment the cells were washed in conical tubes with normal saline+10% HIAS. The two concentrations of cell suspension were filled into glass vaccine vials for stability assessment. The results of this procedure are presented in Tables 21 and 22 below for first the cell viability and concentration in the sample taken prior to the third wash step and second for the stability of the DC vaccine suspensions in the glass vaccine vials. In this experiment only a single control batch (CB4) was tested.

TABLE 21

| BrcaVax-001 | Pre-Wash 3 Normal Saline + 10% HIABS | |
|---|---|---|
| Control Batch | Viab | Conc/mL |
| CB4 V#5 & v#6 | 78% | 4.6 × $10^6$/mL |

TABLE 22

| Control Batch | 0 HR/Vial Viab | 0 HR/Vial Conc/mL | 1 HR/Vial Viab | 1 HR/Vial Conc/mL | 2 HR/Vial Viab | 2 HR/Vial Conc/mL | 3 HR/Vial Viab | 3 HR/Vial Conc/mL |
|---|---|---|---|---|---|---|---|---|
| CB4 NaCl + 10% HIAS 14 × $10^6$/mL | 71% | 8.5 × $10^6$/mL | 70% | 5.9 × $10^6$/mL | 74% | 4.3 × $10^6$/mL | 77% | 4.0 × $10^6$/mL |
| CB4 NaCl + 10% HIAS 2 × $10^6$/mL | 73% | 1.3 × $10^6$/mL | 70% | 0.8 × $10^6$/mL | 74% | 0.8 × $10^6$/mL | 65% | 0.8 × $10^6$/mL |

Note:
No cell clumps were observed in the cell suspensions in glass vaccine vials.

Conclusion: This change did not improve DC vaccine stability, based on cell viability and concentration, beyond that observed in the previous experiment. While both heat inactivated AB serum and autologous serum improved viability of the DC vaccine above that achieved with normal saline alone, after discussion it was decided that adding serum to the formulation of the DC vaccine product is not a viable option for the clinical setting. An alternative solution to using serum was thus investigated. In the next set of experiments, different formulation options were evaluated for washing and resuspending the DC vaccines for injection. It should be noted that in the rest of the experiments presented in this report all the cell wash steps were performed in vacutainer tubes.

Experiment 8.

In this experiment the cells were washed with either normal saline+10% HIAS or Plasma-Lyte, which is an injectable electrolyte replacement. Following the wash and resuspension process the cells, at two different concentrations, were filled into glass vaccine vials for stability assessment. The results of this procedure are presented in Table 23 and Table 24 below for first the cell viability and concentration in the sample taken prior to the third wash step and second for the stability of the DC vaccine suspension in the glass vaccine vials. In this experiment only a single control batch (CB2) was tested.

TABLE 23

| BrcaVax-001 Control Batch | Pre-Wash 3 PlasmaLyte V#14 Viab | Pre-Wash 3 PlasmaLyte V#14 Conc/mL | Pre-Wash 3 Normal Saline + 10% HIABS V#24 Viab | Pre-Wash 3 Normal Saline + 10% HIABS V#24 Conc/mL |
|---|---|---|---|---|
| CB2 | 54% | 0.9 × $10^6$/mL | 84% | 2.7 × $10^6$/mL |

TABLE 24

| Control Batch | 0 HR/vial Viab | 0 HR/vial Conc/mL | 1HR/Vial Viab | 1HR/Vial Conc/mL | 2HR/Vial Viab | 2HR/Vial Conc/mL | 3HR/Vial Viab | 3HR/Vial Conc/mL |
|---|---|---|---|---|---|---|---|---|
| CB2 NaCl + 10% HIAS 14 × $10^6$/mL | 71% | 5.0 × $10^6$/mL | 70% | 2.8 × $10^6$/mL | 72% | 1.7 × $10^6$/mL | 71% | 0.9 × $10^6$/mL |
| CB2 NaCl + 10% HIAS 2 × $10^6$/mL | 64% | 1.2 × $10^6$/mL | 74% | 0.8 × $10^6$/mL | 67% | 0.6 × $10^6$/mL | 68% | 0.3 × $10^6$/mL |
| CB2 Plasma-Lyte 14 × $10^6$/mL | 45% | 10.8 × $10^6$/mL | NT | NT | NT | NT | NT | NT |
| CB2 Plasma-Lyte 2 × $10^6$/mL | 36% | 1.3 × $10^6$/mL | NT | NT | NT | NT | NT | NT |

Note:
No cell clumps were observed in the cell suspensions in glass vaccine vials.

Conclusion: The results of this experiment clearly demonstrate that the cells were more stable, based on cell viability, when washed and resuspended in normal saline+ 10% HIAS compared to Plasma-Lyte. Clearly, with regard to cell viability, cell number and stability it is unacceptable to use Plasma-Lyte in this process. At this point in the study, due to the limited availability of autologous serum for the current control batches, future experiments did not use serum to compare to other formulation alternatives for the washout and resuspension solution.

Experiment 9.

In this experiment the cells were washed with normal saline+1% Dextrose. Cell Viability and cell numbers were compared after 1, 2 and 3 washes. Stability analysis was conducted on cell suspensions, at two different concentrations, filled into glass vaccine vials. The results of this procedure are presented in Table 25 and Table 26 below for first the cell viability and concentration in the samples taken prior to each of the wash steps and second for the stability of the DC vaccine suspension in glass vaccine vials. In this experiment only a single control batch (CB2) was tested.

TABLE 25

| BrcaVax-001 Control Batch | Normal Saline + 1% Dextrose Viab | Normal Saline + 1% Dextrose Conc/mL |
|---|---|---|
| CB2 V#13 Pre-Wash 1 | 82% | 3.1 × $10^6$/mL |
| CB2 V#3 Pre-Wash 2 | 62% | 1.3 × $10^6$/mL |
| CB2 V#17 Pre-Wash 3 | 54% | 1.3 × $10^6$/mL |

TABLE 26

| Control Batch | 15 Min/vial Viab | 15 Min/vial Conc/mL | 30 Min/Vial Viab | 30 Min/Vial Conc/mL | 45 Min/Vial Viab | 45 Min/Vial Conc/mL | 1 HR/Vial Viab | 1 HR/Vial Conc/mL |
|---|---|---|---|---|---|---|---|---|
| 1 wash $14 \times 10^6$/mL | 71% | $9.2 \times 10^6$/mL | 77% | $7.2 \times 10^6$/mL | 60% | $7.6 \times 10^6$/mL | 64% | $6.2 \times 10^6$/mL |
| 1 wash $2 \times 10^6$/mL | 70% | $1.1 \times 10^6$/mL | 54% | $0.8 \times 10^6$/mL | 61% | $0.6 \times 10^6$/mL | 60% | $0.9 \times 10^6$/mL |
| 2 washes $14 \times 10^6$/mL | 61% | $11.2 \times 10^6$/mL | 58% | $9.8 \times 10^6$/mL | 51% | $8.4 \times 10^6$/mL | 45% | $7.7 \times 10^6$/mL |
| 2 washes $2 \times 10^6$/mL | 45% | $0.8 \times 10^6$/mL | 48% | $1.1 \times 10^6$/mL | 29% | $0.6 \times 10^6$/mL | 19% | $0.4 \times 10^6$/mL |
| 3 washes $14 \times 10^6$/mL | 68% | $10.0 \times 10^6$/mL | 52% | $9.2 \times 10^6$/mL | 68% | $11.8 \times 10^6$/mL | 60% | $11.7 \times 10^6$/mL |
| 3 washes $2 \times 10^6$/mL | 56% | $1.1 \times 10^6$/mL | 49% | $1.0 \times 10^6$/mL | 62% | $1.3 \times 10^6$/mL | 51% | $0.8 \times 10^6$/mL |

Note:
No cell clumps were observed in the cell suspensions in glass vaccine vials.

Conclusion: For cells washed and suspended in normal saline+1% dextrose the cell viability and cell numbers were acceptable prior to the first wash but cell viability and numbers declined significantly with each additional wash step. A single wash will not be acceptable because a minimum of two washes are required to wash and combine 2 frozen DC vaccine vials for processing the final vaccine product for injection. Therefore, all future experiments were conducted with a minimum of two washes.

Experiment 10:

This experiment was a repeat of the process followed in experiment 9 above. It was done to assess a 10-fold higher concentration of dextrose with two washes using 2 frozen vaccine vials. The cells were washed with normal saline+10% Dextrose. Stability testing was conducted on cell suspensions filled into glass vaccine vials. The results of this procedure are presented in Table 27 and Table 28 below for first the cell viability and concentration in the sample taken prior to the second wash step and second for the stability of the DC vaccine suspensions, at two concentrations, in glass vaccine vials. In this experiment only a single control batch (CB2) was tested.

TABLE 27

| BrcaVax-001 Control Batch | Pre-Wash 2 Normal Saline + 10% Dextrose Viab | Pre-Wash 2 Normal Saline + 10% Dextrose Conc/mL |
|---|---|---|
| CB2 V#4 & v#6 | 57% | $2.4 \times 10^6$/mL |

TABLE 28

| Control Batch | 15 Min/vial Viab | 15 Min/vial Conc/mL | 30 Min/Vial Viab | 30 Min/Vial Conc/mL |
|---|---|---|---|---|
| CB2 NaCl + 10% Dextrose $14 \times 10^6$/mL | 51% | $11.6 \times 10^6$/mL | 44% | $7.1 \times 10^6$/mL |
| CB2 NaCl + 10% Dextrose $2 \times 10^6$/mL | 42% | $0.7 \times 10^6$/mL | 35% | $0.5 \times 10^6$/mL |

Note:
No cell clumps were observed in the cell suspensions in glass vaccine vials.

Conclusion: Based on the low cell viability normal saline plus 10% Dextrose is considered to be unacceptable for formulating the DC vaccine product for injection.

Experiment 11.

In this experiment, the cells were washed with normal saline+5% Dextrose+1% amino acid solution (AA). Results are in Table 29 below. Because the cell viability was so low after the first wash (see results in table below) it was decided to not pursue the DC vaccine stability assessment using this formulation.

TABLE 29

| BrcaVax-001 Control Batch | Pre-Wash 2 Normal Saline + 5% Dextrose + 1% AA Viab | Pre-Wash 2 Normal Saline + 5% Dextrose + 1% AA Conc/mL |
|---|---|---|
| CB2 V#2 & v#16 | 24% | $2.1 \times 10^6$/mL |

Conclusion: The wash solution consisting of normal saline/5% dextrose/1% AA was considered unacceptable for processing the DC vaccine for injection. It should be noted; however, that the failure of this formulation could be due to the low pH of the solution, since the pH of the NaCl+5% Dex+1% amino acid solution was found to be 4.0-4.5 using pH test strips.

Experiment 12.

In this experiment, the cells were washed with 1× Phosphate Buffered Saline (PBS). Three washes were preformed with a cell count performed prior to the second and third washes. In Table 30 below the cell viability and number is presented for sample analyzed prior to the initiation of the second and third wash steps. Stability testing of the DC vaccine was not performed using PBS to resuspend the cells.

TABLE 30

| BrcaVax-001 Control Batch | 1X PBS Viab | 1X PBS Conc/mL |
|---|---|---|
| CB2 V#5 Pre-Wash 2 | 70% | $1.9 \times 10^6$/mL |
| CB2 V#5 Pre-Wash 3 | 50% | $1.5 \times 10^6$/mL |

Conclusion: 1×PBS offers no additional benefit over normal saline as the wash buffer for preparing the DC vaccine for injection.

Experiment 13.

In the next experiment fresh DC vaccine prepared after harvest of the cells from the culture bags was suspended at three different concentrations in normal saline and filled into syringes for stability testing (see results in Table 31 below). This experiment was conducted with a single control batch of DC vaccine (CB6).

TABLE 31

| Control | 1 HR/syringe | | 2 HR/syringe | |
|---|---|---|---|---|
| Batch 6 | Viab | Conc/mL | Viab | Conc/mL |
| $5 \times 10^6$/mL | 81% | $5.4 \times 10^6$/mL | 91% | $4.0 \times 10^6$/mL |
| $10 \times 10^6$/mL | 93% | $15.5 \times 10^6$/mL | 89% | $9.3 \times 10^6$/mL |
| $15 \times 10^6$/mL | 89% | $16.3 \times 10^6$/mL | 89% | $14.6 \times 10^6$/mL |

Experiment 39.

Experiment 13 was repeated using Lactated Ringer's to wash and resuspend the cells for stability testing. Cell suspensions, prepared with cells from control batch 7, were filled into a glass vaccine vials for stability testing (see results in Table 32 below).

TABLE 32

| Control | 1 HR/Vial | | 2 HR/Vial | | 64 HR/Vial | |
|---|---|---|---|---|---|---|
| Batch 7 | Viab | Conc/mL | Viab | Conc/mL | Viab | Conc/mL |
| Sample 1 | 93% | $3.8 \times 10^6$/mL | 89% | $2.7 \times 10^6$/mL | NT | NT |
| Sample 2 | 94% | $4.3 \times 10^6$/mL | 92% | $4.2 \times 10^6$/mL | NT | NT |
| Sample 3 | 96% | $5.2 \times 10^6$/mL | 91% | $3.8 \times 10^6$/mL | 68% | $2.4 \times 10^6$/mL |

Experiment 15.

In this experiment, a batch of fresh DC vaccine was prepared with cells harvested in either normal saline or Lactated Ringer's. Samples of the fresh DC vaccine preparations were removed and filled in glass vaccine vials for stability assessment (see Table 33 below). The remainder of the batch was frozen in glass vaccine vials per the standard protocol.

TABLE 33

| Control Batch 8 | 0 HR/Vial | | 2 HR/Vial | | 3 HR/Vial | | 4 HR/Vial | | 19.5 HR/Vial | |
|---|---|---|---|---|---|---|---|---|---|---|
| Fresh DC | Viab | Conc/mL | Viab | Conc/mL | Viab | Conc/mL | Viab | Conc/mL | Viab | Conc/mL |
| Harvest Normal Saline | 91% | $4.2 \times 10^6$/mL | 83% | $2.6 \times 10^6$/mL | 77% | $2.6 \times 10^6$/mL | 75% | $1.9 \times 10^6$/mL | 27% | $0.8 \times 10^6$/mL |
| Harvest Ringers | 90% | $1.8 \times 10^6$/mL | 84% | $1.1 \times 10^6$/mL | 82% | $1.1 \times 10^6$/mL | 74% | $0.9 \times 10^6$/mL | 81% | $1.1 \times 10^6$/mL |

Note;
Initial cell concentrations of the cell suspensions were different in the two formulation samples as shown at time zero in the table.

Conclusion: The cells harvested in the Lactated Ringer's solution are more stable than those processed in normal saline. There is much less cell loss over time in Lactated Ringer's suspensions compared to that in normal saline and after 19 hours the cells suspended in Lactated Ringer's were still very viable compared to those in normal saline which were mostly dead.

Compared to the reprocessed, frozen DC vaccines analyzed above, the fresh DC vaccine preparations were more stable, displaying both higher cell viability and cell numbers over time. While this is encouraging, it should be cautioned that manufacturing fresh vaccine batches for the proposed cancer therapy clinical trials is not feasible. Therefore, the efforts were put back into improving the process for preparing the frozen DC vaccines for injection.

Experiment 16.

In the next experiment the cells were washed with either normal saline or Lactated Ringer's. For this experiment USP injectable Lactated Ringer's was tested as a clinically acceptable formula for thawing, washing and resuspending the DC vaccines prior to injection. The cell suspensions were filled in either syringes or glass vaccine vials for stability testing. The results of this procedure are presented in Table 34 and Table 35 below for first the cell viability and concentration in the sample taken prior to the second wash step and second for the stability of the DC vaccine suspensions in glass vaccine vials and syringes. In this experiment only a single control batch (CB6) was tested.

TABLE 34

| BrcaVax-001 | Pre-Wash 2 Normal Saline V#11 | | Pre-Wash 2 Lactated Ringer's v#4 | |
|---|---|---|---|---|
| Control Batch | Viab | Conc/mL | Viab | Conc/mL |
| CB6 | 50% | $1.6 \times 10^6$/mL | 65% | $2.7 \times 10^6$/mL |

TABLE 35

| Control | 1 HR | | 2 HR | | 3 HR | |
|---|---|---|---|---|---|---|
| Batch 6 | Viab | Conc/mL | Viab | Conc/mL | Viab | Conc/mL |
| NaCl $8 \times 10^6$/mL Vial | 63% | $11.9 \times 10^6$/mL | 40% | $6.0 \times 10^6$/mL | 55% | $9.3 \times 10^6$/mL |
| NaCl $8 \times 10^6$/mL Syringe | 71% | $10.4 \times 10^6$/mL | 63% | $11.1 \times 10^6$/mL | 61% | $9.4 \times 10^6$/mL |
| Lactated Ringer's $10 \times 10^6$/mL Vial | 75% | $6.7 \times 10^6$/mL | 69% | $8.7 \times 10^6$/mL | 66% | $7.7 \times 10^6$/mL |
| Lactated Ringer's $10 \times 10^6$/mL Syringe | 75% | $8.7 \times 10^6$/mL | 50% | $3.2 \times 10^6$/mL | 67% | $7.3 \times 10^6$/mL |

Conclusion: Cells washed and resuspended in Lactated Ringer's had slightly higher viability compared to those processed in normal saline. Regardless of the wash/suspension media the cell numbers and viability of the cells suspensions were comparable between syringes and vials.

Experiment 17.

In a follow up experiment, the cells were washed and resuspended with Lacated Ringer's and filled in either a syringe or a glass vaccine vial for stability testing. The results of this procedure are presented in Table 36 and Table 37 below for first the cell viability and concentration in the sample taken prior to the second wash step and second for the stability of the DC vaccine suspensions in syringes and glass vaccine vials. In this experiment only a single control batch (CB6) was tested.

TABLE 36

| BrcaVax-001 | Pre-Wash 2 Lactated Ringer's | |
|---|---|---|
| Control Batch | Viab | Conc/mL |
| CB6 V#2 & v#6 | 83% | $5.6 \times 10^6$/mL |

TABLE 37

| Control | 1 HR | | 2 HR | | 3 HR | |
|---|---|---|---|---|---|---|
| Batch 6 | Viab | Conc/mL | Viab | Conc/mL | Viab | Conc/mL |
| Lactated Ringer's $8 \times 10^6$/mL Vial | 78% | $7.7 \times 10^6$/mL | 79% | $6.2 \times 10^6$/mL | 62% | $4.5 \times 10^6$/mL |
| Lactated Ringer's $8 \times 10^6$/mL Syringe | 76% | $7.2 \times 10^6$/mL | 71% | $5.6 \times 10^6$/mL | 66% | $4.0 \times 10^6$/mL |

Conclusion: In Lactated Ringer's solution, the DC had higher cell viability and were more stable. The stability of the cell suspensions in syringes and vials were comparable. The benefit of using the glass vaccine vials over the syringes is that the vial is a more secure way to transport the cells to the clinic as a syringe has a plunger that could be bumped or otherwise depressed and result in a loss of volume in the syringe.

Experiment 18.

In this experiment, cells were washed and resuspended in either Lactated Ringer's or normal saline. Stability was conducted on cell suspensions filled into glass vaccine vials. The results of this procedure are presented in Table 38 and Table 39 below for first the cell viability and concentration in the sample taken prior to the second wash step and second for the stability of the DC vaccine suspension in the glass vaccine vials. In this experiment only a single control batch (CB6) was tested.

TABLE 38

| BrcaVax-001 | Pre-Wash 2 Normal Saline V#7 & V#9 | | Pre-Wash 2 Lactated Ringer's V#1 & V#15 | |
|---|---|---|---|---|
| Control Batch | Viab | Conc/mL | Viab | Conc/mL |
| CB6 | 80% | $4.5 \times 10^6$/mL | 81% | $6.3 \times 10^6$/mL |

TABLE 39

| Control | 1 HR/Vial | | 2 HR/Vial | | 3 HR/vial | |
|---|---|---|---|---|---|---|
| Batch 6 | Viab | Conc/mL | Viab | Conc/mL | Viab | Conc/mL |
| NaCl $14 \times 10^6$/mL | 65% | $12.5 \times 10^6$/mL | 56% | $9.8 \times 10^6$/mL | 50% | $8.4 \times 10^6$/mL |
| NaCl $2 \times 10^6$/mL | 56% | $1.4 \times$ mL | 42% | $1.1 \times$ mL | 49% | $1.2 \times$ mL |
| Lactated Ringer's $14 \times 10^6$/mL | 78% | $8.4 \times 10^6$/mL | 80% | $9.7 \times 10^6$/mL | 74% | $10.7 \times 10^6$/mL |
| Lactated Ringer's $2 \times 10^6$/mL | 78% | $1.4 \times 10^6$/mL | 73% | $1.3 \times 10^6$/mL | 72% | $1.1 \times 10^6$/mL |

Conclusion: Cell viability and cell number stability in the glass vaccine vial was higher for the cell suspension prepared in Lactated Ringer's than in normal saline.

It should be noted that when Vial #1 and Vial #15 (that is, vials thawed for washing the cells in Lactated Ringer's) were combined and sampled for a cell count and viability, a sample was taken for an in-house gram stain assay and a PTS LAL Assays. Both assays were negative for microbial contamination.

Experiment 19.

A different control batch of DC vaccine (CB7) was used to repeat a portion of experiment 17 above. That is, the cells were washed and resuspended with Lactated Ringer's. The cell suspension at two concentrations was filled into glass vaccine vials for stability testing. The results of this procedure are presented in Table 40 and Table 41 below for first the cell viability and concentration in the sample taken prior to the second wash step and second for the stability of the DC vaccine suspensions in glass vaccine vials. In this experiment only a single control batch (CB7) was tested.

TABLE 40

| BrcaVax-001 | Pre-Wash 2 Lactated Ringer's | |
|---|---|---|
| Control Batch | Viab | Conc/mL |
| CB7 V#1 & V#8 | 68% | $3.5 \times 10^6$/mL |

TABLE 41

| Control | 1 HR/Vial | | 2 HR/Vial | | 3 HR/vial | |
|---|---|---|---|---|---|---|
| Batch 7 | Viab | Conc/mL | Viab | Conc/mL | Viab | Conc/mL |
| Lactated Ringer's $14 \times 10^6$/mL | 64% | $10.3 \times 10^6$/mL | 65% | $13.0 \times 10^6$/mL | 59% | $13.0 \times 10^6$/mL |
| Lactated Ringer's $2 \times 10^6$/mL | 63% | $1.4 \times 10^6$/mL | 58% | $1.3 \times 10^6$/mL | 57% | $1.1 \times 10^6$/mL |

Conclusion: Despite the overall low starting cell viability of this control batch, its stability in the glass vaccine vial was encouraging, especially for cells suspended at the higher concentration. In this experiment both the cell viability and number were stable for about 3 hours in the cell suspension prepared at a concentration of $14 \times 10^6$ viable cells/mL.

As in experiment 17, when Vial #1 and Vial #8 were thawed, washed and combined, and sampled for a cell count and viability, a sample was taken for an in-house gram stain assay and a PTS LAL Assays. Both assays were negative for microbial contamination.

Experiment 20.

The frozen vaccine vials from batch 8 processed in experiment 15 were thawed and washed in Lactated Ringer's. Two conditions were tested, with the first being the frozen vials that were harvested by washing in normal saline and the second being the frozen vaccine that was harvested and washed in Lactated Ringer's prior to freezing in vaccine vials. After washing and resuspending the cells in Lactated Ringer's the cell suspension at $15\times10^6$ viable cells/mL was filled into glass vaccine vials for stability testing. The results of this experiment are presented in Table 42 and Table 43 below for first the cell viability and concentration in the sample taken prior to the second wash step and second for the stability of the DC vaccine suspension in glass vaccine vials. In this experiment only a single control batch (CB8) was tested.

TABLE 42

| BrcaVax-001 | Pre-Wash 2 Harvest in Normal Saline V#20 & V#21 | | Pre-Wash 2 Harvest in Lactated Ringer's V#2 & V#9 | |
|---|---|---|---|---|
| Control Batch | Viab | Conc/mL | Viab | Conc/mL |
| CB8 | 83% | $4.8 \times 10^6$/mL | 90% | $2.6 \times 10^6$/mL |

TABLE 43

| Control Batch 8 | 1 HR/Vial | | 2 HR/Vial | | 3 HR/Vial | | 4 HR/Vial | |
|---|---|---|---|---|---|---|---|---|
| Washed DC | Viab | Conc/mL | Viab | Conc/mL | Viab | Conc/mL | Viab | Conc/mL |
| Harvest Normal Saline | 73% | $15.5 \times 10^6$/mL | 74% | $7.2 \times 10^6$/mL | 65% | $6.9 \times 10^6$/mL | 50% | $4.7 \times 10^6$/mL |
| Harvest Lactated Ringer's | 78% | $21.0 \times 10^6$/mL | 68% | $13.7 \times 10^6$/mL | 64% | $12.2 \times 10^6$/mL | 57% | $9.6 \times 10^6$/mL |

Conclusion: Comparable stability of the cell suspensions in Lactated Ringer's was observed, regardless of whether the cells were harvested and washed prior to freezing in normal saline or Lactated Ringer's. While the cell viability was comparable at the different stability test time-points, the cell number appeared to be more stable for cell suspension that was prepared with cells that had been harvested in Lactated Ringer's.

Both conditions were tested for an in-house gram stain assay and a PTS LAL Assays. Both samples tested negative for endotoxin by LAL and negative for organisms in the in-house gram stain.

Experiment 21.

In the next set of experiments, we used the conditions that are believed to be the best way to optimize the current washout procedure in a clinically appropriate way to test control batches 1 through 4. The frozen DC vaccines were thawed, transferred into vacutainer tubes and washed twice in Lactated Ringer's solution. The cells were suspended in Lactated Ringer's at $15\times10^6$ viable cells/mL and filled into glass vaccine vials for stability testing. The results of this procedure are presented in Table 44 and Table 45 below for first the cell viability and concentration in the sample taken prior to the second wash step and second for the stability of the DC vaccine suspensions in the glass vaccine vials. The samples taken prior to the second wash step were also analyzed for the presence of endotoxin and gram-positive organisms.

TABLE 44

| BrcaVax-001 Control Batch | Pre-Wash 2 Lactated Ringers | | QC Testing In-House | |
|---|---|---|---|---|
| | Viab | Conc/mL | LAL | Gram |
| CB 1 V3 & V11 | 75% | $4.3 \times 10^6$/mL | Negative | Negative |
| CB 2 V1 & V12 | 85% | $5.3 \times 10^6$/mL | Negative | Negative |
| CB 3 V5 & V13 | 80% | $3.8 \times 10^6$/mL | Negative | Negative |
| CB 4 V4 & V9 | 70% | $5.5 \times 10^6$/mL | Negative | Negative |

TABLE 45

| Ringers 15 × $10^6$/mL Vial | 1 HR/Vial | | 2 HR/Vial | | 3 HR/Vial | | 4 HR/Vial | |
|---|---|---|---|---|---|---|---|---|
| | Viab | Conc/mL | Viab | Conc/mL | Viab | Conc/mL | Viab | Conc/mL |
| CB1 V3 & V11 | 65% | $9 \times 10^6$/mL | 76% | $10.7 \times 10^6$/mL | 78% | $11.2 \times 10^6$/mL | 62% | $7.6 \times 10^6$/mL |
| CB2 V1 & 12 | 79% | $10.3 \times 10^6$/mL | 79% | $9.9 \times 10^6$/mL | 75% | $9.6 \times 10^6$/mL | 63% | $8.3 \times 10^6$/mL |
| CB3 V5 & V13 | 82% | $10.5 \times 10^6$/mL | 68% | $9.5 \times 10^6$/mL | 79% | $8.4 \times 10^6$/mL | 74% | $8.8 \times 10^6$/mL |
| CB4 V4 & V9 | 77% | $10.2 \times 10^6$/mL | 77% | $10.7 \times 10^6$/mL | 77% | $9.5 \times 10^6$/mL | 69% | $9.0 \times 10^6$/mL |

Conclusion: The viability and cell number are acceptable when the DC vaccine cells are washed twice in vacutainer tubes with Lactated Ringer's solution. The viability of the cells in the glass vaccine vials over time support a 2 HR expiration time (from the time the cells are put into a sterile glass vaccine vial at a concentration of $15\times10^6$ viable cells/mL).

Comparing the results of Experiment 21 in Table 44 and Table 45 with the results from the original washout protocol in Table 6 and Table 7, it is clear that washing twice in vacutainer tubes, at slower speeds with Lactated Ringer's and filling the DC vaccine at a higher dose into a sterile glass vaccine vial improves the cell viability and cell number stability of the vaccine product.

3. Summary

The experiments done in this study support a number of conclusions, which include:
  DC vaccine cell viability and recovery is improved when the vaccine product is prepared at higher cell concentrations.
  DC vaccine cell viability and recovery is increased and cell clumping is decreased when the cells suspension is filled into glass vaccine vials rather than syringes.
  Glass vaccine vials is a more secure way to transport the cell suspension of the vaccine product to the clinic and provides more flexibility in dosing the patient.

When Lactated Ringer's solution is used to prepare the vaccine product for injection it increases the cell viability and stability of the cells over time compared to normal saline.

Recommendation:

From these conclusions, it was decided to revise the original washout and resuspension procedure in the following ways:

Thaw and wash the Frozen DC vaccines with Lactated Ringer's.

Prepare the cells at a concentration of $15 \times 10^6$ viable cells/mL in Lactated Ringer's.

Fill a glass vaccine vial for use by the clinic to vaccinate patients enrolled in approved clinical trials.

Example 4: Prophetic Example

Pilot Safety and Blood Immune Cell Transcriptional Profiling Study of Anakinra Plus the Physician's Chemotherapy of Choice in Metastatic Breast Cancer Patients 1. Introduction A. Background on Breast Cancer Breast cancer is a genetically heterogenous and biologically diverse disease. Although the treatment of metastatic breast cancer has improved, the disease remains incurable. One of the most active first-line regimens for patients with Her2-negative metastatic breast cancer (MBC) is the combination of weekly paclitaxel and bevacizumab. In a Phase III trial, the addition of bevacizumab to weekly paclitaxel resulted in a longer progression free survival (PFS) (11.8 months vs. 5.9 months) and higher response rate (50% vs. 25%) than paclitaxel alone (Miller 2007). However, further improvement in the efficacy of treatment is necessary.

B. IL-1 and Pro-Tumor Inflammation in Breast Cancer

The IL-1 family plays an important role in inflammation and host defense. Up to 11 members have been identified to date (Smith 2000). IL-1α and IL-1β are proinflammatory cytokines. IL-1α is primarily bound to the membrane whereas IL-1β is secreted (Dinarello 2005a, Andre 2010). There are 2 transmembrane IL-1 receptors, types I and II. The type II IL-1 receptor does not signal and is a decoy receptor for IL-1β. IL-1Ra is an endogenous receptor antagonist. IL-1Ra is predominantly produced by activated monocytes and macrophages. The IL-1Ra does not bind to the type II receptor but rather primarily to the type I receptor, which is the signaling receptor.

Recently, it has been suggested that tumor microenvironment plays a role in cancer progression and chemotherapy drug resistance. Cells in the tumor microenvironment can stimulate cancer cell growth and invasion (Andre 2010). Solid tumors are often associated with aseptic inflammation. There are 2 types of inflammation that have opposing effects on tumors, chronic inflammation that promotes cancer cell survival, and metastasis, and acute inflammation which triggers cancer cell destruction. Chronic inflammation is often linked with the presence of type 2-polarized macrophages (M2), which are induced by Th2 cytokines, IL-4 and IL-13. It is evident that there is a functional relationship between chronic inflammation and cancer (Bhowmick 2004), and it is thought that carcinogenesis may be promoted by the polarization of M2 tumor-associated macrophages via cytokines and production of growth factors. In metastatic breast cancer, IL-1 has been shown to be up regulated, and patients with IL-1-producing tumors have generally poor prognoses (Lewis 2006). IL-1 is known to be a strong inducer of IL-6 (Linkhart 1991), which in turn leads to M2 macrophage polarity, secretion of pro-growth factors, ultimately creating an environment that favors tumor progression (DeNardo 2007).

Recent studies have demonstrated the presence of inflammatory Th2 cells in breast cancers, which produce IL-13, IL-4, and TNF (Aspord 2007). These CD4+ T cells appear to play a key role in the disease as they accelerate breast tumor development in a xenograft model through the production of IL-13. Breast cancers appear to play a critical role in conditioning the infiltrating myeloid DCs (mDCs) to induce such inflammatory Th2 cells. It has also been shown that thymic stromal lymphopoietin (TSLP) secreted by cancer cells plays a role in mDCs conditioning (Pedroza-Gonzalez 2011). Breast cancer cell lines and primary tumors from patients show TSLP protein expression. TSLP-neutralizing antibodies block the upregulation of OX40L by mDCs exposed to tumor supernatant and consequently block mDCs capacity to generate inflammatory Th2 cells in vitro (Pedroza-Gonzalez 2011).

Recent studies show crosstalk between breast cancer cells and mDCs which triggers high level of IL-1β production, which feeds back on cancer cells to induce high TSLP secretion. Higher IL-1β levels correspond with higher clinical stage of the tumor indicating the potential prognostic value of IL-1β. When measuring IL-1 alpha in tumors from patients, however, the levels of IL-1 beta are substantially higher. Furthermore, no difference was found in the levels of IL-1 alpha between tumors and surrounding macroscopically uninvolved tissue. The current hypothesis is that IL-1β is produced by myeloid infiltrate whereas IL-1 alpha is most likely produced by cancer cells. Studies show that treatment with the IL-1R antagonist, anakinra, prevents tumor development in vivo in humanized mice model of breast cancer.

C. Fatigue Caused by IL-1 in Cancer Patients

Patients undergoing chemotherapy frequently experience symptoms of fatigue, which has been attributed to the increase in proinflammatory cytokines such as IL-1β (Wood 2006). This symptom can be attributed not only to therapeutic intervention, such as chemotherapy, but also inherent to cancer itself (Kurzrock 2001). IL-1 has been associated with factors that contribute towards fatigue, such as anemia, weight loss, fever, and infection (Kurzrock 2001), and is among several molecules that could be targetable to reduce cancer-related fatigue.

D. Background on Anakinra (Kineret®)

Anakinra is a recombinant soluble non-glycosylated homolog of human IL-1Ra that competitively inhibits binding of IL-1α and IL-1β to the receptor type I (Dinarello 2005b). Anakinra was approved in 2001 as a treatment for adult rheumatoid arthritis patients whose disease has progressed on one or more disease-modifying anti-rheumatic drugs. The approved adult dose is 100 mg administered daily as a subcutaneous (SC) injection. With this dose, anakinra has a favorable safety profile; the most common adverse reaction is injection site reaction. The uncommon serious adverse reactions included an increased incidence of serious infections. Anakinra has been used in large clinical trials of adults and children (Gartlehner 2006). It resulted in improvement and/or resolution of clinical manifestations, hematological and biochemical changes in patients with inherited chronic inflammatory diseases affecting IL-1 production (Hawkins 2004, Hoffman 2004, Goldbach-Mansky 2006). When administered to pediatric patients with Systemic Onset Juvenile Idiopathic Arthritis (SOJIA), anakinra treatment resulted in remarkable clinical and hematological responses in >70% of patients, and it was accompanied by a steroid-sparing effect (Pascual 2005). Resolution of clinical symptoms including fever, marked leukocytosis, thrombocytosis, anemia, elevated ESR and arthritis were rapid and sustained (Pascual 2005). These results have now been confirmed in randomized clinical trials.

E. Background on Standard of Care Agents for Metastatic Disease

Nanoparticle albumin-bound (nab) paclitaxel, capecitabine, eribulin, and vinorelbine are standard, FDA approved effective cytotoxic agents for MBC that are minimally myelosuppressive and do not require steroid premedication. All treatments were approved based on Phase III clinical trials whose data determined their efficacy in this setting (Gradishar 2005, Blum 2007, Cortes 2011, Blum 1999, Jones 1995).

F. Rationale

In an attempt to reverse the immune suppressive microenvironment and to enhance chemotherapy effectiveness, decrease tumor metastagenicity and decrease IL-1-induced fatigue, metastatic breast cancer (MBC) patients will be treated with chemotherapy plus anakinra. In this pilot safety, single arm, open label trial, we plan to determine the safety of anakinra plus the physician's chemotherapy choice (TPC) of nab paclitaxel, capecitabine, eribulin, or vinorelbine in patients with MBC and to define an anakinra-induced anti-IL-1 whole blood transcriptional profile.

2. Trial Objectives

A. Primary Objectives

The objective of this protocol is to assess the safety profile of the IL-1 receptor antagonist, anakinra, plus TPC of nab paclitaxel, capecitabine, eribulin, or vinorelbine in patients with MBC.

B. Secondary Objectives

The secondary objectives of this protocol are to determine investigator-assessed objective response rate, clinical benefit rate, progression-free survival, and rates of chemotherapy or cancer-related anemia (HgB<10), and an anakinra-induced anti-IL-1 blood transcriptional signatures in patients who undergo IL-1 receptor blockade therapy.

3. Study Design

This pilot safety, single arm, open label trial will evaluate the impact of adding anakinra to TPC of nab paclitaxel, capecitabine, eribulin, or vinorelbine in the treatment of patients with HER2-negative MBC. Patients starting chemotherapy at the time of study enrollment will undergo a 2-week run-in treatment of anakinra alone, 100 mg SC daily, followed by anakinra plus TPC of standard of care (SOC) nab paclitaxel, capecitabine, eribulin, or vinorelbine. Patients enrolling in the study who are currently being treated with nab paclitaxel, capecitabine, eribulin, or vinorelbine will not undergo the anakinra run-in treatment. These patients will begin administration with anakinra on Day 1 of the next chemotherapy cycle. End of Study will occur 6 months after the first dose of anakinra is administered, or at early withdrawal, whichever occurs first. After 6 months, patients may continue their SOC treatment alone until disease progression or intolerable toxicity. The use of corticosteroids as an antiemetic is strongly discouraged to be able to evaluate anakinra's effects on patients' well being, energy level, and on plasma cytokines and other immunologic biomarkers.

Whole blood for immunologic biomarkers will be obtained: prior to treatment on Day −14 Cycle 0, after the 2-week run-in with anakinra for those patients starting chemotherapy at the time of study enrollment, and monthly thereafter after initiation of anakinra/TPC of nab paclitaxel, capecitabine, eribulin, or vinorelbine for all patients.

4. Therapeutic Agents

A. Anakinra (Kineret or Equivalent; Kineret 2009)

Anakinra is a recombinant, nonglycosylated form of the human interleukin-1 receptor antagonist (IL-1Ra). Anakinra differs from native human IL-1Ra in that it has the addition of a single methionine residue at its amino terminus. It is produced by recombinant DNA technology using an *E coli* bacterial expression system.

Anakinra is indicated for the reduction in signs and symptoms and slowing the progression of structural damage in moderately to severely active rheumatoid arthritis, in patients 18 years of age or older who have failed 1 or more disease modifying antirheumatic drugs (DMARDs). Anakinra can be used alone or in combination with DMARDs, other than TNF blocking agents (see Section 5.1).

Anakinra consists of 153 amino acids and has a molecular weight of 17.3 kilodaltons. Anakinra is supplied in single use prefilled glass syringes with 27 gauge needles as a sterile, clear, colorless-to-white, preservative-free solution for daily subcutaneous (SC) administration. The solution may contain trace amounts of small, translucent-to-white amorphous proteinaceous particles. Each prefilled glass syringe contains: 0.67 mL (100 mg) of anakinra in a solution (pH 6.5) containing sodium citrate (1.29 mg), sodium chloride (5.48 mg), disodium EDTA (0.12 mg), and polysorbate 80 (0.70 mg) in Water for Injection, USP.

B. Physician's Chemotherapy Choice of MBC Agents

Selection of TPC cytotoxic agent will be based on what agent would have been offered to the patient, should he or she not be participating in the trial. TPC agents are limited to nab paclitaxel, eribulin, capecitabine, or vinorelbine, and the use of corticosteroids as antiemetics are discouraged in order to assess possible beneficial effects of anakinra on patients' well being.

Preparation and administration will be followed per the site's guidelines and standard FDA labeling. The doses to be used for TPC drug products are below:

Nab paclitaxel: 100 mg/m$^2$ administered IV weekly (Day 1, 8, and 15 every 28 days)

Eribulin: 1.4 mg/m$^2$ administered IV weekly (Day 1 and 8 every 21 days)

Capecitabine: physician's choice of utilizing 1000 mg/m$^2$ BID 14 days on, 7 days off OR 1000 mg/m$^2$ BID 7 days on, 7 days off (capecitabine is rounded to the nearest 500 mg increment).

Vinorelbine: 25 mg/m$^2$ administered IV weekly (Day 1, 8, and 15 every 28 days).

5. Study Treatment Administration

A. Premedications

Optional pre-medications for nab paclitaxel should be administered prior to each dose of nab paclitaxel:

Diphenhydramine 25-50 mg IV (or equivalent).

Ranitidine 50 mg IV (or equivalent).

B. Treatment Plan

Patients starting chemotherapy at the time of study enrollment will receive 100 mg of anakinra administered SC daily during a 2-week run-in period (Days −14 to Day 0). Following the 2-week run-in, 100 mg of anakinra administered SC daily plus TPC of SOC nab paclitaxel, capecitabine, eribulin, or vinorelbine for a maximum of 6 months.

Patients enrolling in the study who are currently being treated with nab paclitaxel, capecitabine, eribulin, or vinorelbine will begin administration of anakinra on Day 1 of the next chemotherapy cycle.

End of Study will occur 6 months after the first dose of anakinra is administered, or at early withdrawal, whichever occurs first. After 6 months, patients may continue their SOC treatment alone until disease progression or intolerable toxicity. Anakinra dosing should be administered at approximately the same time of day every day. Patients will self-administer anakinra. The use of corticosteroids as an antiemetic is strongly discouraged to be able to evaluate anakinra's effects on patients' well being, energy level, and on plasma cytokines and other immunologic biomarkers.

One cycle of treatment will be determined by TPC drug product (either 21 or 28 days).

The treatment schema is shown in Table 46.

TABLE 46

Treatment schema

| Agent | Dose | Frequency of administration | Cycle length (days) | Route of administration |
|---|---|---|---|---|
| Anakinra | 100 mg | Daily for a maximum of 6 months | N/A | SC$^a$ |
| Nab paclitaxel | 100 mg/m$^2$ | Day 1, 8, 15 | 28 | IV |
| Eribulin | 1.4 mg/m$^2$ | Day 1 and 8 | 21 | IV |
| Capecitabine | $^b$1000 mg/m$^2$ | BID, Choice: 14 days on, 7 days off OR 7 days on, 7 days off | 21 | PO |
| Vinorelbine | 25 mg/m$^2$ | Day 1, 8, 15 | 28 | IV |

$^a$Anakinra should be administered at approximately the same time of day every day.
$^b$capecitabine dose is rounded to the nearest 500 mg increment.

The dose levels for TPC drug products will be modified at the physician's discretion.

6. Assessment

A. Anakinra Run-In Visit

Run-in visit (Day −14 Cycle 0) must begin within 7 working days after the patient's registration on the study. Only patients starting chemotherapy at the time of study enrollment will undergo the 2-week run-in treatment with anakinra. Patients enrolling in the study who are currently being treated with nab paclitaxel, capecitabine, eribulin, or vinorelbine will not undergo the anakinra run-in treatment.

The following will be issued:

1. Study coordinator will dispense anakinra (study drug) and instruct patients on its proper administration. Patient instruction from the anakinra package insert may also be distributed.
2. Whole blood collection (15 mls) for immunologic biomarkers prior to 1$^{st}$ dose of anakinra, and at the end of 14 days.
3. First administration of anakinra will be completed in the clinic.
4. Each patient will receive a diary and will be instructed how to fill in. Patient will also be instructed to return with the diary at the next visit.
5. Instruct patients to bring used and/or unused syringe dispensing pack for assessment of patient compliance.

B. Anakinra Plus TPC of MBC Agents

The following evaluations will be performed during therapy with anakinra and TPC of nab paclitaxel, eribulin, capecitabine, or vinorelbine (at the beginning of each cycle, unless otherwise specified):

1. A brief medical history, to capture events that have occurred since the last cycle. Events that were not captured in the baseline complete medical history should be recorded on the AE page of the CRF.
2. A brief physical examination, including vital signs and body weight.
3. Assessment of PS on the ECOG scale (Appendix III).
4. Assessment of concomitant medications Day 1 of each cycle.
5. A CBC with differential and platelet count prior to weekly dosing.
6. A CMP prior to weekly dosing for the first 2 cycles, Day 1 of cycles thereafter (cycle length is dependent on TPC drug product).
7. Tumor response by clinical assessment of the patient's disease (ie, by physical examination) must be performed every 4 weeks during therapy.
8. Radiological assessment of tumors (ie, chest X-ray, chest CT, brain CT or MRI, pelvic/abdominal CT or MRI, radionuclide bone scan) used to establish measurable or non-measurable disease (PET scan) will be performed every 8-9 weeks. The methods used for prestudy assessments (CT, MRI, or PET) should be used throughout the study. If possible, the same equipment should be used each time. Under RECIST criteria, PET cannot be used to assess measurable disease. Please see RECIST definition of measurable disease (Section 10.1.1).
9. Assessments of other sites of disease must be performed only to confirm a CR.
10. Whole blood collection (15 mls) for immunologic biomarkers, prior to treatment on Day −14 Cycle 0, after the 2-week run-in with anakinra (only for patients starting chemotherapy at the time of enrollment and undergoing the 2-week run-in treatment with anakinra), and monthly thereafter after initiation of anakinra/TPC. Patients who are currently being treated with nab paclitaxel, capecitabine, eribulin, or vinorelbine will only have one whole blood collection (15 mls) for immunologic biomarkers prior to the first administration of anakinra, and monthly thereafter after initiation of anakinra in combination with chemotherapy.
11. A toxicity assessment must be performed.
12. Patient diary assessment.

C. Early Withdrawal Assessments

This is a single assessment that will be performed when patient goes off treatment because of PD or toxicity that places patients off treatment, or in cases of physician decision or where patient withdraws consent. Patients who withdraw consent may not want any further assessment; however, they should be encouraged to have these final assessments done.

If patient withdraws for any reason during the treatment phase, patient should be asked to come to the clinic within 24-48 hours after the last treatment, particularly for the whole blood collection. Any delay within this window is not a deviation. The following evaluation will be performed at this visit:

1. A brief medical history should be done to capture events that have occurred since the last cycle. Events that were not captured in the baseline complete medical history should be recorded on the AE page of the CRF.
2. A brief physical examination, including vital signs and body weight.
3. Assessment of PS on the ECOG scale (Appendix III).
4. A CBC with differential and platelet count.
5. A CMP
6. A tumor clinical assessment of the patient's disease (ie, by physical examination).
7. Radiological assessment of tumors (ie, chest X-ray, chest CT, brain CT or MRI, pelvic/abdominal CT or MRI, radionuclide bone scan) used to establish measurable or non-measurable disease (PET scan). The methods used for prestudy assessments (CT, MRI, or PET) should be used throughout the study. If possible, the same equipment should be used each time. Under RECIST criteria, PET cannot be used to assess measurable disease.

8. A toxicity assessment.
9. Patient diary assessment.
10. Whole blood collection (15 mls) for immunologic biomarkers D. Follow Up Assessments Toxicities will be recorded for the first 30 days following the last dose of anakinra at a maximum of 6 months. Patients will be followed every 3 months for disease progression. Note: Patients who die or withdraw consent are considered off study and no further information will be collected.

7. Safety Evaluation—Adverse Events

All Grade 3 and 4 adverse events (AEs), Grades 1 and 2 alopecia, and all grades of neutropenia will be recorded in the CRF throughout the trial. In addition, all treatment-related Grade 1 and 2 laboratory abnormalities, which are deemed "clinically significant" by the Treating Physician will be documented in the CRF.

Adverse events (AEs) will be recorded throughout the trial. Toxicities and AEs will be graded using the Common Terminology Criteria for Adverse Events (CTCAE) Version 4.0. The events, and the relationship of each event to treatment, will be assessed by the Treating Physician and recorded on the CRF. Additional information about each event, such as treatment required, eventual outcome, and whether or not therapy had to be interrupted or dosages reduced, will also be recorded on the CRF. Adverse events will be recorded for up to 30 days following the last study treatment.

8. Efficacy Assessments

A. Definitions

Response and progression will be evaluated in this study using the international criteria published by the Response Evaluation Criteria in Solid Tumors (RECIST) Committee v 1.1 (Eisenhauer 2009). Best response will be determined based on the sequence of disease status with corresponding best response.

At baseline, tumor lesions/lymph nodes will be categorized measurable or nonmeasurable as follows:

i. Measurable Disease

Lesions that can be accurately measured in at least one dimension (longest diameter (LD) to be recorded) with a minimum size of:
  10 mm with spiral CT scan (irrespective of scanner type) and MRI (no less than double the slice thickness and a minimum of 10 mm)
  10 mm caliper measurement by clinical exam (when superficial)
  20 mm by chest X-ray (if clearly defined and surrounded by aerated lung)

ii. Nonmeasurable Disease

All other lesions (or sites of disease) are considered nonmeasurable disease. Lesions that are considered as truly nonmeasurable include the following:
  1. leptomeningeal disease
  2. ascites
  3. pleural/pericardial effusion
  4. inflammatory breast disease
  5. lymphangitis cutis/pulmonis
  6. abdominal masses that are not confirmed and followed by imaging techniques iii. Special Considerations Regarding Lesion Measurability Bone lesions, cystic lesions, and lesions with prior local treatment require special considerations.

1. Bone lesions
  Bone scans, PET scans, and plain films are not considered adequate imaging techniques to measure lesions. However, imaging techniques can be used to confirm presence or disappearance of bone lesions.
  Lytic bone with identifiable soft tissue components that can be evaluable by CT or MRI are considered measurable.
  Blastic lesions are nonmeasurable.
  To be assigned a status of PR or CR, changes in tumor measurements must be confirmed by repeat assessments performed at least 4 weeks after the criteria for response are first met. In the case of SD, follow-up measurements must have met the SD criteria at least once after study entry at a minimum interval of 8 weeks.
  A patient is considered to have progressed by bone scan if:
    a. The first bone scan with ≥2 new lesions compared to baseline is observed <12 weeks from randomization and is confirmed by a second bone scan taken ≥6 weeks later showing ≥2 additional new lesions (a total of ≥4 new lesions compared to baseline);
    b. The first bone scan with ≥2 new lesions compared to baseline is observed ≥12 weeks from randomization and the new lesions are verified on the next bone scan ≥6 weeks later (a total of ≥2 new lesions compared to baseline).

2. Cystic lesions
  Lesions that meet the criteria for radiographically defined simple cysts should not be considered malignant.
  Cystic metastases are measurable lesions, if they meet the criteria outlined in Section 10.1.1.

3. Lesions with prior local treatment
  Progression of a previously irradiated or locally treated area would be considered measurable.

B. Guidelines for Evaluation of Measurable Disease i. Measurement of Lesions

All measurements should be taken and recorded in metric notation using a ruler or calipers. All baseline evaluations will be performed as closely as possible to the beginning of treatment and never more than 4 weeks before the beginning of the treatment.

ii. Methods of Assessments

The same method of assessment and the same technique should be used to characterize each identified and reported lesion at baseline, during treatment and in follow-up. Imaging-based evaluation is preferred to evaluation by clinical examination when both methods have been used to assess the antitumor effect of treatment.

Clinical Lesions:

Clinical lesions will only be considered measurable when they are superficial and ≥10 mm diameter using calipers (for example, skin nodules). In the case of skin lesions, documentation by color photography (including a ruler to estimate the size of the lesion) is recommended.

Chest X-Rays:

Lesions on chest X-ray are acceptable as measurable lesions when they are clearly defined and surrounded by aerated lung. However, CT is preferable.

CT and MRI:

CT is the best available and reproducible method to measure lesions selected for response assessment. This guideline has defined measurability of lesions on CT scans based on the assumption is that the CT slice thickness is 5 mm or less. MRI is acceptable in certain situations such as body scans.

Ultrasound:

Ultrasound is not useful in assessment of lesion size and should not be used as a method of measurement.

Endoscopy, Laparoscopy:

The utilization of these techniques for objective tumor evaluation is not advised. However, they can be useful to confirm complete pathological response when biopsies are obtained or to determine relapse in trials where recurrence following complete response or surgical resection is an endpoint.

Tumor Markers:

Tumor markers alone cannot be used to assess response. If markers are initially above the upper normal limit, they must normalize for a patient to be considered in complete clinical response. Because tumor markers are disease specific, instructions for their measurement should be incorporated into protocols on a disease specific basis. Specific guidelines for CA125 response (in recurrent ovarian cancer) and PSA response (in recurrent prostate cancer) have been published The Gynecologic Cancer Intergroup has developed CA125 progression criteria which are integrated with objective tumor assessment for use in first-line trials in ovarian cancer.

Cytology, Histology:

These techniques can be used to differentiate between PR and CR in rare cases if required by protocol (for example, residual lesions in tumor types such as germ cell tumors, where known residual benign tumors can remain). When effusions are known to be a potential adverse effect of treatment (for example, with certain taxane compounds or angiogenesis inhibitors), the cytological confirmation of the neoplastic origin of any effusion that appears or worsens during treatment can be considered if the measurable tumor has met criteria for response or stable disease in order to differentiate between response (or stable disease) and progressive disease.

C. Tumor Response Evaluation i. Assessment of Overall Tumor Burden and Measurable Disease To assess objective response or future progression, it is necessary to estimate the overall tumor burden at baseline and use the baseline assessment for subsequent measurements. In studies where the primary endpoint is tumor progression, the protocol must specify if entry is restricted to those with measurable disease or whether patients having nonmeasurable disease are also eligible.

ii. Baseline Documentation of Target and Non-Target Lesions

When more than 1 measurable lesion is present at baseline all lesions up to a maximum of 5 lesions total (and a maximum of 2 lesions per organ, specifically, if 1 or 2 target organs are involved only 2 or 4 lesions, respectively, will be recorded).

a. Target Lesions

Target lesions should be selected on the basis of their size (lesions with the LD), representative of all target organs and their suitability for accurate repetitive measurements (either by imaging techniques or clinically).

A sum of the LD for all target lesions will be calculated and reported as the baseline sum longest diameter. The baseline sum of the LD will be used as reference to further characterize the objective tumor response of the measurable dimension of the disease.

Pathological lymph nodes are defined as measurable and meet criterion of a short axis of ≥15 mm by CT scan.

b. Non-Target Lesions

All other lesions (or sites of disease) should be identified as non-target lesions and should also be recorded at baseline. Measurements of these lesions are not required, and these lesions should be followed as "present" or "absent" or in rare cases "unequivocal progression".

Pathological nodes≥10 to <15 mm short axis should be considered non-target

D. Response Criteria i. Evaluation of Target Lesions

Complete Response (CR): Disappearance of all target lesions.

Partial Response (PR): At least a 30% decrease in the sum of the LD of target lesions taking as reference the baseline sum LD.

Progression (PD): At least a 20% increase in the sum of LD of target lesions taking as reference the smallest sum LD recorded since the treatment started or the appearance of 1 or more new lesions. In addition to the relative increase of 20%, the sum must also demonstrate the absolute increase of at least 5 mm. (the appearance of 1 or more lesion is also considered progression).

Stable Disease (SD): Neither sufficient shrinkage to qualify for PR nor sufficient increase to qualify for PD taking as reference the smallest sum LD since the treatment started.

ii. Special Notes on Assessment of Target Lesions

Lymph nodes should always have the actual short axis measurement recorded even if the nodes regress to below 10 mm on study. For PR<SD and PD, the actual short axis measurement of the nodes is to be included on the sum of target lesions.

Target lesions that become too small to measure: when lesions or lymph nodes become so faint on CT scan to measure comfortably, it is important that a value be recorded on the CRF. If the radiologist's opinion is that the lesion has disappeared, then 0 mm is reported. If a definable lymph node is present, but too small to measure, the default is 5 mm.

Lesions that split or coalesce on treatment: the LD of the fragmented pieces should be added together to calculate the lesion sum. If lesions coalesce, the vector of the LD in this new instance should be the maximal LD for the 'coalesced lesion'.

iii. Evaluation of Non-Target Lesions

Complete Response: Disappearance of all non-target lesions and normalization of tumor marker level(s) if applicable. All lymph nodes must be non-pathological in size (<10 mm short axis).

Non-CR/Non-PD: Persistence of 1 or more non-target lesions and/or maintenance of tumor marker level(s) above the normal limits.

Progressive Disease: Appearance of 1 or more new lesions or unequivocal progression of existing non-target lesions.

iv. Special Notes on Assessments of Progression of Non-Target Disease

When a patient also has measurable disease: to achieve 'unequivocal progression' on the basis of the non-target disease, there must be an overall level of substantial worsening in non-target disease such that, even in the presence of SD or PR in target disease, the overall tumor burden has increased sufficiently to merit discontinuation of therapy. The designation of overall progression based on non-target disease in the face of SD or PR is rare.

When a patient has only nonmeasurable disease: because worsening in non-target disease cannot be easily quantified, a useful test that can be applied when assessing patients for unequivocal progression is to consider if the increase in overall disease burden on the change in nonmeasurable disease is comparable in magnitude to the increase that would be required to declare PD for measurable disease, specifically, an increase in tumor burden representing an additional 73% increase in 'volume' (which is equivalent to a 20% increase in diameter in a measurable lesion).

v. New Lesions

The appearance of new malignant lesions denotes disease progression.

A lesion identified on a follow-up study (assessed during treatment or in the follow-up phase) in a location that was not scanned at baseline is considered a new lesion and will indicate disease progression.

If a new lesion is equivocal (ie, small size) follow-up assessments will clarify if it represents new disease. If repeat scans confirm a new lesion, then progression should be declared using the date of the initial scan.

FDG-PET imaging can complement CT imaging in assessment of 'new' lesions.

Negative FDG-PET at baseline, with a positive FDG-PET at a later assessment is a sign of PD based on a new lesion.

No FDG-PET at baseline and a positive FDG-PET at a later assessment
  If positive FDG-PET at a later assessment corresponds to a new site by CT, this is PD.
  If the positive FDG-PET at a later assessment is not confirmed by CT, additional follow-up CT scans are needed to determine if there is truly progression occurring (if so, the date of PD is date of initial abnormal FDG-PET scan)
  If a positive FDG-PET at a later assessment corresponds to a pre-existing site of disease on CT that is not progressing on the basis of the anatomic image, this is not PD.

E. Evaluation of Best Overall Response

The best overall response is the best response recorded from the start of the treatment until disease progression/recurrence (taking as reference for progressive disease the smallest measurements recorded since the treatment started), Table 47. The patient's best response assignment will depend on the findings of both target and non-target disease and will also take into consideration the appearance of new lesions. Furthermore, depending on the protocol and study requirements, it may also require both measurement and confirmation criteria.

TABLE 47

Evaluation of Best Overall Response

| Target Lesions | Non-target Lesions | New Lesions | Overall Response |
|---|---|---|---|
| CR | CR | No | CR |
| CR | Non-CR/non-PD | No | PR |
| CR | NE | No | PR |
| PR | Non-PD or NE | No | PR |
| SD | Non-PD or NE | No | SD |
| Not all evaluated | Non-PD | No | NE |

TABLE 47-continued

Evaluation of Best Overall Response

| Target Lesions | Non-target Lesions | New Lesions | Overall Response |
|---|---|---|---|
| PD | Any | Yes or No | PD |
| Any | PD | Yes or No | PD |
| Any | Any | Yes | PD |

CR = complete response,
PR = partial response,
SD = stable disease,
PD = progressive disease, and
NE = nonevaluable i. Timepoint Response Assessments of response are done at specified time points throughout the study for measurable disease (Table 47). When patients have nonmeasurable (non-target) disease only, Table 48 is used.

TABLE 48

Time Point Response: Patients with Non-target Disease Only

| Non-target lesions | New lesions | Overall response |
|---|---|---|
| CR | No | CR |
| Non-CB/non-PD | No | Non-CR/non-PD$^a$ |
| Not all evaluated | No | NE |
| Unequivocal PD | Yes or No | PD |
| Any | Yes | PD |

CR = complete response,
PD = progressive disease, and
NE = nonevaluable $^a$'Non-CR/non-PD' is preferred over 'stable disease' for non-target disease since SD is increasingly used as endpoint assessment for efficacy in some trials; to assign this category when no lesions can be measured is not advised ii. Missing Assessments and Nonevaluable (NE) Designation When no imaging/measurement is done at all at a specified time point, the patient is nonevaluable (NE) at that time point.

iii. Best Overall Response: All Time Points

The best overall response is determined once all data for the patient is known.

Best response determination in trials where confirmation of CR or PR is not required: Best response in these trials is defined as the best response across all time points (for example, a patient who has SD at $1^{st}$ assessment, PR at $2^{nd}$ assessment and PD on last assessment has a best overall response of PR). When SD is believed to be the best response, it must also meet the protocol specific minimum time from baseline.

Best Response determination in trials where confirmation of CR or PR is required: CR or PR may be claimed only if the criteria for each are met at a subsequent time point as specified in the protocol (generally 4 weeks later). In this circumstance, the best overall response can be interpreted as in Table 49.

TABLE 49

Best Overall Response When Confirmation of CR and PR is Required

| Overall response First time point | Overall response Subsequent time point | Best overall response |
|---|---|---|
| CR | CR | CR |
| CR | PR | SD, PD, or PR$^a$ |

TABLE 49-continued

Best Overall Response When Confirmation of CR and PR is Required

| Overall response First time point | Overall response Subsequent time point | Best overall response |
|---|---|---|
| CR | SD | SD provided minimum criteria for SD duration met, otherwise PD |
| CR | PD | SD provided minimum criteria for SD duration met, otherwise PD |
| CR | NE | SD provided minimum criteria for SD duration met, otherwise NE |
| PR | CR | PR |
| PR | PR | PR |
| PR | SD | SD |
| PR | PD | SD provided minimum criteria for SD duration met, otherwise PD |
| PR | NE | SD provided minimum criteria for SD duration met, otherwise NE |
| NE | NE | NE |

CR = complete response,
PR = partial response,
SD = stable disease,
PD = progressive disease,
NE = nonevaluable
[a]If a CR is truly met at first time point, then any disease seen at subsequent time point, even disease meeting PR criteria relative to baseline, makes the disease PD at that point (since disease must have reappeared after CR). Best response would depend on whether minimum duration for SD was met. However, sometimes 'CR' may be claimed when subsequent scans suggest small lesions were likely still present and in fact the patient had PR, not CR at the first time point. Under these circumstances, the original CR should be changed to PR and the best response is PR.

iv. Special Notes on Response Assessment

When nodal disease is included in the sum of target lesions and the nodes decrease to 'normal' size (<10 mm), they may still have a measurement reported on scans. This measurement should be recorded even though the nodes are normal in order not to overstate progression should it be based on increase in size of the nodes. As noted earlier, this means that patients with CR may not have a total sum of 'zero' on the CRF.

Where confirmation of response is required, missing assessments (NE) may complicate determination of best response. The analysis plan for the trial must address how missing data/assessments will be addressed in the determinations of response and progression. It may be reasonable to consider a patient with time point responses of PR-NE-PR as a confirmed response.

Patients with a global deterioration of health status requiring discontinuation of treatment without objective evidence of disease progression at that time should be classified as having "symptomatic deterioration". Every effort should be made to document the objective progression, even after discontinuation of treatment.

In some circumstances, it may be difficult to distinguish residual disease from normal tissue. When the evaluation of complete response depends on this determination, it is recommended that the residual lesion be investigated (fine needle aspirate/biopsy) before confirming the complete response status.

F. Evaluation of Pathologic Response

Pathologic response to therapy is the primary endpoint of the study protocol. Patients will undergo surgical resection after protocol-directed treatment. The pathologic specimen will be graded according to the tumor regression grading schema proposed by Rödel et al (Rödel 2005). In this categorization schedule, the response to treatment and the degree of tumor regression is categorized as follows:

TRG 0: no pathologic evidence of tumor regression
TRG 1: minor tumor regression with <25% of the pathologic specimen exhibiting fibrosis/necrosis.
TRG 2: moderate tumor regression with 25-50% of the pathologic specimen exhibiting fibrosis/necrosis.
TRG 3: significant tumor regression with >50% of the pathologic specimen exhibiting fibrosis/necrosis.
TRG 4: complete pathologic response to therapy; no histologic evidence of persistent malignancy.

A pathologic complete response (pCR) is defined as NO pathologic evidence of invasive disease at the primary site in the breast or axillary lymph nodes.

The presence or absence of a pCR will be assessed separately for the tumor and the lymph nodes. For patients who do not achieve a pCR, the size of the residual cancer in the tumor, on pathologic exam, will be documented in the as well as the number of positive lymph nodes.

G. PET Response

PET responses will be assessed by comparing initial and post-treatment scans. Scans will be graded as either complete response (CR), partial response (PR), stable disease (SD), or progressive disease (PD)(Young 1999). These are based on standardized uptake values (SUV), calculated as:

$$SUV = \frac{\text{Tissue concentration } (\mu Ci/gm)}{\text{Inj. Dose } (\mu Ci)/\text{body weight (gm)}}$$

CR=complete resolution of abnormal [$^{18}$F]flouoro-2-deoxy-D-glucose (FDG) uptake
PR=SUV decreases by at least 25% after 1 cycle of chemotherapy or by at least 25% after more than 1 cycle.
SD=SUV increases by less than 25% or decreases by less than 15%, and no visible increase in tumor size
PD=SUV increases by more than 25%, or visible increase in tumor size, or new lesions H. Frequency of Tumor Re-Evaluation Frequency of tumor re-evaluation while on treatment is protocol specific (see Section 8) and adapted to the type and schedule of treatment.

After the end of the treatment during the follow-up phase, the need for repetitive tumor evaluations depends on whether the trial has as a goal the response rate or the time to an event (progression/death). If 'time to an event' (for example, time to progression, disease-free survival, progression-free survival) is the main endpoint of the study, then routine scheduled re-evaluation of protocol specified sites of disease is warranted.

I. Confirmatory Measurement/Muration of Response i. Confirmation

In nonrandomized trials where response is the primary endpoint, confirmation of PR and CR is required to ensure responses identified are not the result of measurement error. In randomized trials (Phase II or III) or studies where SD or progression are the primary endpoints, confirmation of response is not required since it will not add value to the interpretation of trial results.

In the case of SD, measurements must have met the SD criteria at least once after study entry at a minimum interval, not less than 4 weeks.

ii. Time to Response

For patients who achieve a major objective response (CR or PR) the time to response will be assessed as the date of start of treatment to the date of response.

iii. Duration of Response

The duration of overall response is measured from the time measurement criteria are first met for CR/PR until the first date that recurrent or progressive disease is objectively documented (taking as reference for progressive disease the smallest measurements recorded on study).

iv. Duration of Complete Response

The duration of overall CR is measured from the time measurement criteria are first met for CR until the first date that recurrent disease is objectively documented.

v. Duration of Stable Disease

Stable disease is measured from the date of registration until the criteria for progression are met, taking as reference the smallest sum on study.

9. Statistical Methods

The secondary objectives of this protocol are to determine investigator-assessed objective response rate, clinical benefit rate, progression-free survival, and rates of chemotherapy or cancer-related anemia (HgB<10), and an anakinra-induced anti-IL-1 blood transcriptional signatures in patients who undergo IL-1 receptor blockade as therapy.

Objective response rate, clinical benefit rate, and progression-free survival will be determined with 95% confidence intervals. Whole blood transcriptional profiling will be performed to determine a gene expression signature that is induced by IL-1 receptor blockade by anakinra. The gene expression signatures from baseline will be compared to those signatures obtained after the 2-week run-in treatment with anakinra alone.

Descriptive statistics of demographic, clinical, technical, flow cytometry, and microarray derived variables will be given overall and by appropriate classifications (ie, time) for whole blood transcriptional profiling. Continuous variables will be described by their frequency of observations, mean, median, standard deviation, minimum, and maximum values. Categorical variables will be described by their frequency and percentage. Generalized linear mixed model analyses with appropriate distributional assumptions and link functions will be used to assess change in variables over time.

Unsupervised analyses for microarray data will include hierarchical cluster analysis and principal component analysis. Differential gene expression analysis will be conducted using linear mixed models with the Benjamini and Hochberg false discovery rate (FDR) of 5% used to account for multiple testing. Goodness of fit and checks of model assumptions will be carried out for all regression analyses. To ensure that data is not over-fit we will perform leave-one-out-cross-validation (LOOCV).

Example 5

Materials and Methods—Myeloid Cell-Derived IL-1B Promotes TSLP-TH2 Inflammation to Foster Breast Tumor Growth Cell Lines and Reagents.

Breast cancer cell lines (MDA-MB231, HS-578t, HCC-1806 and MCF-7) and benign counterpart cell line HS-Bst cells were obtained from ATCC and cultured in medium (RPMI supplemented with glutamine 2 mM, penicillin 50 U/ml, streptomycin 50 μg/ml, MEM non-essential amino acids 0.1 mM, HEPES buffer 10 mM, sodium pyruvate 0.1 mM and 10% of fetal calf serum). The following cytokines were obtained from R&D: IL-1β, IL-1α, IL-18, IL-6, Si16R, TNF-α, TSLP, and IL-4. GM-CSF (Leukine®) and anti-human CD14 antibody (RM052) were obtained from Immunex. Anakinra (Kineret®, Amgen Inc.) was purchased through Baylor University Medical Center pharmacy. PMA, ionomycin, and TAK1 inhibitor (5z-7-oxozeaenol) were obtained from Sigma-Aldrich (St. Louis, Mo.). TGF-βR kinase inhibitor was obtained from EMD Millipore (Billerica, Mass.). Caspase-1 activity detection kit was obtained from OncoImmunin Inc (Gaithersburg, Md.). The following antibodies were obtained from Invitrogen (Grand Island, N.Y.): anti-rabbit IgG conjugated to Alexa Fluor 568, anti-mouse IgG2b conjugated to Alexa Fluor 647, goat anti-mouse IgG2a conjugated to Alexa Fluor 568. Anti-human IL-1β (Ab9722), cytokeratin-19 (A53-B/A2), and TAK1 (phosphor T187) antibodies were obtained from Abcam (Cambridge, Mass.). The following antibodies were obtained from BD (Franklin Lakes, N.J.): antibodies to human CD3 (UCHT1), CD4 (SK3), CD8 (SK1), CD11c (B-ly6), CD19 (HIB19), CD56 (B159), IL-13 (JES10-5A2), IFN-γ (B27), PE-labeled OX40L (Ik-1), anti-CD11c antibody (S-HCL-3), anti-HLA-DR antibody (L-243). Anti-CD68 antibody (Y1/82A) was obtained from Biolegend (San Diego, Calif.). Anti-CD163 (EDHu-1) antibody was from AbD Serotec. Anti-IL-1β neutralizing (AB34_41.6E6.4A4) and non-neutralizing (AB34_41.1G12.1B11) antibodies, anti-TSLPR neutralizing antibody (AB81_85.1F11) were made in-house. Caspase-1 inhibitor (Z-WEHD-FMK), anti-TGF-β1 antibody (chicken IgY) and Anti-TGF-β neutralizing antibody (1D11) were purchased from R&D (Minneapolis, Minn.).

Cytokine Production and Analysis of Tumor Samples from Patients.

Tumor samples from patients diagnosed with breast carcinoma (in situ, invasive duct, and/or mucinous carcinoma of the breast, as well as lobular carcinoma) were obtained from the Baylor University Medical Center Tissue Bank (Institutional Review Board no. 005-145). The combined histological grading system including nuclear grade, tubule formation and mitotic rate, and staging system (according to tumor size, invasive or not, lymphoid node involvement, and spread out or not) were applied according to pathologists' report post-surgery. Whole-tissue fragments (4×4×4 mm, 0.02 g, approximately) were placed in culture medium with 50 ng/ml of PMA and 1 μg/ml of Ionomycin for 16 hours. TSLP, IL-1β, IL-1α, IL-33, IL-25, GM-CSF, and IL-13 levels were analyzed in the culture supernatant by Luminex (EMD Millipore, Billerica, Mass.). Concentrations of IL-18 and IL-1Ra from tissue cultured supernatants were determined by means of enzyme-linked immunosorbent assays (R&D system, Minneapolis, Minn.) following manufacture's protocols. Briefly, 96-well ELISA plate (Nunc, Roskilde, Denmark) was first coated with 10 g/ml of anti-human immunoglobulin capture antibody in 0.05 M sodium carbonate solution (pH=9.6) at 4-8 C for overnight. After washing with washing solution (50 mM Tris, 0.14 M NaCl, 0.05% Tween 20, pH=8.0), blocking solution (50 mM Tris, 0.14 M NaCl, 1% BSA, pH=8.0) was added to each well and the plate was incubated at room temperature for one hour. Then, samples and standards diluted with sample diluent (50 mM Tris, 0.14 M NaCl, 1% BSA, 0.05% Tween 20, pH=8.0) were added to each well and incubated for one hour at room temperature. After incubation, samples were removed and wells were washed five times with washing solution. Then, goat anti-human immunoglobulin antibody HRP conjugated was transferred into each well for one hour at room temperature. After incubation, HRP conjugate was removed and plate was washed five times with washing solution. Then, 100 l TMB substrate reagent (BD) was added into each well at room temperature in the dark. After five minutes of incubation, 100 l of 1 M H3PO4 was added subsequently to stop the reaction and the plate was read at 450 nm with the ELISA reader (Molecular Devices, Sunnyvale, Calif.). The standard curve was generated and the amount of total human immunoglobulin was further calculated.

Isolation of Monocytes and Culture of Monocyte-Derived DC and Macrophages.

CD14+ cells were positively selected from PBMCs of healthy donors using magnetic selection according to the manufacturer's instructions (Miltenyi Biotec). The purity was routinely >95%. Macrophages were generated from CD14+ monocytes by culturing with 100 ng/ml M-CSF (protocol see Martinez et al, 2006). MDDCs were generated from the adherent fraction of PBMCs by culturing with 100 ng/ml GM-CSF and 10 ng/ml IL-4 (R&D Systems).

Tumor Factor Preparation.

Cell lines were culture in medium (RPMI supplemented with glutamine 2 mM, penicillin 50 U/ml, streptomycin 50 µg/ml, MEM non-essential amino acids 0.1 mM, HEPES buffer 10 mM, sodium pyruvate 0.1 mM and 10% of fetal calf serum), and when the cells reached 90% of confluence fresh medium was added and left the cells in culture for additional 48 h. Cellular debris was removed by centrifugation and the supernatant was collected and stored at −80° C.

Isolation and Culture of Myeloid Dendritic Cells.

DCs were purified from buffy coat of blood from healthy donors. Briefly, DCs were enriched from mononuclear cells by negative selection using a mixture of antibodies against linage markers for CD3, CD9, CD14, CD16, CD19, CD34, CD56, CD66b and glycophorin A (EasySep, human pan-DC pre-enrichment kit). Cells from negative fraction were immuno-labeled with anti-human FITC-labeled linage cocktail (CD3, CD14, CD16, CD19, CD20 and CD56, BD biosciences); PE-labeled CD123 (mIgG1, clone 9F5, BD biosciences), APC-eflour780-labeled HLA-DR (mIgG2b, clone LN3, Sigma-Aldrich) and APC-labeled CD11c (mIgG2b, clone S-HCL-3, BD biosciences). DCs (lin−, CD123−, HLA-DR+, CD11c+) were sorted in a FACS Aria cytometer (BD Bioscience). DCs were seeded at $100 \times 10^3$ cells/well in 200 µl of medium (RPMI supplemented with glutamine 2 mM, penicillin 50 U/ml, streptomycin 50 µg/ml, MEM non-essential amino acids 0.1 mM, HEPES buffer 10 mM, sodium pyruvate 0.1 mM and 10% of human AB serum). DCs were cultured with medium alone or in the presence of 40% of cancer conditioned supernatant, or different reagents. After 18 h DCs were harvested and washed.

Co-Culture and Transwell Experiment.

Tumor cell lines were culture in medium (RPMI supplemented with 2 mM glutamine, 50 U/ml penicillin, 50 µg/ml streptomycin, 0.1 mM MEM nonessential amino acids, 10 mM Hepes buffer, 0.1 mM sodium pyruvate, and 10% fetal calf serum), and when the cells reached 90% of confluence fresh medium or different treatment (different doses of IL-1β, PMA/Ionomycin, 10 ng/ml IL-1α, 20 ng/ml IL-18, 10 ng/ml TNF-α, 20 ng/ml IL-6) were added and the cells were left in culture for an additional 24 h, 48 h, or 72 h. For tumor cells and mDCs coculture experiment, 100 k tumor cells were seeded in 24 well plate to grow overnight, then media was refreshed and 100 k mDCs were added to coculture for another 24-72 h. For the transwell experiment, 24-well-plate with inserts were used (Corning). 200K tumor cells were seeded in the plate to grow at least overnight, then 200 k mDCs were added into inserts. After 48 h of coculture, supernantants were harvested to determine IL-1β level by ELISA (Duoset, R&D System).

Tissue Immunofluorescence Staining.

6-µm-frozen sections from tissues were fixed with cold acetone for 5 min. The sections were labeled with 10 µg/ml of anti-IL-1β antibody (rabbit IgG, Abcam), followed by anti-rabbit IgG conjugated to AF568 (invitrogen); 5 ug/ml of anti-CD11c antibody (mouse IgG2b, BD), followed by anti-mouse IgG2b conjugated to AF647 (Invitrogen), or 10 ug/ml of anti-CD68 antibody (mouse IgG2b, Biolegend). Cytokeratin-19 was labeled with monoclonal antibody clone A53-BA2 (IgG2a; Abcam), followed by Alexa Fluor 568 goat anti-mouse IgG2a (Invitrogen). Finally, sections were counterstained for 2 min with 3 µM of the nuclear stain DAPI (in PBS; Invitrogen). To confirm specificity of IL-1β staining, primary anti-IL-1β antibody was preincubated with 100 µg of recombinant human IL-1β (R&D Systems) for 30 min at room temperature before staining of tissue sections that previously showed to be IL-1β positive.

Real-Time Polymerase Chain Reaction.

Samples were treated and lysed with Buffer RLT, and then stored at −80° C. until RNA extraction. Total RNA was isolated and purified from each sample by using RNeasy kit and RNase-free DNase (Qiagen) according to the manufacturer's instructions. cDNA was generated from total RNA with iScript™ cDNA Synthesis Kit. The resulting cDNA was then used for quantitative gene expression analysis on a Sequence Detection System 7,500 (Applied Biosystems). The primers used were as follows: human (h)TSLP, 5'-TAG-CAATCGGCCACATTGCC-3' (SEQ ID NO:41) and 5'-CTGAGTTTCCGAATAGCCTG-3 (SEQ ID NO:42), and human (h)IL-1β, 5'-TACCTGTCCTGCGTGTTGAA-3' (SEQ ID NO:43) and 5'-TCTTTGGG-TAATTTTGGGATCT-3' (SEQ ID NO:44), human (h) GAPDH, 5'-AGCCACATCGCTCAGACAC-3' (SEQ ID NO:45) and 5'-GCCCAATACGACCAAATCC-3' (SEQ ID NO:46), human (h) ABL1, 5'-TGACAGGGGACACCTA-CACA-3' (SEQ ID NO:47) and 5' ATACTCCAAATGC-CCAGACG-3' (SEQ ID NO:48), human (h) PGK1, 5'-CT-TCCTCCTTAAAACTCCTCTCC-3' (SEQ ID NO:49) and 5'-CTAAGGTCTCCAACGCTCTTCT-3' (SEQ ID NO:50), human (h) PES1, 5'-CATCACCCATCAGATTGTCG-3' (SEQ ID NO:51) and 5'-A GCTGCACCCCAGAGAAGTA-3' (SEQ ID NO:52). Equal amounts of cDNA were used with the iTaq SYBR Green Supermix with ROX (Bio-Rad) and primer mix according to the real-time PCR protocols supplied by the manufacturer. Amplification efficiencies were validated against the housekeeping gene, GAPDH, PES1, and ABL1. The data were normalized to GAPDH mRNA level. The relative quantification of target gene expression was done by the comparative cycle threshold (CT) method. The formula 2-ΔΔCT was used for each run according to the manufacturer's instructions and published methods for this system.

Tumor-Bearing Mice and In Vivo Experiment.

NOD/SCID/$\beta_2$ m$^{-/-}$ mice (Jackson ImmunoResearch Laboratories) were sublethally irradiated (12 cGy/g body weight of 137Cs γ irradiation) the day before tumor implantation. Then 10 million Hs-578t breast cancer cells harvested from cultures were injected subcutaneously into the flanks. Mice were then reconstituted with 1 million monocyte-derived DCs (MDDCs) and autologous T cells. CD4+ and CD8+ T cells were positively selected from thawed PBMCs using magnetic selection according to the manufacturer's instructions (Miltenyi Biotec). The purity was routinely >90%. 10 million CD4+ T cells and 10 million CD8+ T cells were transferred at days 3, 6, and 9 after tumor implantation. MDDCs were generated from the adherent fraction of PBMCs by culturing with 100 ng/ml GM-CSF and 10 ng/ml IL-4 (R&D Systems). Anakinra (2 mg/kg body weight) or PBS were injected daily in peritumor area since day 3 after tumor engraftment. 200 ug TSLPR blocking antibody was given on day 3,6,9. In some experiments, TGF-13 blocking antibody was given on day 3,6,9. Tumor size was monitored every 2-3 d. Tumor volume (ellipsoid) was calculated as follows: ([short diameter]$^2$×long diameter)/2. On day 16, the tumors were harvested. In some experiments, only one time DCs and total T cells transfer was done. Cell suspension was obtained from breast cancer tissue of above mice. Cell suspensions were obtained by digestion with 2.5 mg/ml of collagenase D (Roche Diagnostics, Indianapolis, Ind.), and 200 U/ml of DNAse I (Sigma-Aldrich, St. Louis, Mo.) for 30 minutes at 37° C. Washed three times and analyzed with FACS-CantoII (Becton Dickinson).

Flow Cytometry Analysis.

The anti-human antibodies used were FITC-labeled lineage cocktail (CD3, CD14, CD16, CD19, CD20 and CD56, BD Biosciences); PE-labeled OX40L (mIgG1, clone Ik-1, BD biosciences); PE-labeled TSLPR; APC-labeled HLA-DR (mIgG2a, clone L243, BD); APC-labeled CD11c (mIgG2b, clone S-HCL-3, BD Biosciences); Pacific Orange-Labeled CD45. TGF-β1 (chiken IgY, R&D), TGF-βRI, TGF-βRII, TGF-βRIII (goat IgG, R&D); FITC-labeled IL-1β (R&D); PE-labeled IL-13 (rat IgG1, clone JES10-5A2 BD biosciences); PECy7-labeled TNF-α (mIgG1, clone mAb11, BD biosciences); Alexa Flour-700 labeled IFN-γ (mIgG1, clone B27, BD biosciences). For surface staining, cells were incubated with the antibodies for 30 minutes at 4° C. in the dark, then washed three times and fixed with 1% paraformaldehyde to be analyzed in a FACS Canto (Becton Dickinson). For intracellular cytokines, cells were stained using BD cytofix/cytoperm fixation/permeabilization kit according to the manufacturer directions. For caspase-1 staining, cells were incubated with substrates (CaspaLux-E1D2, OncoImmunin, Inc.) for 50 minutes at 37° C. and washed with washing buffer 2 times, then stained for surface markers for 10 minutes at room temperature.

Statistical Analysis.

All statistics and graphs were done with Prism software (GraphPad, La Jolla, Calif.). Differences in variables between any 2 groups were analyzed using the Mann-whitney test or two-tailed t-test. Differences between any 3 or more groups were analyzed by analysis of variance (ANOVA).

Example 6

Results: Myeloid Cell-Derived IL-1B Promotes TSLP-TH2 Inflammation to Foster Breast Tumor Growth Human breast cancer tumor microenvironment displays features of TSLP-driven Th2 inflammation that promote tumor development. The inventors have discovered the underlying molecular mechanisms by which TSLP is regulated. The results set forth in this Example show that IL-1β induces TSLP production from breast cancer cells lines in a dose dependent manner in vitro. Cancer cells induce both transcription and secretion of IL-1β in myeloid dendritic cells (mDCs) and monocytes. This is mediated by cancer cell-derived TGF-β. Moreover, TAK1 signaling is involved in caspase 1 activation and TGF-β-dependent IL-1β production. Administration of anti-TGF-β neutralizing antibody or IL-1R antagonist Anakinra prevents tumor growth in vivo and blocks iTh2 generation in vivo. Moreover, significantly higher levels of IL-1β are present in cancer tissue than surrounding tissue. The level of IL-1β correlates positively with the level of IL-13 in tumor tissue of patients. Importantly, IL-1β level is associated with the stage of the disease. Thus blockade of IL-1β represents a novel approach to breast cancer immunotherapy.

IL-1β Induces TSLP Production from Breast Cancer Cells.

Figures 4A, 4B:
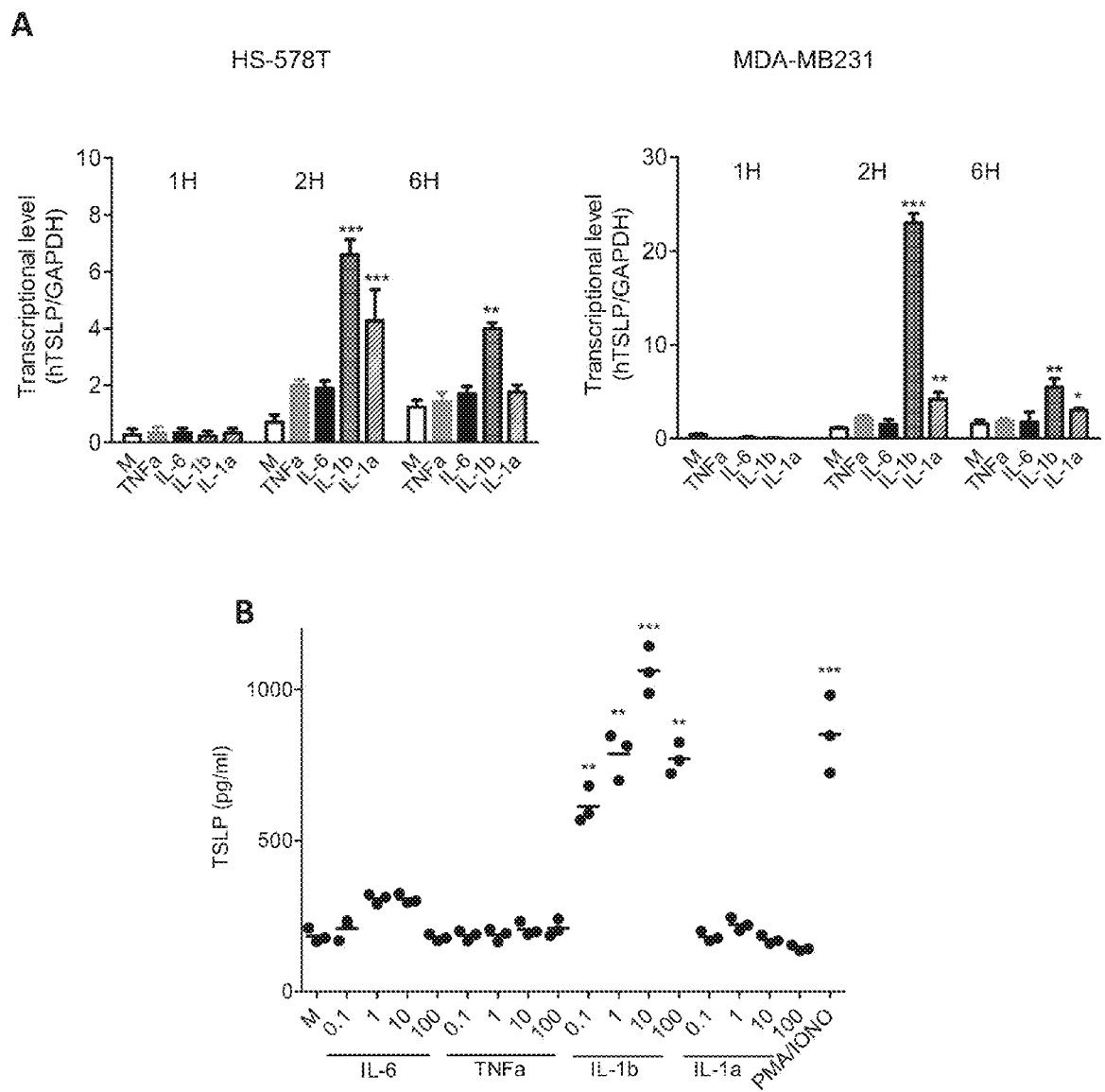
FIG. 4A-4E. A) HS-578t or MDA-MB231 cells were treated with medium alone, 10 ng/ml of IL-1β, IL-1α, TNF-α, or IL-6 for the indicated time course individually. Cells were harvested and measured for TSLP mRNA level by quantitative real-time PCR. Values were normalized to internal control GAPDH. Bars show the mean±SEM for triplicate wells from a representative experiment. *p<0.0001, p<0.01, *p<0.05. B) Luminex analysis of TSLP in supernatants of MDA-MB231 cells as indicated after 48 h of culture in media (M) alone, or in the presence of different doses of IL-6 plus sIL6r, TNF-α, IL-1b, or IL-1α, or PMA and ionomycin. Values are plotted as mean±SEM from triplicate experiments. C) Luminex analysis of TSLP in supernatants of MDA-MB231 cells after different time points of culture with M alone, or in presence of 10 ng/ml IL-1β, or IL-1β together with anti-IL-1β neutralizing or non-neutralizing antibody. Values are plotted as mean±SEM from triplicates. D) MDA-MB231 cells were cultured in chamber well in presence of different dose of IL-1β as indicated, or M alone for 24 hours. Cells were fixed in situ, and TSLP was stained with anti-TSLP antibody. Nuclear was counter-stained with DAPI. Bar: 60 um. See also FIG. 9. E) levels of TSLP and IL-1β were determined by luminex in supernatants of breast tumor fragments post PMA/ionomycin stimulation. Levels of TSLP were plotted in contrast to IL-1β from the same patient. Analysis used nonparametric spearman correlation to determine the level of correlation between two cytokines.
Figure 4C:
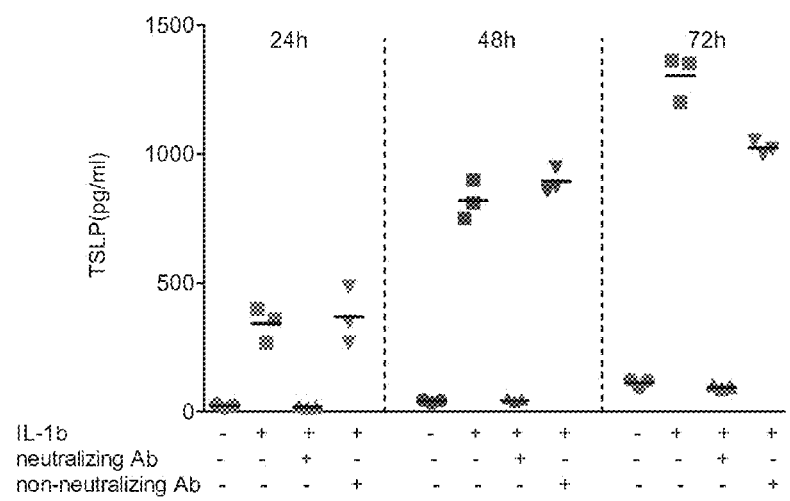
Figures 9A, 9B, 9C:
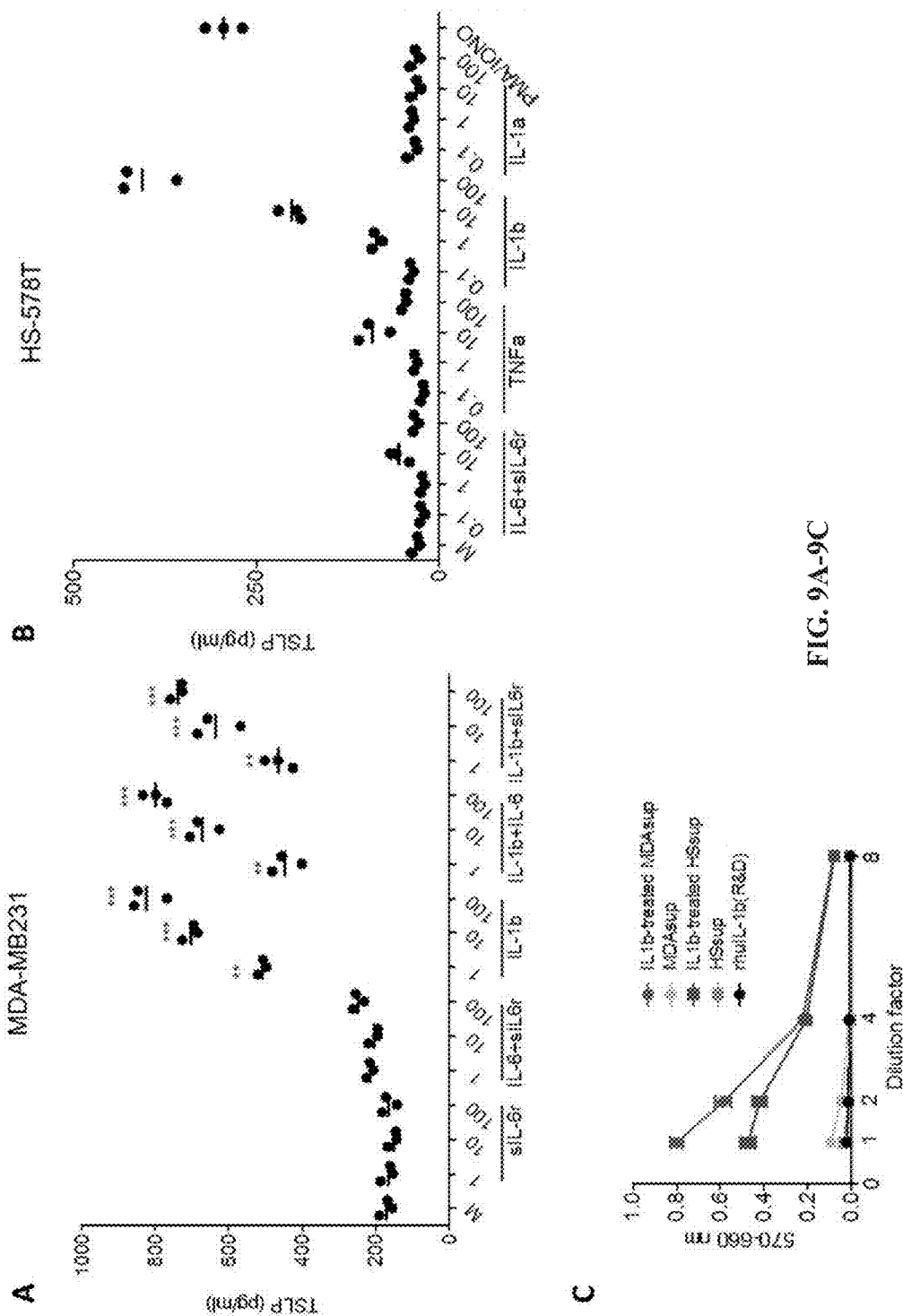
FIG. 9A-9C. A-B) Luminex analysis of TSLP in supernatants of breast cancer cell lines as indicated after 48 h of culture in media (M) alone, or in the presence of different doses of cytokines. Values are plotted as mean±SEM from triplicate experiments. A) MDA-MB231 cells were cultured, while in B) HS-578T cells were cultured for TSLP induction experiment. C) TSLPR+/IL-7Rα+ Baf3 cells were seeded in 96-well plate. Serial dilution was done to IL-1β-treated MDA-MB231 culture sups, IL-1β-treated HS-578t culture sups, tumor sups without IL-1β treatment, or IL-1β. The conditioned sups with different dilution were used to treat Baf3 cells. The proliferative values were measured based on MTT assay.

Different pro-inflammatory cytokines have the potential to induce TSLP from keratinocytes, both transcriptionally and translationally. Whether IL-1β could induce TSLP production from breast cancer cells was tested. Breast cancer cell lines HS-578t or MDA-MB231 cells in culture were treated with medium alone, IL-1β, IL-1α, IL-6 or TNF-α for the indicated time course. Cells were harvested and TSLP mRNA levels were measured by quantitative real-time PCR (FIG. 4A). As early as 2 hours, IL-1β and IL-1α could induce significant TSLP transcription in both cells lines tested (FIG. 4A, *P<0.0001, P<0.01). MDA-MB231 cells were cultured in media alone, or treated with different cytokines (IL-6 and soluble IL-6r, TNF-α, IL-1β or IL-1α at different doses as indicated), or PMA and ionomycin for 48 hours (FIG. 4B, FIG. 9A). TSLP levels in the culture supernatants were determined by Luminex. IL-1β could induce TSLP production in a dose-dependent manner. 10 ng/ml of IL-1β gave rise to significantly highest level of TSLP production compared to TNF-α, IL-6 and or soluble IL-6r, or IL-1α (P=0.0001; FIG. 4B and FIG. 9A). IL-1β shows similar effect on another breast cancer cell line HS-578t (FIG. 9B). To determine whether IL-1β was responsible for specific TSLP production from cancer cells, MDA-MB231 cells were cultured with IL-1β in the presence of anti-IL-1β neutralizing antibody, or non-neutralizing antibody for 24-72 hours. The pre-treatment of IL-1β with neutralizing antibody was able to abolish the ability of IL-1β to induce TSLP from cancer cells at different time point (P=0.001, FIG. 4C).

Figure 4D:
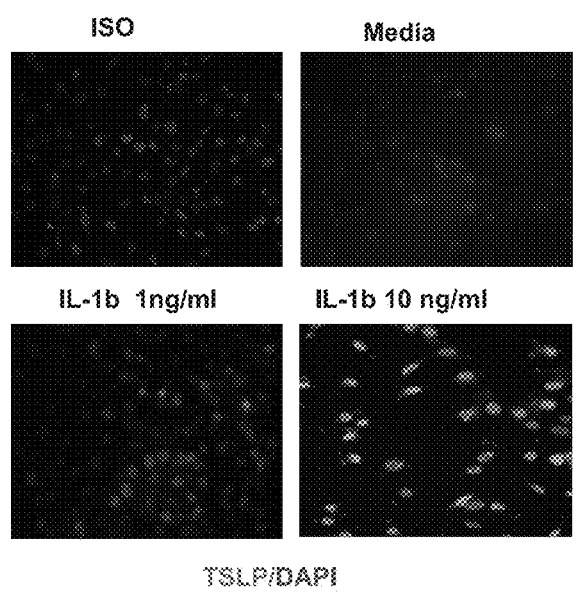

To investigate whether the TSLP induction effect is due to IL-1β enhanced-TSLP generation in single cells, or possibly caused by IL-1β's direct effect on cancer cell proliferation if any, MDA-MB231 cells were cultured in chamber wells in presence or absence of different doses of IL-1β (as indicated) for 24 hours, the last 5 hours Golgi-plug and Golgi-stop was added to the cell culture in order to allow TSLP accumulation intracellularly. 10 ng/ml of IL-1β induces more accumulation of TSLP compared with a lower dose of IL-1β treatment. Both doses (1 ng/ml and 10 ng/ml) are able to significantly induce TSLP production from single cell level, compared to in absence of IL-1β (FIG. 4D). Furthermore, when the TSLP-dependent Baf3 cell (TSLPR$^+$/IL-7Rα$^+$) line cells in presence or absence of IL-1β-treated breast cancer cells culture supernatants. The Baf3 cells do not proliferate in presence of IL-1β alone, and show very limited proliferation upon unstimulated-cancer cell culture sups treatment, while IL-1β stimulated MDA-MB231 cells culture sups or HS-578t cells culture sups enhance the proliferation of the Baf3 cells in a dose-dependent manner (FIG. 9C), demonstrating IL-1β-induced TSLP is bioactive.

High IL-1β Level in Tumor Clinically Correlates with TSLP Level in Patients.

Figure 4E:
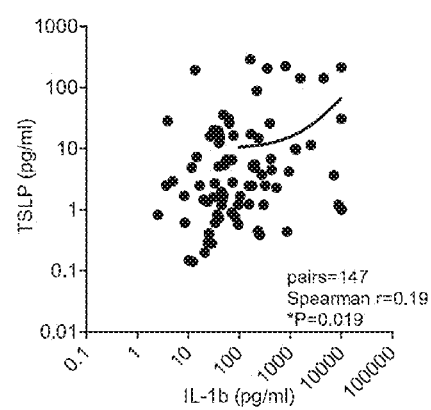

TSLP and IL-1β were screened by Luminex in supernatants of human breast tumor fragments (T) from patient, stimulated for 16 hours with PMA and ionomycin. In line with the findings that IL-1β induced TSLP production from in vitro breast cancer cell lines culture, the level of IL-1β in patients tissue is correlated with the level of TSLP in a subset of patients (FIG. 4E; pairs=147, P=0.019 with spearman r=0.19).

Figures 10A, 10B, 10C:
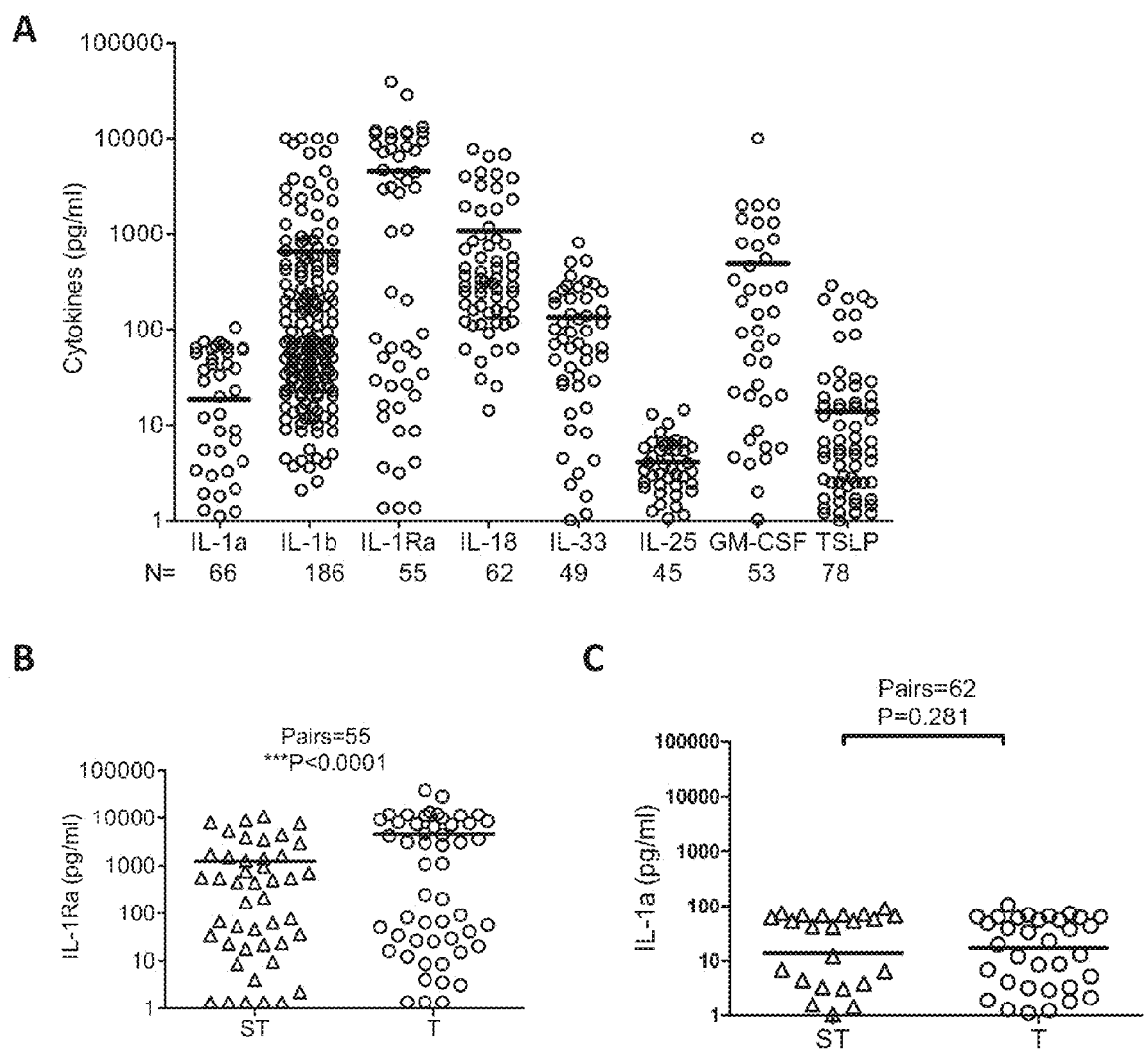
FIG. 10A-10C. A) levels of IL-18, IL-25, IL-33, GM-CSF, TSLP is determined by luminex or ELISA in supernatants of breast tumor fragments post PMA/ionomycin stimulation; B) level of IL-1Rα is determined by luminex in supernatants of breast tumor fragments (T) or macroscopic uninvolved surrounding tissue (ST) post PMA/ionomycin stimulation; C) level of IL-1α is determined by luminex in supernatants of breast tumor fragments (T) or macroscopic uninvolved surrounding tissue (ST) post PMA/ionomycin stimulation.

To determine the expression pattern of IL-1β in breast cancer tissue of patients, IL-1β and other innate cytokines were also compared between tumor tissue (T) and surrounding tissue (ST) from the same patient, stimulated for 16 hours with PMA and ionomycin. Tumor tissue express high amount of IL-1 family cytokines (FIG. 10A). In 138 patients, the tumor tissue displayed significantly higher level of IL-1β than that of matched macroscopically uninvolved surrounding tissue (FIG. 5A; ST: mean±SEM=218.9±75.76 pg/ml; T: mean±SEM=527±127.8 pg/ml. P<0.0001, n=138). Accordingly, tumor tissue displayed higher levels of IL-1Ra (FIG. 10B; ST: mean±SEM=1257±332.2 pg/ml; T: mean±SEM=4489.6±979 pg/ml. P<0.0001, n=55). No difference of IL-1a level exists between surrounding tissue and tumor tissue (FIG. 10C; ST: mean±SEM=12.3±3.3 pg/ml; T: mean±SEM=17.2±3.4 pg/ml. P=0.281, n=62).

Infiltrating Myeloid Cells Express IL-1β in Patients, Both in Primary Tumor Tissue and Lymph Node Metastasis.

Figures 5A, 5B:
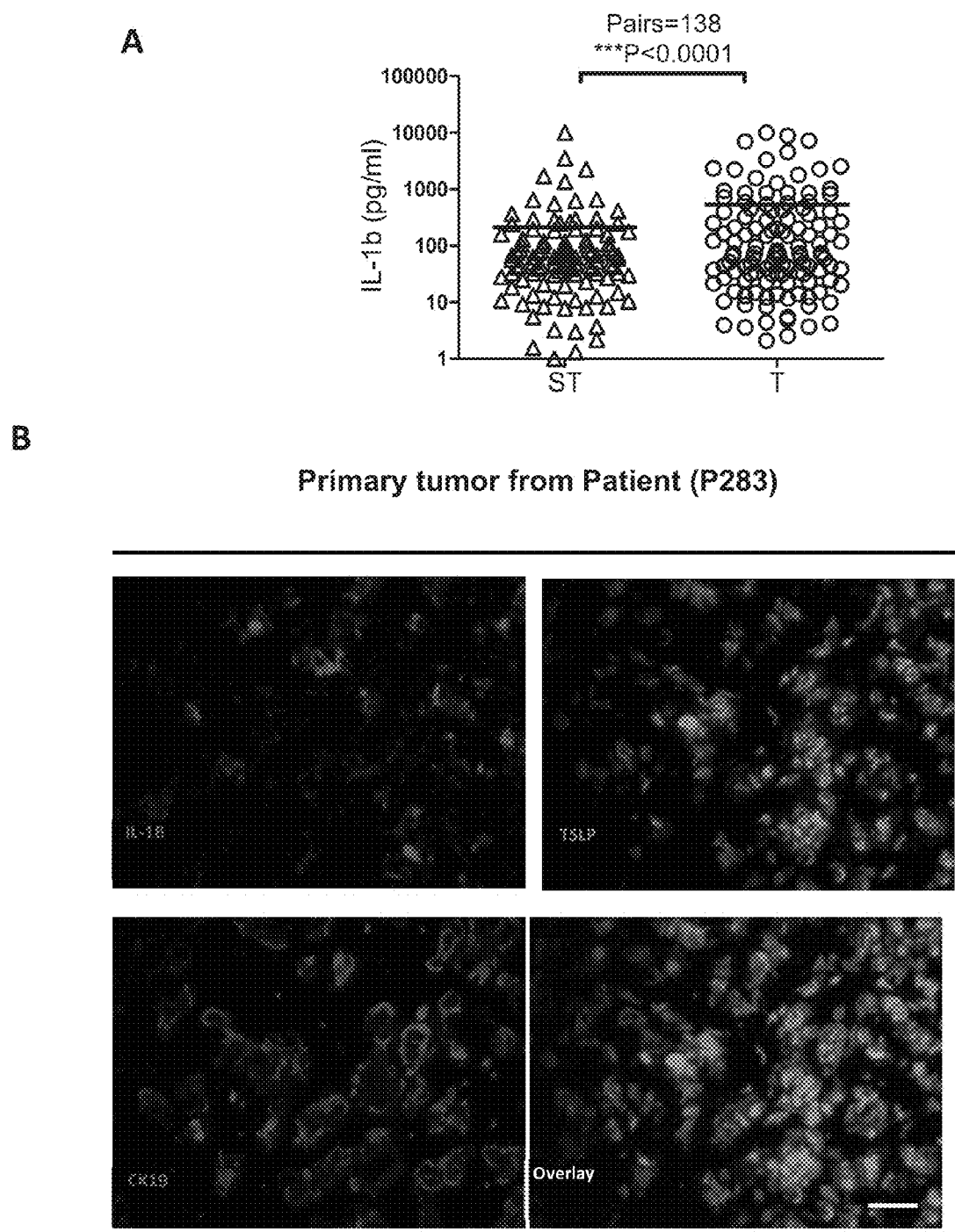

Cancer cells can directly express IL-1β transcripts or induce cells within the tumor microenvironment to do so (Portier et al, 1993). Studies have documented constitutive IL-1β protein production in human and animal cancer cell lines including sarcomas and ovarian and transitional cell carcinomas (Dinarello, 1996). To identify the cells producing IL-1β in human breast cancer tissue, frozen tissue sections from surgically removed primary tumors or axillary lymph node metastasis of breast cancer patients were analyzed by immunofluorescence. All 20 primary tumors screened were positive for tissue IL-1β staining, and IL-1β was present in infiltrating cells rather than in tumor cells visualized by expression of TSLP and cytokeratin-19 (FIG. 5B shows one representative staining pattern). To further characterize the infiltrating cellular types which co-express IL-1β, frozen sections were stained with different combinations of myeloid cells markers and anti-IL-1β antibody. IL-1β expressing cells were mainly HLA-DR$^{hi}$, CD11c$^+$, and CD14$^+$ cells. These cells could be dendritic cells (DCs) and tissue monocytes. IL-1β was also detected in some CD163$^+$, and CD68$^+$ cells (FIG. 5C). Metastatic tumor from surgically removed axillary lymph node tissue was stained for cytokeratin-19, TSLP, IL-1β and CD11c. Myeloid cells express IL-1β, although metastatic tissue shows less IL-1β$^+$ infiltrates in contrast to primary tumor tissue.

Cancer Surface Factor(s) Induce IL-1β Production in mDCs.

Figures 6A, 6B, 6C:
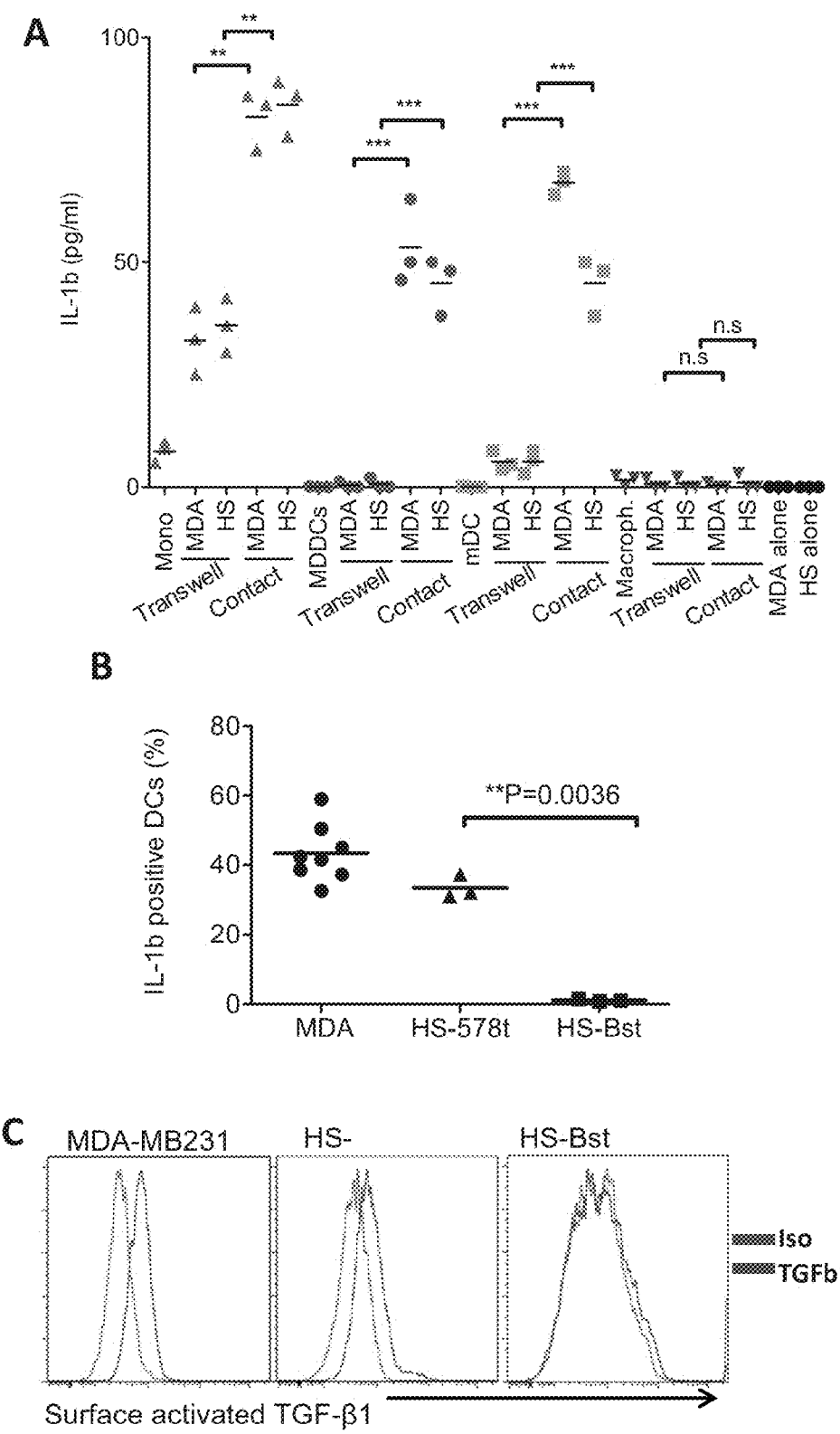
FIG. 6A-6F. A) Cancer cells (MDA-MB231 or HS-578t), co-cultured with blood monocytes, monocyte-derived DCs, mDCs or monocyte-derived macrophages in regular wells or transwell to separate two types of cells in culture for 48 hours. Supernatants were harvested to determine IL-1β level by Luminex. Values are plotted as mean±SEM from triplicate experiments. B) mDCs were co-cultured with MDA-MB231 cells, HS-578t cells or HS-Bst cells for 16 hours. Intracellular IL-1β level was measured by FACS. Gated on viable myeloid cells. The percentages of IL-1β positive DCs were plotted. Each dot represents one experiment. C) Surface activated form of TGF-β1 was stained using anti-TGF-β1 antibody and acquired by FACS. The left curve in the MDA-MB231 and HS-panels is the Iso signal, and the right curve is the TGF-β1 signal. D) MDA-MB231 cells were co-cultured with mDCs for 48 hours, in presence of different dose of TGF-βR kinase inhibitor or anti-TGF-β neutralizing antibody, DMSO, or isotype control respectively. IL-1β level in the sups was detected by Luminex. Values are plotted as mean±SEM. E) MDA-MB231 cells and mDCs were co-cultured for 16 hours, in presence or absence of TGF-βR kinase inhibitor and or anti-TGF-β neutralizing antibody. Intracellular staining with anti-IL-1β antibody was done and acquired by FACS. Gated on viable mDCs. The percentages of IL-1β positive CD11c cells were plotted. Dot represents each experiment. F) MDA-MB231 cells and mDCs were co-cultured in presence or absence of TGF-βR kinase inhibitor and or anti-TGF-β neutralizing antibody for different time periods as indicated. Cells were harvested and IL-1β mRNA level was detected using quantative RT-PCR. Values were normalized to GAPDH. Bars show the mean±SEM for triplicate wells from a representative experiment. \*\*\*p<0.0001, \*\*p<0.01, \*p<0.05. n.s means no significance. See also FIG. 12.
Figures 11A, 11B:
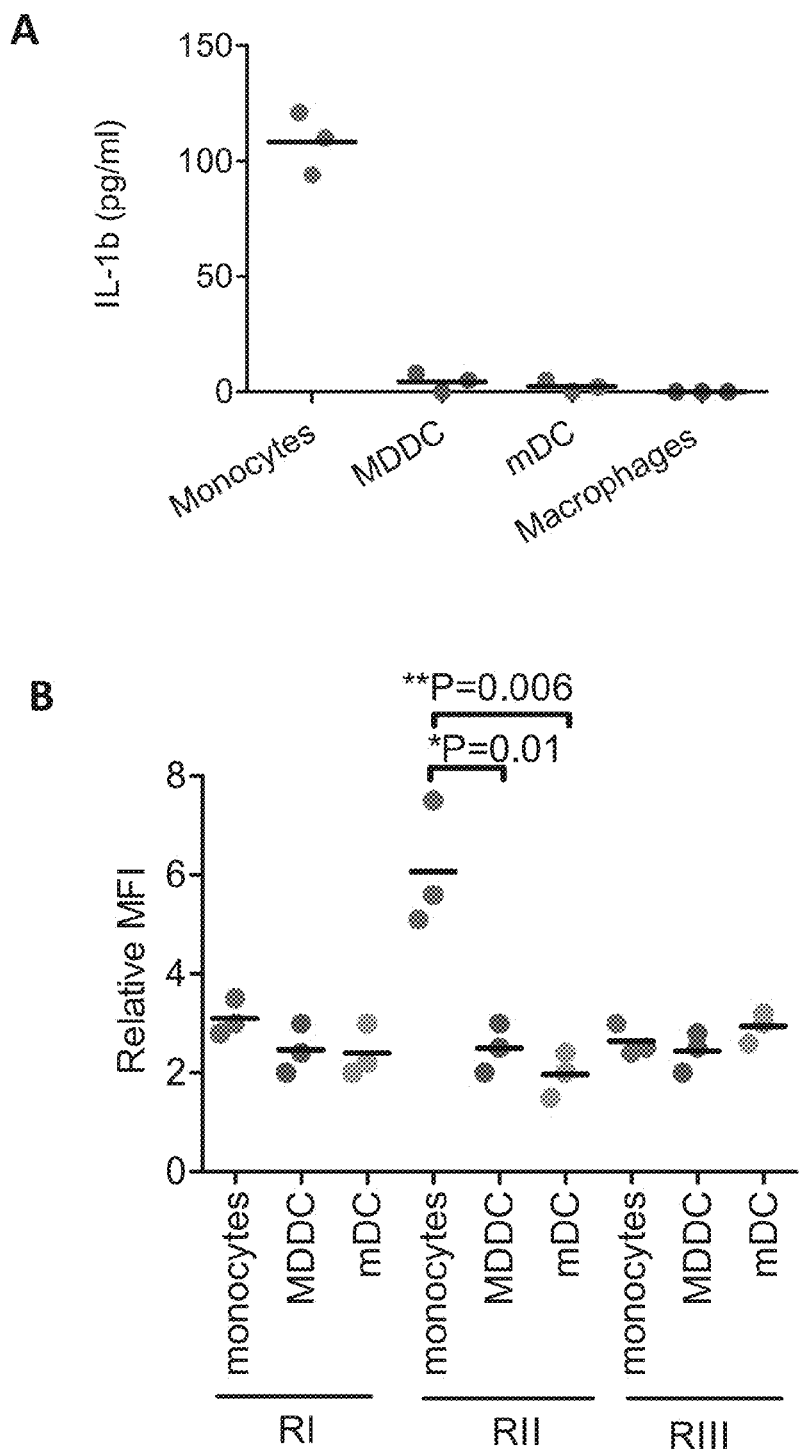
FIG. 11A-11B. A) MDA-MB231 cells culture sups were used to treat different myeloid cells (monocytes, monocyte-derived dendritic cells, mDCs, and monocyte-derived macrophages) as indicated for 48 hours. Supernatant were harvested to determine IL-1β level by Luminex. Values are plotted as mean±SEM from triplicate experiments. B) Surface expression of TGF-βRI, II, and III were detected on monocytes, MDDC, and mDCs, respectively by FACS. Y-axis indicates the expression level.

The inventors observed that IL-1β$^+$ infiltrating myeloid cells are always localized near TSLP-expressing tumor cells. Therefore, whether cancer derived factors are able to induce IL-1β production from myeloid cells was tested. To do so, blood monocytes, mDCs, monocyte-derived dendritic cells (MDDC), and monocyte-derived macrophages were stimulated for 48 hours by cancer cell-culture sups, which is known being able to drive Th2 polarization through activation of mDCs in vitro (Pedroza et al., 2012). The cancer cell-culture supernatants could induce IL-1β from monocytes, but not from MDDC, mDC, or macrophages (FIG. 11A). Next, the transwell system was used to investigate whether the in vitro modulation of IL-1β production by myeloid cells would rely on direct contact of surface molecules between cancer cells and myeloid cells. So monocytes, MDDCs, monocyte-derived macrophages and blood mDCs were co-cultured with MDA-MB231 or HS-578t cells, which were separated by the transwell membrane with a 0.3 μm pore diameter. Cancer cells or myeloid cells alone do not produce detectable IL-1β after 48 hours of culture. Co-culture with cancer cells in direct contact manner significantly enhanced IL-1β production in the supernatant of the well where monocytes, MDDC, and mDCs were present, but not macrophages (FIG. 6A). Co-culture with cancer cells in transwells significantly enhanced the IL-1β production by monocytes, MDDC and mDCs, whereas IL-1β production from macrophages remained unaffected (FIG. 6A). These experiments show that for MDDC and mDCs, the modulation of IL-1β production is totally contact dependent, whereas for monocytes the modulation is partially contact-dependent, and could be induced by a soluble factor derived from cancer cells.

Cancer Surface Bound TGF-β is Involved in IL-1β Production During Cancer Cells Co-Culture with mDCs.

Figure 13:
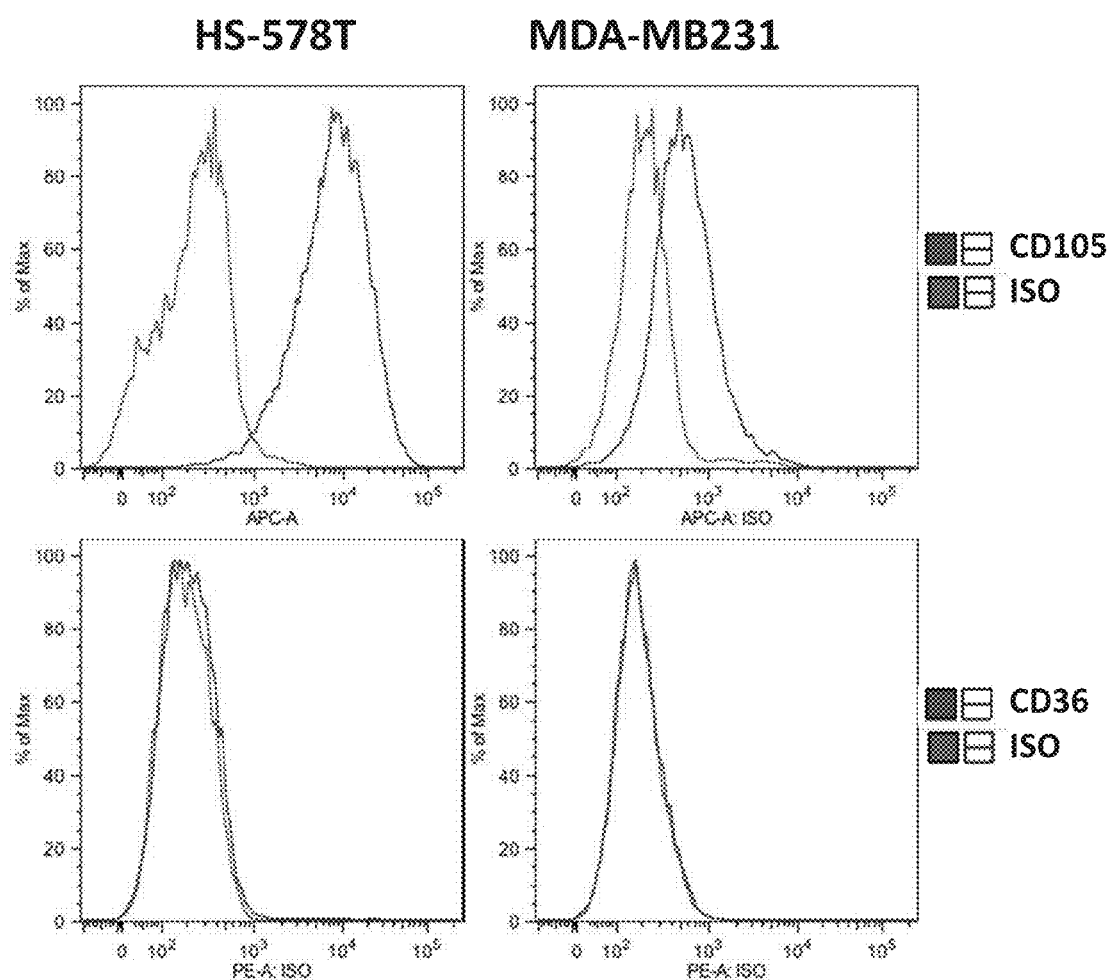
FIG. 13. Cancer cells express CD105 but not CD36 on their surface. Breast cancer cells in culture were harvested and surface expression level of CD105 and CD36 were detected by FACS analysis. anti-CD105, anti-CD36, or matched isotype control antibodies were used. Histogram shows relative expression in contrast to isotype staining. The curves on the left in the top panels is the isotype signal.

It is well known that TGF-β expression increases markedly in human cancers, including breast cancer. TGF-β-related-signal transduction/gene activation has been implicated in the oncogenesis of many human cancers. TGF-β has the potential to induce IL-1β mRNA in human monocytes (Allen et al., 1990). In various disease models where IL-1β plays a pathogenic role, TGF-β is also over-expressed and involved (Lee et al., 2012; Hideaki et al., 2008). Another very important characteristic of TGF-β is its abundant surface expression pattern and restrictive transformation from latent form to active form to allow function (Gleizes et al., 1997). To investigate whether cancer cell-derived TGF-β contributes to IL-1β production in mDCs during contact, mDCs were cultured together with breast cancer cells (MDA-MB231 and HS-578t) or benign counterpart cells (HS-Bst, derived from the same patients as HS-578t cells). In presence of the benign HS-Bst cells, IL-1β was barely induced from mDCs (FIG. 6B); while in presence of HS-578t cells or MDA-MB231 cells, IL-1β was induced in mDCs. We then examined the cancer cells surface expression for the activated from of TGF-β. Both MDA-MB231 cells and HS-578t cells express active TGF-β, whereas HS-Bst cells did not express activated TGF-β (FIG. 6C). Furthermore, cancer cells express CD105 but not CD36 on their surface, indicating the possibility of surface activation of TGF-β (FIG. 13).

Figures 6D, 6E, 6F:
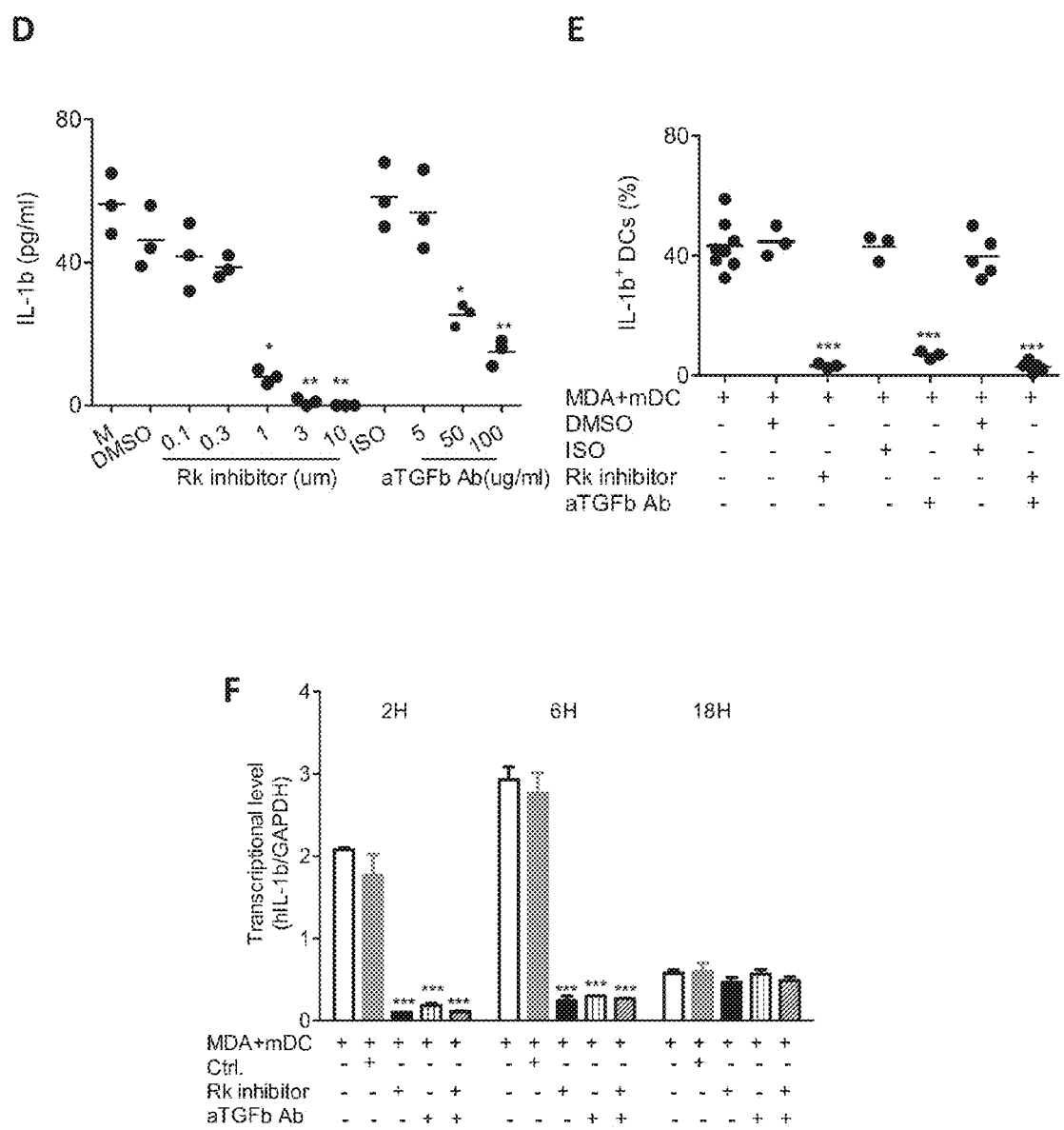
Figures 12A, 12B, 12C:
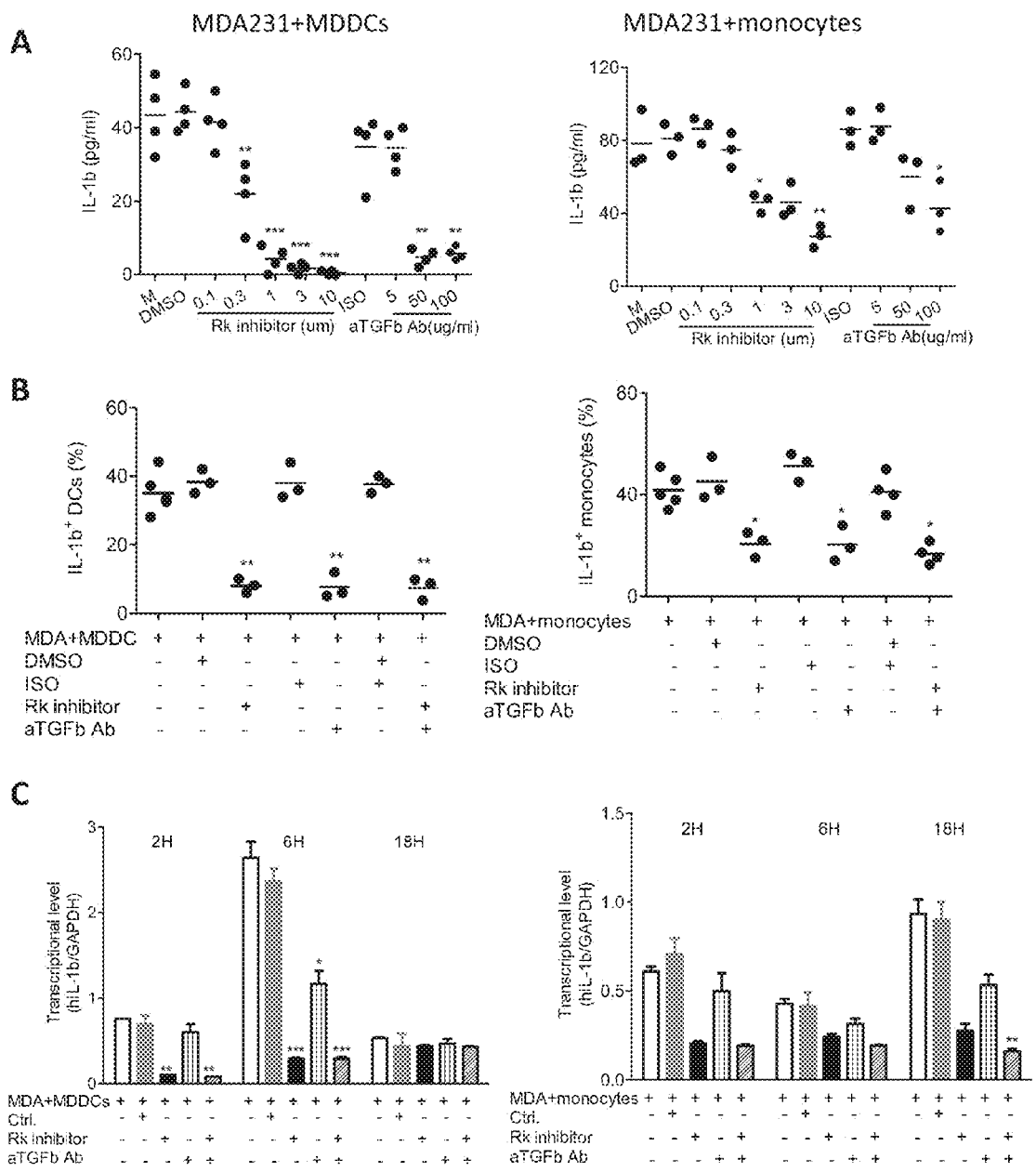
FIG. 12A-12C. A) MDA-MB231 cells were co-cultured with mDCs for 48 hours, in presence of different dose of TGF-βR kinase inhibitor or anti-TGF-β neutralizing antibody, DMSO, or isotype control respectively. IL-1β level in the sups was detected by Luminex. Values are plotted as mean±SEM. B) MDA-MB231 cells and mDCs were co-cultured for 16 hours, in presence or absence of TGF-βR kinase inhibitor and or anti-TGF-β neutralizing antibody. Intracellular staining with anti-IL-1β antibody was done and acquired by FACS. Gated on viable mDCs. The percentages of IL-1β positive CD11c cells were plotted. Dot represents each experiment. C) MDA-MB231 cells and mDCs were co-cultured in presence or absence of TGF-βR kinase inhibitor and or anti-TGF-β neutralizing antibody for different time periods as indicated. Cells were harvested and IL-1β mRNA level was detected using quantative RT-PCR. Values were normalized to GAPDH. Bars show the mean±SEM for triplicate wells from a representative experiment. *$p<0.0001$, $p<0.01$, *$p<0.05$. n.s means no significance.

To further investigate whether TGF-β signaling is involved in both transcription and secretion of IL-1β during co-culture, different doses of TGF-βR kinase inhibitor, anti-TGF-β neutralizing antibody, or control (DMSO, or isotype control respectively) were used to treat the cells in co-culture. Block TGF-β using neutralizing antibody or receptor I kinase inhibitor could affect IL-1β production from mDCs (FIG. 6D). A similar effect could also be observed when cancer cells were co-cultured with MDDCs (FIG. 12A left), whereas it partially but significantly reduced IL-1β production from monocytes (FIG. 12A right). The less amount of IL-1β released post TGF-β blocking (inhibition of receptor signaling and or blocking the effect of TGF-β through neutralizing antibody) could also be reflected by less IL-1β expressing DCs or monocytes in co-culture (FIG. 6E, and FIG. 12B). TGF-β blocking resulted in decreased mRNA level of IL-1β (FIG. 6F, and FIG. 12C). Thus, TGF-β/TGF-βR signaling is involved in IL-1β production during cancer cell co-culture with either mDCs or monocytes.

IL-1β Production Requires TAK1-Dependent Caspase-1 Activation.

Figures 7A, 7B:
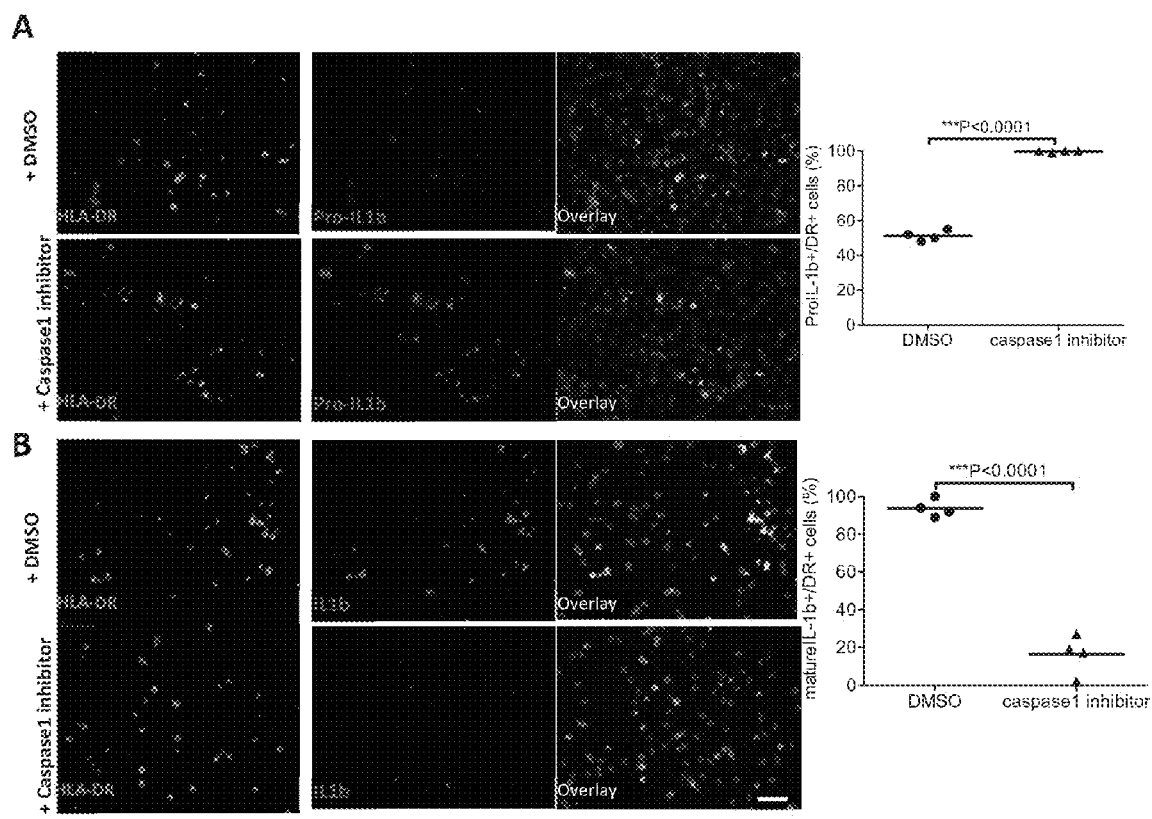
FIG. 7A-7F. A-B) MDA-MB231 and mDCs were co-cultured in chamber wells for 18 hours, in presence of caspasel inhibitor or DMSO. Cells were fixed in the well and stained for A) pro-IL-1β (center panels), HLA-DR (left panels), and DAPI (overlay panels). Chart on far right: summary data of the proportion of proIL-1β+DR+cells. B) mature IL-1β (center panels), HLA-DR (left panels), and DAPI (overlay panels). Chart on far right: summary data of the proportion of mature IL-1β+DR+cells. Bar: 90 um. C) monocytes were treated with MDA-MB231 culture sups for 16 hours in presence of 200 nm TAK1 inhibitor or DMSO. Cells were harvested and activated caspase-1 and CD11c were stained. Right panel: Summary data of the percentage of activated caspase-1 in DCs. D) mDCs were co-cultured with MDA-MB231 cells for different time periods as indicated; pTAK1 and total TAK1 was detected by specific staining and analyzed on FACS. The far left, filled-in curve is the ISO signal. E) mDCs were co-cultured with MDA-MB231 cells in presence or absence of anti-TGF-β neutralizing antibody plus TGF-βR kinase inhibitor (TGF-β blocking) for 60 min, pTAK1 was detected by specific staining and analyzed on FACS. The far left, filled-in curve is the ISO signal. F) MDA-MB231 cells were co-cultured with mDCs for 48 hours in presence of different doses of TAK1 inhibitor or DMSO. IL-1β levels were detected by Luminex in the sups after 48 hours of co-culture.

In most cases, caspase-1 is needed for proteolytic cleavage and secretion of mature IL-1β. It was tested whether TGF-β-dependent IL-1β production also required the activation of caspase-1. MDA-MB231 cells and mDCs were co-cultured in chamber well in presence of 1 uM of caspase-1 inhibitor or DMSO as vehicle control. 18 hours later, cells were fixed and stained with specific antibody against pro-peptide of IL-1β (FIG. 7A), or mature IL-1β (FIG. 7B), both accompanied with HLA-DR staining. With treatment of caspase-1 inhibitor, accumulated pro-peptide of IL-1β could be detected inside HLA-DR$^+$ DCs, while DMSO treatment showed much less pro-peptide staining, suggesting pro-peptide has been processed by functional activated caspase-1 (FIG. 7A). Four areas were counted for the percentage of proIL-1β$^+$ cells within HLA-DR$^+$ cells for both DMSO or caspase-1 inhibitor treated wells. Almost 95% of mDCs show accumulation of proIL-1β intracellularly, while only around 50% of mDCs express proIL-1β (FIG. 7A right panel). Using a similar experimental system, mature IL-1β production in presence or absence of caspase-1 inhibitor was also measured. In contrast to proIL-1β, less mature IL-1β was detected with defective caspase-1 function (FIG. 7B).

Figure 7C:
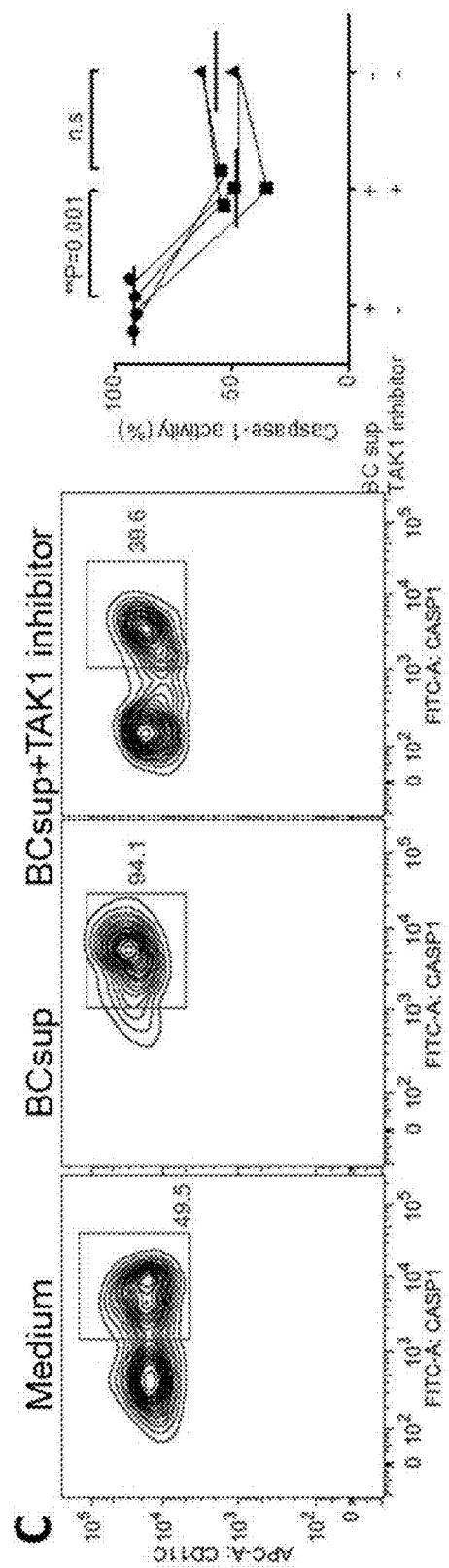

Since caspase-1 activation is also required for IL-1β release during co-culture, the inventors considered which factor(s) could possibly link TGF-βR signaling with caspase-1 activation. TAK1 (TGF-βR-activating protein kinase 1) is known to stimulate inflammasome-caspase1 activation (Eicke et al, 2013; Gong et al, 2010), and evidence shows that TAK1 activity is important for TGF-β-mediated angiogenesis and metastasis of breast tumors (Safina et al, 2008). Monocytes were treated with cancer-culture sups for 16 hours in the presence of a TAK1 specific inhibitor or DMSO as control. Caspase-1 activity was measured using the FACS based method. Cells were gated based on CD11c$^+$ viable cells. Around 94% of monocytes express active form of caspase-1 after exposure to cancer culture sups, while TAK1 inhibition prevented the activation of caspase-1 even in presence of cancer derived factors (FIG. 7C). Similar experiments were repeated using multiple cancer cell lines culture sups, and similar effect was observed (FIG. 7C).

IL-1β Production Requires TGF-β-Dependent TAK1 Activation in DCs and Monocytes.

Figure 7D:
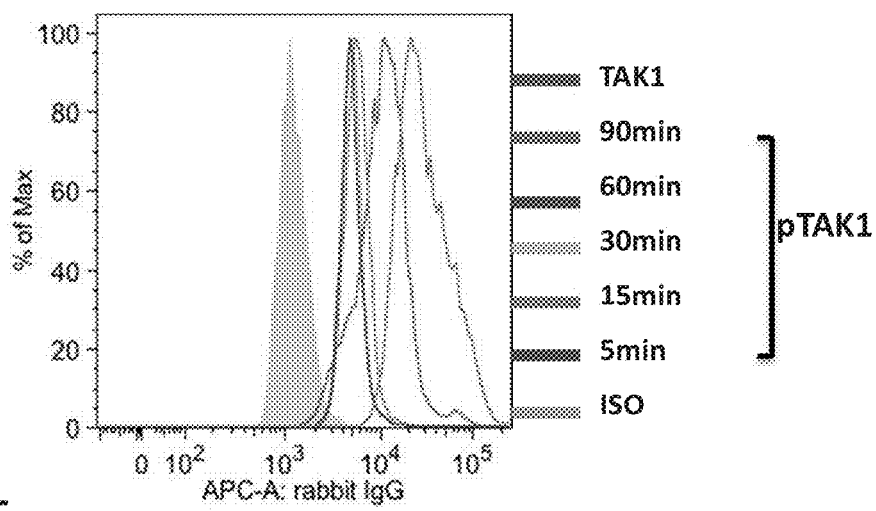
Figure 7E:
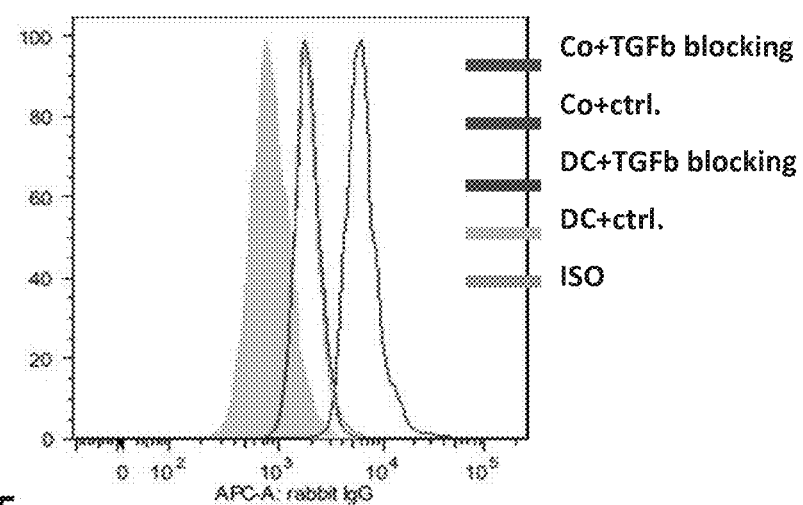
Figure 7F:
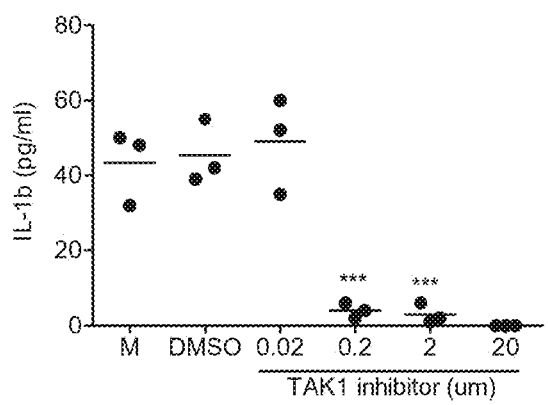

To measure whether TGF-β resulted in direct activation of TAK1, monocytes were treated with 10 ng/ml of TGF-β1 for 5-90 minutes. Soluble TGF-β1 was able to induce phosphorylation of TAK1 as early as 15 minutes (FIG. 14A). When mDCs were co-cultured with MDA-MB231 cells for 5-90 minutes, phosphorylated (p)TAK1 could only be detected after 60 minutes (FIG. 7D). To confirm that the phosphorylation of TAK1 is TGF-β mediated, TGF-β signaling blocking reagents (TGF-β neutralizing antibody and TGF-βR kinase inhibitor) were added to the co-culture of cancer cells and mDCs. Blocking TGF-β and its receptor signaling prevented phosphorylation of TAK1 (FIG. 7E). To examine whether TAK1-signaling participate in modulation of IL-1β production, a co-culture of cancer cells and myeloid cells was used. Cancer cells and monocytes, MDDC, or mDC were co-cultured for 48 hours, and IL-1β levels were measured by Luminex. Substantially lower amounts of IL-1β were secreted in the co-culture supernatants upon TAK1 inhibition (FIG. 7F, and FIG. 14B). Similarly, TAK1 inhibition prevented the expression of IL-1β by mDCs and monocytes (FIG. 14C).

Blocking TGF-β-IL-1β In Vivo Prevents Tumor Growth and Th2 Generation.

Figure 8A:
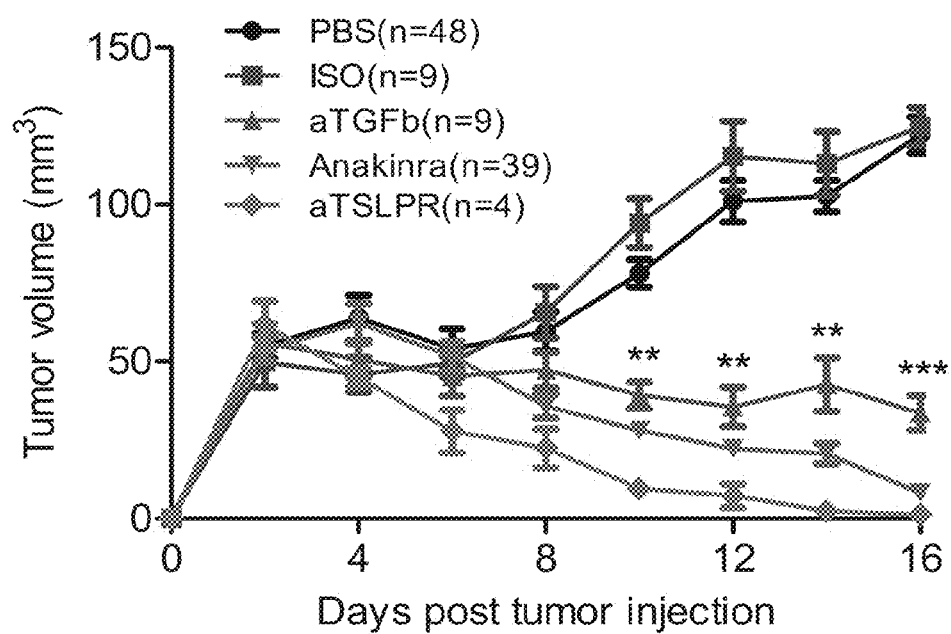
FIG. 8A-8C. Breast cancer cells was injected subcutaneously in irradiated NOD/SCIDβ2−/− mice. Autologous DCs plus CD4+ T cells and CD8+ T cells were co-injected intratumorally. Mice were treated with anti-TGF-β neutralizing antibody on D3,6,9, with Anakinra daily since D3, with anti-TSLPR neutralizing antibody on D3,6,9, or with isotype and PBS as control. A) Combined data for kinetics of tumor growth from multiple experiments was shown. Number of mice in each group was indicated. B) cytokine concentration as measured by Luminex in PBS group vs. Anakinra group vs. α-TGFβ neutralizing antibody group, as determined by Luminex in supernatants of Day 16 harvested mice breast tumor fragments were stimulated for 16 hours with PMA and ionomycin. C) IL-1β concentration in TGF-β blocking group vs. isotype control group, as determined by Luminex in supernatants of Day 16 harvested mice breast tumor fragments stimulated for 16 hours with PMA and ionomycin. See also FIG. 15.
Figure 8B:
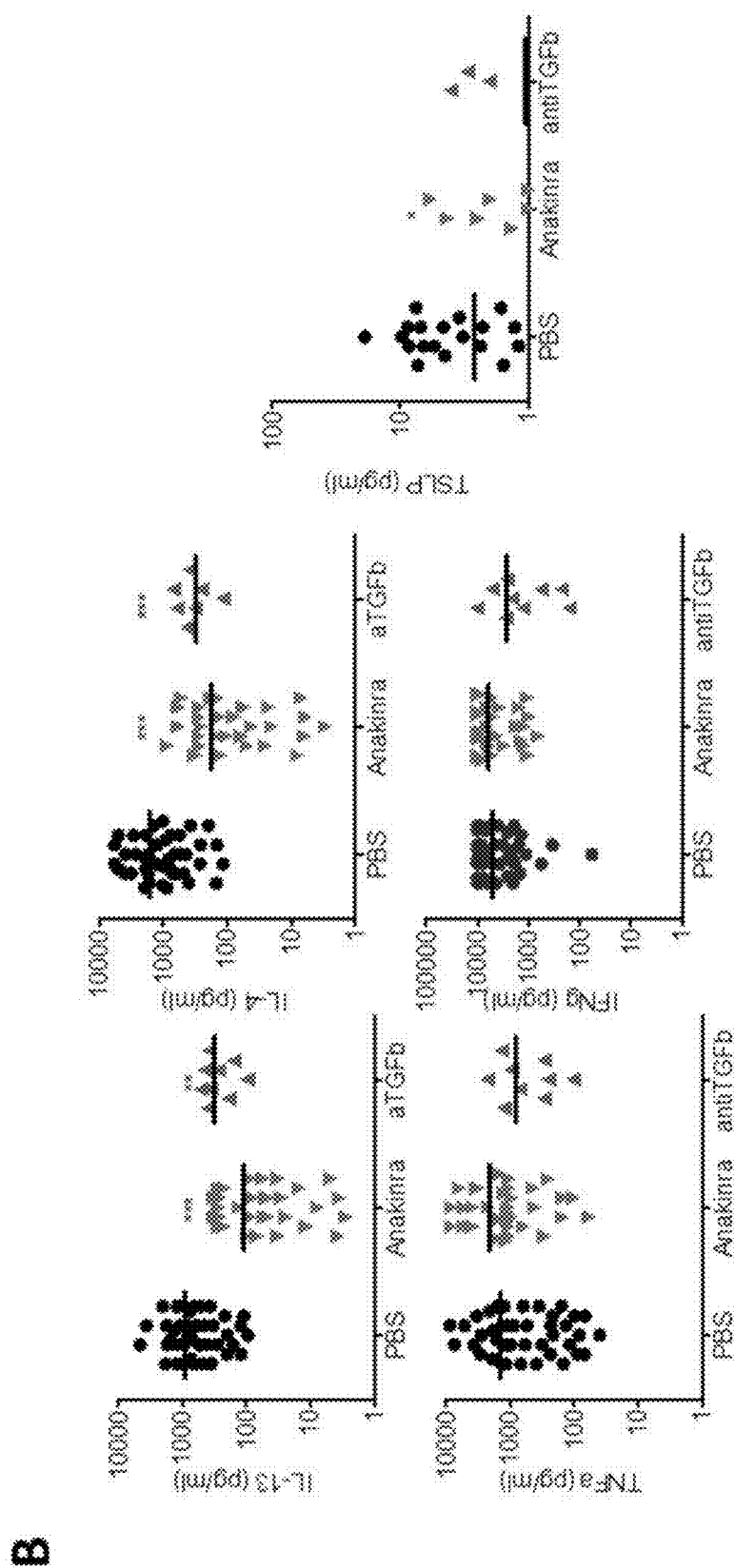
Figure 15A:
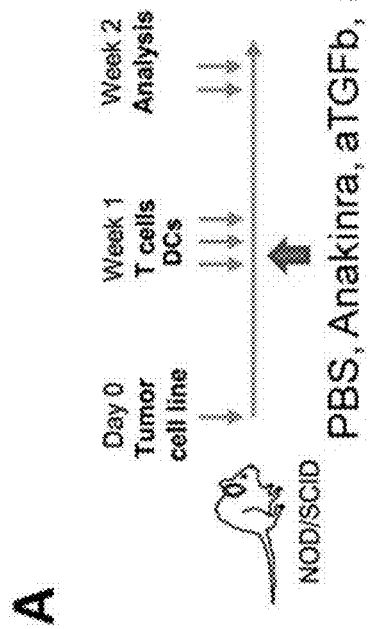
FIG. 15A-15D. A) Experimental scheme. B) Frozen tissue sections from tumor-bearing xenograft were analyzed by immunofluorescence staining. Primary tumor was stained with anti-TSLP, anti-IL-1β, antibodies, and DAPI. Bar: 90 um. C) 3 representative tumors harvested from each treatment group were shown. D) on D16, single cell suspensions were generated for intracellular cytokine expression analysis by FACS. Gate was based on viable CD4+ T cells. Dot plot shows IL-13 vs. IFN-γ.
Figure 15B:
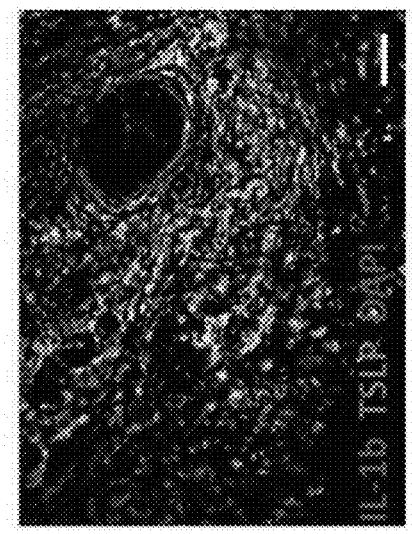
Figure 15C:
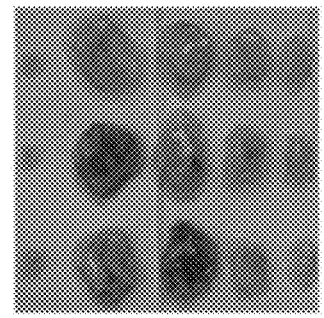

Blockade of TSLPR. using a neutralizing antibody induces tumor regression in a xenograft mice model, where the tumor growth is dependent on the TSLP-induced IL-13 (Pedroza et al., 2011). Thus, involvement of IL-1β in the TSLP-dependent in vivo model was evaluated. The availability of IL-1β in the xenograft mice model was first evaluated. HS-578t cells were injected subcutaneously into the flank of irradiated NOD/SCID/β$_2$ m$^{-/-}$ mice. MDDCs plus autologous total T cells were injected intratumorally on D3,6, and 9 after tumor cells injection (FIG. 15A). When tumors grew to 100-150 mm$^3$ in volume, mice were sacrificed and tumors were frozen in OCT for tissue staining. Similar with what observed in patient primary tumors (FIG. 5), IL-1β$^+$ cells also infiltrated in the tumor of xenograft model (FIG. 15B). Moreover, the IL-1β$^+$ cells closely localized around the TSLP$^+$ cancer cells, suggesting a crosstalk between the IL-1β$^+$ cells and cancer cells (FIG. 15B). Then we tried to understand whether TGF-β or IL-1β blocking could affect tumor growth through affecting the availability of IL-1β. Anti-TGF-β neutralizing antibody, isotype antibody as control, IL-1R antagonist Anakinra, or anti-TSLPR neutralizing antibody were each injected together with DC plus T cells (FIG. 15A). DC+T+PBS shows accelerated tumor growth, whereas with daily Anakinra injection, the tumor growth curve slowly declined shortly after an initial growth (FIG. 8A), The tumor volume was almost 10-fold increased (mean=128 mm$^3$) in the PBS group compared to the Anakinra group (mean=13 mm$^3$) by the end of the observation (FIG. 8A, P<0.0001 on day 16). The tumor volumes were comparable between anti-TGF-β neutralizing antibody and Anakinra treatment. On day 16, tumors were harvested; 3 representative tumors from each group are shown in FIG. 15C. In some experiments, small pieces of tumor tissue from mice were cultured for 16 hours in the presence of PMA and ionomycin. Th2 cytokines were measured by Luminex in the culture sups (FIG. 8B). Anakinra treatment or blocking TGF-b resulted in less IL-13 (P<0.0001, P<0.005 respectively), less IL-4 (P<0.0001, P<0.005 respectively), and Anakinra treatment also resulted in less TSLP production (P=0.03) in tumor tissue.

Figure 8C:
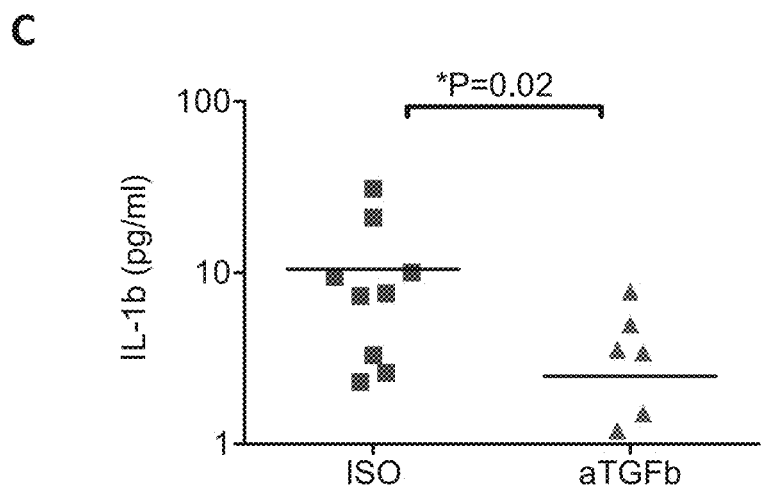
Figure 15D:
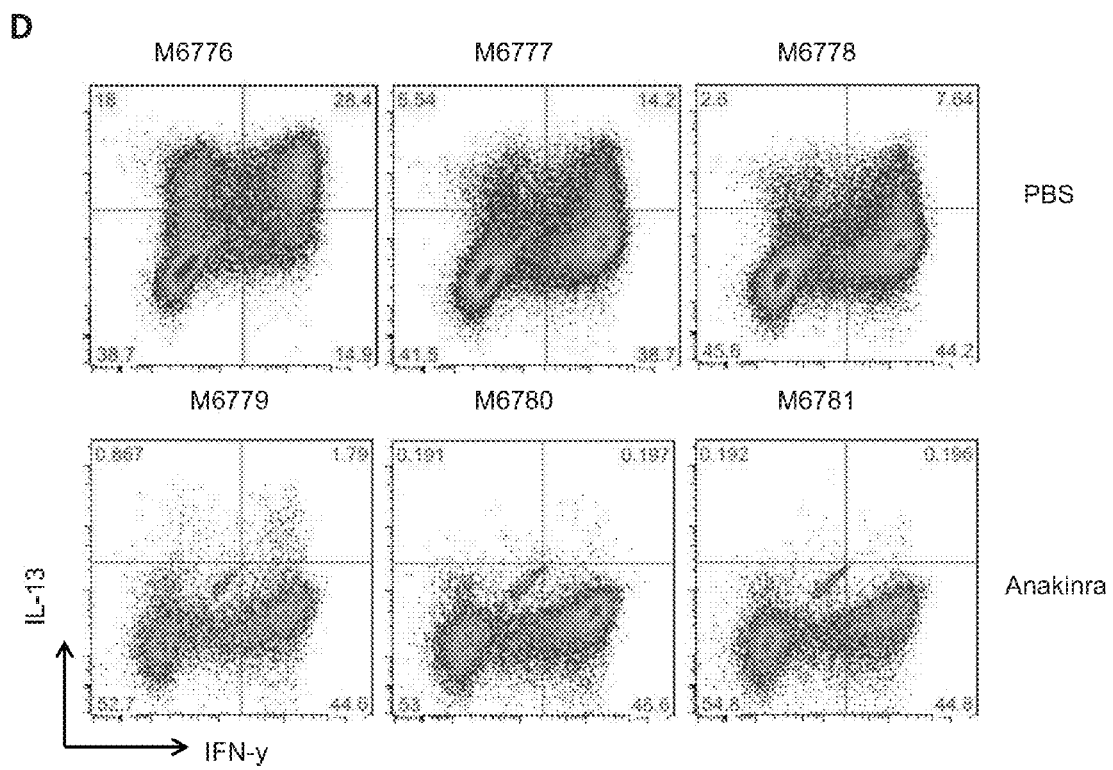

To confirm whether the decreased IL-13 level is due to less infiltration of IL-13 producing cells, single cell suspensions were prepared from the tumors harvested from both the PBS and the Anakinra treatment groups. Intracellular staining for cytokines including IL-13, IL-4, TNF-α, and IFN-γ were combined with CD4, CD3 surface staining. Cells were analyzed by FACS, and gated on viable CD4$^+$CD3$^+$T cells. The treatment showed no specific effect on TNF-α and IFN-γ. In the PBS group, about 10.2-46.4% of CD4$^+$CD3$^+$T cells express IL-13. In the Anakinra treatment group, the population dropped to 0.39-2.5%, which is significant (FIG. 15D). Importantly, as shown in FIG. 8C, anti-TGF-β neutralizing antibody treatment resulted in decreased IL-1β (P=0.02, n=9).

IL-1β is Associated with Th2 Inflammation in Breast Cancer Tissue of Patients and Shows Clinical Significance.

The level of IL-13 correlated with that of TSLP in approximately 50% of samples (FIG. 16A, pairs=148, P<0.0001 with spearman r=0.55). The level of IL-13 also positively correlated with the level of IL-1β (FIG. 17A right, pairs=149, P<0.0001 with spearman r=0.43) and IL-1α (FIG. 17A left, pairs=101, P=0.0001 with spearman r=0.375). No correlation existed between IL-13 with other cytokines tested (FIG. 16B), including IL-1Ra (pairs=45, P=0.11), IL-18 (pairs=52, P=0.77), IL-33 (pairs=51, P=0.94), and IL-25 (pairs=42, P=0.64).

Figures 17A, 17B:
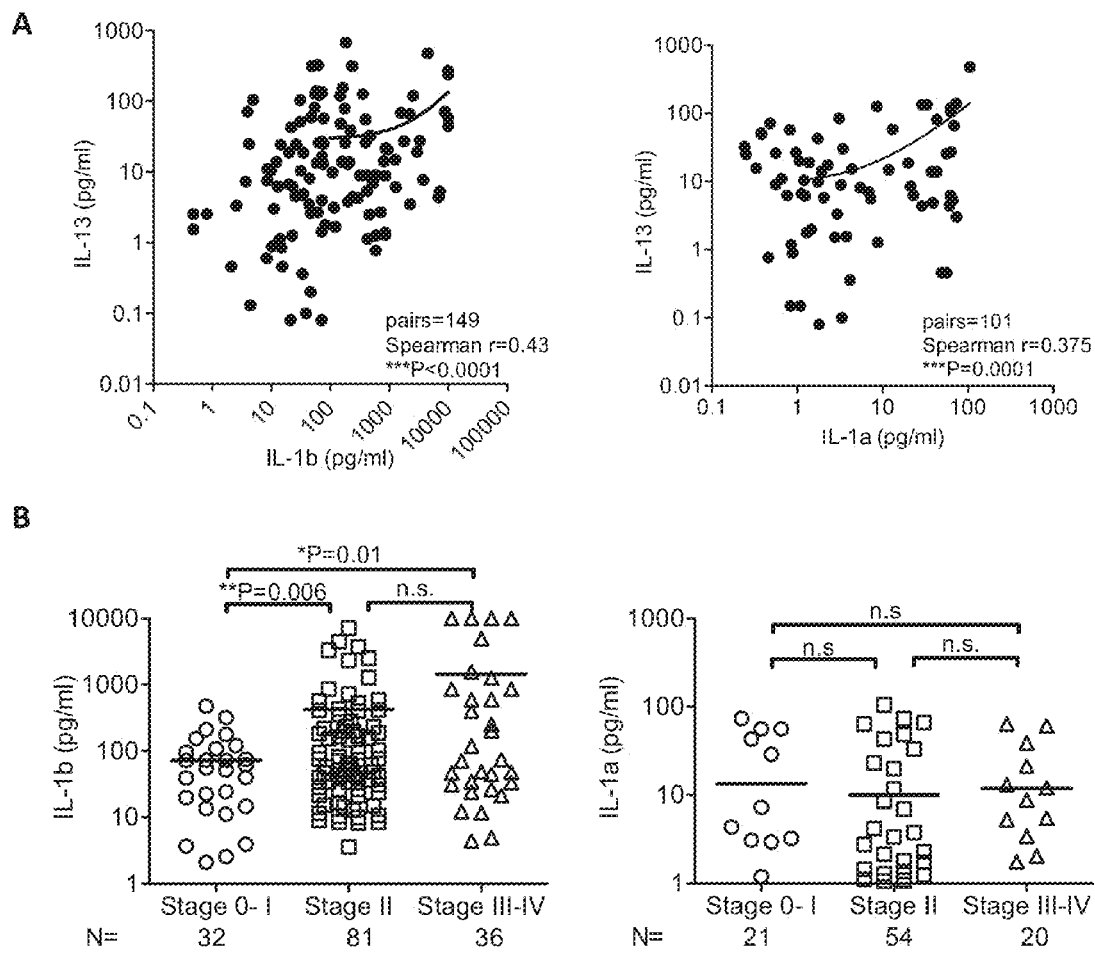
FIG. 17A-17B. A-B) levels of IL-1α, IL-1β, and IL-13 were determined by luminex or ELISA in supernatants of breast tumor fragments post PMA/ionomycin stimulation; A) levels of IL-1α and IL-1β were plotted against IL-13 from the same patient. B) IL-1β concentrations were plotted based on patients' clinical stage information. Numbers on the x-axis indicate the number of tissue samples from different patients tested. IL-1α concentrations were plotted based on patients' clinical stage information. Numbers on the x-axis indicate the number of tissue samples from different patients tested. Nonparametric t test was used. See also FIG. 16.

To investigate the clinical significance of IL-1β in breast cancer, patients were further categorized by clinical stage (0, I, II, III and IV) and grade status. Since only one patient was with stage 0, and one patient with stage IV, we compared the differences between stage 0-I, II and Patients with stage II or stage III-IV tumors appeared to have significantly higher levels of IL-1β than those with stage 0-I (P=0.006, P=0.01, respectively; FIG. 17B left). IL-1α does not have similar clinical significance as IL-1β (FIG. 179 right). Thus, IL-1β is clinical significant in breast cancer tissue, and is associated with the invasiveness status of the disease. No significant difference was found in the level of IL-1β among tumor grades (Data not shown).

Hormone receptor (ER, PR) status and HER2 expression of the patients tumor tissue were determined by pathologist of Baylor University Medical center, based on IHC staining. Statistical significance of IL-1β abundance within each group was determined using one sample T test. ER−PR+HER2− (n=1) and ER+PR−HER2− (n=7) are excluded from analysis because of limited sample number. ER−PR−HER2− group, and ER+PR+Her2+ group patients tend to have higher level of tissue IL-1β (Table 50).

TABLE 50

| Hormone status | Case n. | Estimate | Std. Error | t value | Pr(>|t|) |
|---|---|---|---|---|---|
| ER−PR−HER2− | 13 | 1947.71 | 565.68 | 3.443 | 0.000779 *** |
| ER−PR−HER2+ | 21 | 204.57 | 445.08 | 0.460 | 0.646573 |
| ER+PR−HER2+ | 11 | 743.91 | 614.96 | 1.210 | 0.228645 |
| ER+PR+HER2− | 36 | 440.71 | 339.93 | 1.296 | 0.197172 |
| ER+PR+HER2+ | 45 | 859.11 | 304.05 | 2.826 | 0.005483 ** |

IL-1β level in tumor tissue was determined via Luminex (described in methods). Hormone receptor (ER, PR) status and HER2 expression were determined by pathologist of Baylor University Medical center, based on IHC staining. ER: estrogen receptor; PR: progesterone receptor; HER2: human epidermal growth factor receptor 2. Statistical significance of IL-1β abundance within each group was determined using one sample T test. Pr value indicate the difference between each group with the number 0.
 and * indicates significant difference existing.

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

REFERENCES

The following references, to the extent that they provide exemplary procedural or other details supplementary to those set forth herein, are specifically incorporated herein by reference.

Anderson, Cancer Invest. 27:361-368, 2009.
Andre, et al., Curr Opin Oncol. 22:547-551, 2010.
Aspord, et al., J Exp Med. 204:1037-47, 2007.
Banchereau & Palucka, Nat Rev Immunol. 5:296-306, 2005.
Berry, et al., JAMA. 295:1658-1667, 2006.
Bhowmick, et al., Nature. 432:332-337, 2004
Blum, et al., Clin Breast Cancer. 7(11):850-856, 2007.
Blum, et al., J Clin Oncol. 17:485-493, 1999.
Boon, et al., Annu Rev Immunol. 12:337-365, 1994.
Carey, et al., Clin Cancer Res. 13:2329, 2007.
Chapuis, et al., Sci Transl Med. 5(174):174ra27, 2013.
Citron, et al., J Clin Oncol. 21:1431-1439, 2003.
Cobb, et al., J Immunological Methods. 365:27-37, 2011.
Cortes, et al., Lancet. 377:914-923, 2011.
Coussens, et al., Science. 33:286-291, 2013.
Craig, et al., Mol Cancer Ther. 12(1):104-16, 2013.
Cytoxan package insert, 2005.
DeNardo, et al., Breast Cancer Res. 9:212-221, 2007.
DeNardo, et al., Cancer Discov. 1:54-67, 2011.
Dinarello, Blood. 87:2095-147, 1996.
Dinarello, Arthritis Rheum. 52:1960-7, 2005b.
Dinarello, J Exp Med. 201:1355-9, 2005a.
Disis & Schiffman, Semin Oncol. 28:12-20, 2001.
Early Breast Cancer Trialists' Collaborative Group, Lancet. 365:1687-1717, 2005.
Early Breast Cancer Trialists' Collaborative Group, N Engl J Med. 319:1681-1692, 1988.
Economides, et al., Nature Med. 9:47-52, 2003.
Egloff, et al., Cancer Res. 66:6-9, 2006.
Eisenhauer, et al., Eur J Cancer. 45(2):228-247, 2009.
Finn, et al., Nat Rev Immunol. 3:630-641, 2003.
Fisher, et al., J Clin Oncol. 15:2483-2493, 1997.
Galon, et al., Science. 313:1960-1964, 2006.
Gartlehner, et al., J Rheumatol. 33:2398-408, 2006.
Gilboa, Immunity. 11:263-270, 1999.
Goldbach-Mansky, et al., N Engl J Med. 355:581-92, 2006.
Gradishar, et al., J Clin Oncol. 23(31):7794-7803, 2005.
Hawkins, et al., Arthritis Rheum. 50:607-12, 2004.
Hoffman, et al., Lancet. 364:1779-85, 2004.
J Smith, "Reprogramming T cell specific immune responses to Cyclic B1 in breast cancer patients using a TLR 8/7 agonist," Doctoral Dissertation, 2012.
Jones, et al., J Clin Oncol. 13:2567-2574, 1995.
Jurmann, et al., Am Soc Nutritional Sci. 135(8):1859-64, 2005.
Jurmann, et al., Ann NY Acad Sci. 1182:111-123, 2009.
Kao, et al., J Exp Med. 194:1313-1323, 2001.
Kineret package insert, December 2009.
Klechevsky, et al., Blood. 116:1685-1697, 2010.
Knutson, et al., J Clin Invest. 107:477-484 2001.
Kristensen, et al., Proc Natl Acad Sci USA. 109:2802-2807, 2012.
Kroemer, et al., Annu Rev Immunol. 31:51-72, 2013.
Kurzrock, Cancer 92(6 Suppl):1684-8, 2001.
Lewis, et al., J Transl Med. 4:48-60, 2006.
Liedtke, et al., J Clin Oncol. 26:1275-1281, 2008.
Linkhart, et al., J Bone Miner Res. 6(12):1285-94, 1991.
Loi, et al., J Clin Oncol. 31:860-867, 2013.
Ma, et al., Immunity. 38(4):729-41, 2013.
Mamounas, et al., J Clin Oncol. 23:3686-3696, 2005.
Mattarollo, et al., Cancer Res. 71:4809-4820, 2011.
Michaud, et al., Science. 334(6062):1573-7, 2011.
Miller, et al., NEJM. 357:2666-76, 2007.
Neidhardt-Berard, et al., Breast Cancer Res. 6:R322-328, 2004.
Palucka & Banchereau, Nat Rev Cancer. 12:265-277, 2012.
Pardoll, et al., Nat Med. 4:525-531, 1998.
Park, et al., Cancer Res. 68:8400-8409, 2008.
Pascual, et al., J Exp Med. 201:1479-86, 2005.
Pedroza-Gonzalez, et al., J Exp Med. 208(3):479-90, 2011.
Pedroza-Gonzalez, et al., J Exp Med. 208:479-90, 2011.
Petrasek, et al., Am Soc Clin Invest. 122(10):3476-89, 2012.
Portier, et al., Br J Haematol. 85:514-20, 1993.
Qi, et al., Oncol Rep. 28(4):1231-6, 2012
Rastogi, et al., J Clin Oncol. 26:778-785, 2008.
Rödel, et al., J Clin Oncol. 23(34):8688-8696, 2005.
Rosenberg, et al., Immunol Today. 18:175-182, 1997.
Safina, et al., Oncogene. 27(9):1198-207, 2008.
Saito, et al., Breast Cancer Res. 8:R65, 2006.
Sandoval, et al., Sci Transl Med. 5:72ra20, 2013.
Schneider, et al., Clin Cancer Res. 14:8010-8018, 2008.
Smith, et al., J Biol Chem. 275:1169-75, 2000.

Sorlie, et al., Proc Natl Acad Sci USA. 98:10869-10874, 2001.
Strayer, et al., Breast Cancer Res Treat. 119:551-558, 2010.
Suzuki, et al., Clin Cancer Res. 11:1521-1526, 2005.
Symmans, et al., J Clin Oncol. 25:4414-4422, 2007.
Symons, et al., PNAS. 92(5):1714-18, 1995.
Taxol package insert, 2011.
Terabe & Berzofsky, Curr Opin Immunol. 16:157-162, 2004.
Teschendorff, et al., BMC Cancer. 10:604, 2010.
Townsend, et al., Cell. 42:457-467, 1985.
Von Minckwitz, et al., SABCS. S3-2 abstract, 2011.
Wood, et al., Oncol Nurs Forum. 33(3):535-42, 2006.
Yi, et al., Cancer Research. 72(24):Suppl 3, 2012.
Young, et al., Eur J Cancer. 35(13):1773-1782, 1999.
Yu, et al., Mol Immunol. 38:981-987, 2002.
Zhang, et al., Cytokine. 42:39-47, 2008.

The invention claimed is:

1. A pharmaceutical composition comprising
   isolated, active dendritic cells displaying cyclin B1 peptide epitopes; and
   isolated, active dendritic cells displaying WT-1 peptide epitopes,
   wherein the isolated, active dendritic cells displaying WT-1 peptide epitopes have been incubated with WT-1 peptide antigens comprising SEQ ID NOs:3-8,
   and wherein the isolated, active dendritic cells displaying the cyclin B1 peptide epitopes and the isolated, active dendritic cells displaying the WT-1 peptide epitopes have been incubated with peptide antigens comprising SEQ ID NOs:9-40.

2. A method of making active, antigen-loaded dendritic cells for treating breast cancer in a subject comprising:
   isolating monocytes from the subject's blood;
   differentiating the isolated monocytes into dendritic cells;
   incubating the dendritic cells with one or more isolated cyclin B1 peptide antigens and WT-1 peptide antigens, wherein the one or more isolated WT-1 peptide antigens comprise SEQ ID NOs:3-8;
   incubating the dendritic cells with peptide antigens comprising SEQ ID NOs:9-40; and
   activating the dendritic cells.

3. A method of treating breast cancer in a subject comprising:
   isolating monocytes from the subject's blood;
   differentiating the monocytes to form dendritic cells;
   incubating the dendritic cells with an antigenic composition comprising (i) one or more isolated cyclin B1 peptide antigens and WT-1 peptide antigens, (ii) one or more dendritic cell activating agents, and (iii) peptide antigens comprising SEQ ID NOs:9-40 to form activated, antigen-loaded dendritic cells; and
   administering to the subject a first pharmaceutical composition comprising the activated, antigen-loaded dendritic cells;
   wherein the one or more isolated WT-1 peptide antigens comprise SEQ ID NOs:3-8.

4. The method of claim 3, wherein the one or more isolated cyclin B1 peptide antigens comprise SEQ ID NO:1 and/or SEQ ID NO:2.

5. The method of claim 3, wherein the step of differentiating the isolated monocytes is performed by incubating the isolated monocytes with IFNα and GM-CSF.

6. The method of claim 3, wherein the one or more dendritic cell activating agents comprise lipopolysaccharide, CD40 ligand, and CL075.

7. The method of claim 3, wherein the subject has been diagnosed with triple negative breast cancer.

8. The method of claim 3, wherein the subject has previously been administered chemotherapy and the chemotherapy did not result in a pathologic complete response in the subject.

9. The method of claim 3, wherein the breast cancer has been determined to be resistant to chemotherapy.

10. The method of claim 3, further comprising administering to the subject an IL-1R antagonist.

11. The method of claim 10, wherein the IL-1R antagonist is anakinra.

12. The method of claim 3, wherein the concentration of the active, antigen-loaded dendritic cells in the first pharmaceutical composition is between about $1 \times 10^6$ and $15 \times 10^6$ viable cells/ml.

13. The method of claim 3, wherein the concentration of the active, antigen-loaded dendritic cells in the first pharmaceutical composition is at least about $15 \times 10^6$ viable cells/ml.

14. The method of claim 3, wherein the first pharmaceutical composition is administered to the subject in combination with one or more chemotherapeutic agents comprising one or more of doxorubicin, cyclophosphamide, and paclitaxel.

15. The method of claim 3, wherein the first pharmaceutical composition is administered to the subject intratumorally.

16. The method of claim 15, further comprising administering to the subject a second pharmaceutical composition comprising the active, antigen-loaded dendritic cells, wherein the second pharmaceutical composition is administered subcutaneously.

17. The method of claim 16, wherein the concentration of the active, antigen-loaded dendritic cells in the second pharmaceutical composition is at least about $15 \times 10^6$ viable cells/ml.

18. The method of claim 16, wherein the second pharmaceutical composition is administered to the subject in combination with one or more chemotherapeutic agents comprising one or more of doxorubicin, cyclophosphamide, and paclitaxel.

19. The method of claim 3, further comprising surgically removing breast cancer tissue and/or administering radiation treatment.

* * * * *

UNITED STATES PATENT AND TRADEMARK OFFICE
CERTIFICATE OF CORRECTION

PATENT NO. : 10,023,841 B2  
APPLICATION NO. : 14/719968  
DATED : July 17, 2018  
INVENTOR(S) : Palucka et al.

Page 1 of 1

It is certified that error appears in the above-identified patent and that said Letters Patent is hereby corrected as shown below:

On the Title Page

Item (56), page 2, Line 4, please replace "Ierabe" with --Terabe-- therefore.

Signed and Sealed this  
Fourth Day of June, 2019

Andrei Iancu  
*Director of the United States Patent and Trademark Office*